(12) United States Patent
Kumar et al.

(10) Patent No.: US 8,314,103 B2
(45) Date of Patent: Nov. 20, 2012

(54) PYRIDYL DERIVATIVES, THEIR PREPARATION AND USE

(75) Inventors: Sanjay Kumar, Mumbai (IN); Kalpana Sanjay Joshi, Mumbai (IN); Vijaykumar Deore, Mumbai (IN); Mandar Ramesh Bhonde, Pune (IN); Nilambari Nilkanth Yewalkar, Mumbai (IN); Amol Arun Padgaonkar, Mumbai (IN); Asha Adrian Kulkarni-Almeida, Mumbai (IN); Maggie Joyce Rathos, Mumbai (IN); Sapna Parikh, Mumbai (IN); Nilesh Madhukar Dagia, Mumbai (IN)

(73) Assignee: Piramal Enterprises Limited, Mumbai, Maharashtra (IN)

( * ) Notice: Subject to any disclaimer, the term of this patent is extended or adjusted under 35 U.S.C. 154(b) by 39 days.

(21) Appl. No.: 12/672,485

(22) PCT Filed: Aug. 6, 2008

(86) PCT No.: PCT/IB2008/053151
§ 371 (c)(1),
(2), (4) Date: Mar. 22, 2010

(87) PCT Pub. No.: WO2009/019656
PCT Pub. Date: Feb. 12, 2009

(65) Prior Publication Data
US 2011/0077252 A1    Mar. 31, 2011

Related U.S. Application Data

(60) Provisional application No. 60/954,437, filed on Aug. 7, 2007.

(51) Int. Cl.
*A61K 31/50* (2006.01)
*C07D 401/00* (2006.01)
(52) U.S. Cl. .................. 514/252.02; 544/238; 544/319
(58) Field of Classification Search ............ 514/252.02; 544/238, 319
See application file for complete search history.

(56) References Cited

U.S. PATENT DOCUMENTS

| | | | | |
|---|---|---|---|---|
| 6,887,875 B2 * | 5/2005 | Huang et al. | ............ | 514/252.02 |
| 7,799,782 B2 * | 9/2010 | Munson et al. | ............ | 514/234.5 |
| 2004/0176385 A1 | 9/2004 | Nuss et al. | | |
| 2005/0119243 A1 | 6/2005 | Harris et al. | | |
| 2006/0199836 A1 | 9/2006 | Turtle et al. | | |
| 2010/0048547 A1 * | 2/2010 | Atallah et al. | ............ | 514/230.5 |

FOREIGN PATENT DOCUMENTS

| EP | 1 270 551 | 1/2003 |
|---|---|---|
| EP | 0 634 400 | 1/2005 |
| WO | 2006 067446 | 6/2006 |
| WO | 2007/042806 | 4/2007 |
| WO | 2007 042810 | 4/2007 |

OTHER PUBLICATIONS

Pecchi et al. CAS: 149:268069, 2008.*
Zhang et al. CAS: 142:373857, 2005.*
Vourloumis et al. CAS: 142: 74572, 2004.*
Armistead et al. CAS: 141:54365, 2004.*
Boyd et al. CAS: 138:204839, 2003.*
S. Wullschleger, et al.; TOR signaling in Growth and Metabolism; Cell 124; Feb. 10, 2006; pp. 471-484.
Giovanni Melillo.; Inhibiting Hypoxia-Inducible Factor 1 for Cancer Therapy; Mol. Cancer Res.; Sep. 4, 2006; pp. 601-605.
Bryan T. Hennessy, et al.; Exploiting the PI3K/AKT Pathway for Cancer Drug Discovery; Nature Rev. Drug Discov., Dec. 2005; vol. 4; pp. 988-1004.
Dale G. Nagle, et al.; Natural Product-Based Inhibitors of Hypoxia-Inducible Factor-1 (HIF-1); Current Drug Targets; 2006; 7; pp. 355-369.
X Sun, et al.; Gene transfer of antisense hypoxia . . . immunotherapy; Gene Therapy; 2001; 8; pp. 638-645.
A. Rapisarda, et al.; Identification of Small Molecule . . . Activation Pathway; Cancer Research 62; Aug. 1, 2002; pp. 4316-4324.
H. Zong, et al.; Overexpression of Hypoxia-inducible Factor . . . Metastases; Cancer Research 59; Nov. 15, 1999; pp. 5830-5835.
C. Rommel, et al.; PI3Kδ and PI3Kγ: partners in crime in inflammation . . . beyond?; Nature Reviews Immunology/AOP; Advance Online Publication; Feb. 9, 2007; pp. 1-11.
O. N. Ozes, et al.; NF-kB activation by tumour necrosis . . . threonine kinase; Letters to Nature; vol. 401; Sep. 2, 1999; pp. 82-85.
P. Mandal, et al.; Signaling in Lipopolysaccharide-Induced . . . Macrophages; The Journal of Immunology; 2007; 178; pp. 2542-2548.
M.W. Potter, et al.; Endotoxin (LPS) Stimulates 4E-BP1/PHAS-I Phosphorylationh in Macrophages; Journal of Surgical Research 97; 2001; pp. 54-59.
A. S. Kristof, et al.; Stimulation of Signal Transducer and . . . Rapamycin; The Journal of Biological Chemistry; vol. 278, No. 36; Sep. 5, 2003; pp. 33637-33644.
R. Selvatici, et al.; Signal transduction pathways . . . neutrophils; European Journal of Pharmacology 534; 2006; pp. 1-11.
K.S. Lee, et al.; Inhibition of phosphoinositide . . . asthma model; The FASEB Journal; 2006; pp. 455-456.
K. All et al.; Essential role for the . . . response; Letters to Nature; vol. 431; Oct. 21, 2004; pp. 1007-1011.
T. Oda, et al.; Activation of hypoxia-inducible factor 1 during macrophase differentiation; Articles in PresS. Am J Physiol Cell Physiol; Feb. 15, 2006; 291; pp. 1-35.

(Continued)

*Primary Examiner* — Rei-tsang Shiao
(74) *Attorney, Agent, or Firm* — Ladas & Parry LLP

(57) ABSTRACT

The present invention relates to pyridyl derivatives capable of inhibiting phosphatidylinositol-3-kinase (PI3k), mammalian target of rapamycin (mTOR) and/or hypoxia inducible factor 1α (HIF-1α) mediated signaling. Also disclosed are processes for preparation of the pyridyl derivatives, and their use in the manufacture of pharmaceutical compositions for the treatment of clinical conditions caused by deregulation of signaling pathways selected from one or more of PI3K, mTOR and HIF-1α pathways. The pyridyl derivatives are also useful for the treatment of conditions or disorders mediated by TNF-α.

18 Claims, No Drawings

OTHER PUBLICATIONS

V. Summa, et al.; HCV NS5b RNA-Dependent RNA . . . Design and Synthesis: J. Med. Chem., 2004; 47; pp. 5336-5339.

L. Weintraub; J. Org. Chem., vol. 33; No. 4; Apr. 1968; pp. 1679-1681.

Meng-Yang Chang.; Reaction of different χ-sulfonyl acetamides with methyl acrylate; Tetradehdron 58; 2002; pp. 5075-5080.

Jie-Jack Li, et al.; Name Reactions in Heterocyclic Chemistry; J. Het. Chem.; 1972, 9, 931; pp. 536-539.

Esko Taskinen; Thermodynamic, spectroscopic, and density . . . data of isomerization; J. Chem. Soc., Perkin Trans.; 2001; pp. 1824-1834.

V.V. Mulwad, et al.; Synthesis of indoloquinolones, triazoloindoloquinolines and its derivatives; Ind. J. Chem.; 2003; 42(8); pp. 1937-1942.

C. D. Bedford, et al.; Nonquaternary Cholinesterase . . . Acetylcholinesterase in Vitro; J. Med. Chem.; 1986; 29; pp. 2174-2183.

Z. A. Knight, et al.; A Pharmacological Map of the PI3-K . . . in Insulin Signaling; Cell 125; May 19, 2006; pp. 733-747.

H.H. Versteeg, et al.; A new phosphospecific cell-based . . . protein; Biochem J.; 2000; 350; pp. 717-722.

A.L. Moreira, et al.; Thalidomide protects mice against LPS-induced shock; Brazilian Journal of Medical and Biological Research; 1997; 30; pp. 1199-1207.

K. Terato, et al.; Collagen-Induced Arthritis in Mice; Journal of Experimental Medicine; vol. 162; Aug. 1985; pp. 637-646.

\* cited by examiner

PYRIDYL DERIVATIVES, THEIR PREPARATION AND USE

This claims the benefit of U.S. Provisional Application No.: 60/954,437 filed Aug. 7, 2007, and incorporates the same by reference.

FIELD OF INVENTION

The present invention relates to pyridyl derivatives, processes for the preparation of these compounds, pharmaceutical compositions containing the pyridyl derivatives, and use of the compounds and compositions in clinical conditions associated with cancer and inflammation.

BACKGROUND OF INVENTION

Cancer is an uncontrolled growth and spread of cells that may affect almost any tissue of the body. More than eleven million people are diagnosed with cancer every year. It is estimated that there will be sixteen million new cases every year by 2020. Cancer causes seven million deaths every year worldwide.

Cancer can be defined as abnormal growth of tissues characterized by a loss of cellular differentiation. It is caused due to a deregulation of the signaling pathways involved in cell survival, cell proliferation and cell death.

Current treatments for cancer and related diseases have limited effectiveness and a number of side effects. Cancer therapy currently falls under the following categories including surgery, radiation therapy, chemotherapy, bone marrow transplantation, stem cell transplantation, hormonal therapy, immunotherapy, antiangiogenic therapy, targeted therapy, gene therapy and others.

Activation of phosphatidylinositol-3-kinase (PI3K) results in a disturbance of control of cell growth and survival, and hence this pathway is an attractive target for the development of novel anticancer agents (Nat. Rev. Drug Discov., 2005, 4, 988-1004). The mammalian target of rapamycin (mTOR) regulates cell growth and metabolism in response to environmental cues, hence inhibitors of mTOR may be useful in the treatment of cancer and metabolic disorders (Cell, 2006, 124, 471-484). Hypoxia-inducible factor 1 (HIF-1), a molecular determinant of the response of mammalian cells to hypoxia, has led to the identification of molecular target in the treatment of cancer (Mol. Cancer Res., 2006, 4 (9), 601-605).

PI3K mediated signaling pathway plays a very important role in cancer cell survival, cell proliferation, angiogenesis and metastasis. The PI3K pathway is activated by stimuli such as growth factors, hormones, cytokines, chemokines and hypoxic stress.

Activation of PI3K results in the recruitment and activation of protein kinase B (AKT) to the membrane, which gets phosphorylated at Serine 473 (Ser-473). Thus, phosphorylation of Ser-473 of AKT is a read-out/detector for the activation of the PI3K-mediated pathway. A cell-based ELISA technique can be used to study such activation.

AKT is known to positively regulate cell growth (accumulation of cell mass) by activating the mTOR serine threonine kinase. mTOR serves as a molecular sensor that regulates protein synthesis on the basis of nutrients. mTOR regulates biogenesis by phosphorylating and activating p70S6 kinase (S6K1) which in turn enhances translation of mRNAs that have polypyrimidine tracts. The phosphorylation status of S6K1 is a bonafide read-out of mTOR function.

Most solid tumours have an aberrant PI3K pathway (Nat. Rev. Drug Discov., 2005, 4, 988-1004). Since mTOR lies immediately downstream of PI3K, these tumours also have hyperactive mTOR function.

Hypoxia is defined as loss of oxygen in tissues and is widespread in solid tumors (epithelial or mesenchymal origin) due to the tumors ability to outgrow the existing vasculature.

HIF-1 is master regulator of transcriptional response to oxygen deficiency. It is also upregulated in response to growth factor stimuli. HIF-1 has been implicated in the regulation of genes involved in angiogenesis (e.g. vascular endothelial growth factor (VEG-F), inducible nitric oxide synthase) and anaerobic metabolism (glycolytic enymes).

HIF-1 is a heterodimeric transcription factor consisting of an α (HIF-1α) and a β (HIF-1α) subunit, and is an important regulator of the growing tumor's response to hypoxia. The HIF-1α subunit is degraded rapidly in normoxic conditions and stabilized under hypoxic conditions, while HIF-1α is constitutively expressed. In general, the availability and activity of HIF-1α protein determines the bioactivity of HIF-1 (Current Drug Targets, 2006, 7, 355-369).

Over expression of HIF-1α protein has been demonstrated in many cancers and their metastasis. HIF-1α activates genes that allow the cancer cell to survive and grow in the hostile hypoxic tumor environment. Hypoxic conditions elicit cellular responses designed to improve cell oxygenation/survival through several mechanisms such as neoangiogenesis promotion, improved glycolytic flux enhancing energy production, and up regulation of molecules related to cell survival/apoptosis. Increased tumor HIF-1α has been correlated with increased angiogenesis, aggressive tumor growth, and poor patient prognosis, leading to the current interest in HIF-1α as a cancer drug target.

Various approaches have been used to inhibit HIF-1α gene transcription: through antisense strategies, through inhibition of the ability of HIF-1α to interact with proteins that modulate its activity, or through inhibition of the signal transduction pathway. The use of antisense HIF-1α is experimentally relevant in cell culture, but would be difficult to use clinically with current technology (Gene Ther., 2001, 8, 638-645).

HIF-1α is also associated with tumor progression (Cancer Res., 2002, 62, 4316-4324). In addition, over expression of HIF-1α has been demonstrated in many common human cancers such as pancreatic carcinoma, lung carcinoma, colorectal carcinoma, glioblastoma and many other types of cancers. (Cancer Res., 1999, 59, 5830-5835).

Thus, most of the cancer types will potentially benefit from molecules that target one or more of PI3K, mTOR and HIF-1α pathways.

Inflammation is the response of a tissue to injury that may be caused by invading parasites, ischemia, antigen-antibody reactions or other forms of physical or chemical injury. It is characterized by increased blood flow to the tissue, causing pyrexia, redness, swelling, and pain. Each stimulus elicits a characteristic response that has a common theme. Inflammation occurs in three distinct phases:

1. an acute transient phase characterized by local vasodilation and increased capillary permeability;
2. a subacute phase characterized by infiltration of the site by leucocytes and phagocytic cells; and
3. a chronic proliferative phase characterized by tissue degeneration and fibrosis. The recruitment of inflammatory cells to sites of injury involves the concerted interactions of several types of mediators.

Several cytokines, especially interleukin (e.g. IL-1, IL-6, IL-8) and tumor necrosis factor-α (TNF-α) play an important role in the inflammatory process. Both IL-1 and TNF-α are derived from mononuclear cells and macrophages and in turn induce the expression of a variety of genes that contribute to the inflammatory process. An increase in TNF-α synthesis/release is a common phenomenon during the inflammatory process. Inflammation is an inherent part of various disease states like rheumatoid arthritis, Crohn's disease, septic shock syndrome, atherosclerosis, among other clinical conditions.

PI3K regulates a vast number of signaling pathways (controlling adhesion, migration and phagocytosis) that are crucial in leukocyte function. Specifically, a deficiency of PI3Kγ leads to suppression of in vitro and in vivo recruitment of neutrophils and macrophages to the sites of inflammation. Moreover, it also leads to impaired neutrophil oxidative burst, dendritic-cell migration, as well as impaired T-cell activation in response to inflammatory stimuli (Nat Rev. Immunol., 2007, 7, 191-201). One of the major responses of macrophages to lipopolysacharide (LPS) is to produce TNF-α. TNF-α in turn binds to its specific receptors on leukocytes and mediates the secretion of various cytokines IL-6, IL-8, and the like. It has been reported in literature that TNF activates the PI3K-AKT cascade, which in turn leads to the activation of nuclear factor (NF-κB) (Nature, 1999, 401, 82-85). Thus, inhibiting the PI3K-AKT pathway may have therapeutic potential as anti-inflammatory agents.

LPS from gram-negative bacteria plays a decisive role in initiating pro-inflammatory responses via macrophages. LPS stimulation of macrophages leads to the phosphorylation and activation of p70S6K1 (J. Immunol., 2007, 178, 2542-2548) as well as that of 4EBP1/PHAS-1 (J. Surg. Res., 2001, 97, 54-59); both proteins are bonafide targets of mTOR. Moreover, the PI3K-mTOR pathway regulates the production of nitric oxide (J. Surg. Res., 2001, 97, 54-59) and activates STAT1-dependent transcription (J. Biol. Chem., 2003, 278, 33637-33644) in macrophages in response to LPS.

PI3K is also known to be involved in neutrophil chemotaxis (Eur. J. Pharmacol, 2006, 534, 1-11) and in the pathology of inflammation and rheumatoid arthritis (Nat. Rev. Immunol., 2007, 7, 191-201). As such, it is being considered as an important target for treating both acute and chronic inflammation. Recently, PI3K has been implicated in allergic responses and as a target for treating allergic shocks (FASEB Journal, 2006, 20, 455-456; Nature, 2004, 431, 1007-1011). HIF-1α also plays an important role in myeloid cell activation in response to inflammatory stimuli. It has been reported that HIF-1α activity is increased during the differentiation of monocytes to macrophages. This was also associated with an increase in phosphorylation, activation of p70S6 kinase and inhibition of 4EBP1 thus indicating an involvement of mTOR as well (Am. J. Physiol. Cell Physiol., 2006, 291, C104-113). Thus, targeting HIF-1α may interfere with the functioning of macrophages and thereby alleviate the inflammatory response.

US2005119243 describes the use of HIF-1 inhibitors selected from bidentate zinc chelates for the treatment of cancer.

US20060199836 describes thienopyridine compounds capable of modulating stability and activity of hypoxia inducible factor (HIF) and useful in the treatment of anemia, ischemia and hypoxia.

WO2006067446 discloses pyridine carboxamide derivatives for use as anticancer agents.

EP1270551 describes urea derivatives of general formula (i) as factor VIIa inhibitors useful in the treatment of cardiovascular disorders, thromboembolic diseases or restenosis.

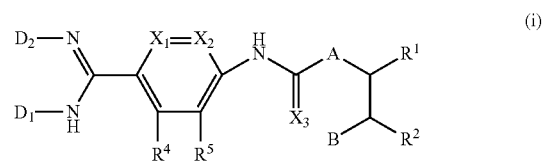

WO2007042810 describes pyrimidine derivatives of formula (ii) as inhibitors of PI3K useful in the treatment of cancer.

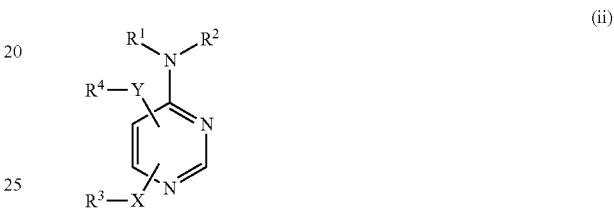

The present inventors have synthesized and screened molecules which have inhibitory activity towards PI3K and/or mTOR and/or HIF-1α. More importantly, the present inventors have designed and synthesized compounds that target one or more of PI3K, mTOR and HIF-1α pathways.

SUMMARY OF INVENTION

Thus according to one aspect of the present invention there are provided compounds of formula (I) (as described herein below).

According to another aspect there are provided compounds of formula (I), which act as inhibitors of PI3K and/or mTOR and/or HIF-1α mediated signaling.

According to another aspect there are provided compounds of formula (I), which act as inhibitors of a biological effect of TNF-α.

According to another aspect there are provided processes for producing compounds of formula (I).

According to further aspect there is provided use of compounds of formula (I) for the treatment of a condition or disorder caused by deregulation of signaling pathways selected from one or more of PI3K, mTOR and HIF-1α pathways.

According to another aspect there are provided pharmaceutical compositions comprising the compounds of formula (I) as active ingredients useful in the treatment of a condition or disorder caused by deregulation of signaling pathways selected from one or more of PI3K, mTOR and HIF-1α pathways.

According to another aspect there are provided pharmaceutical compositions comprising the compounds of formula (I) as active ingredients useful in the treatment of conditions or disorders mediated by TNF-α activity.

According to another aspect of the present invention there are provided methods for manufacture of medicaments comprising compounds of formula (I), which are useful for the treatment of a condition or disorder caused by deregulation of signaling pathways selected from one or more of PI3K, mTOR and HIF-1α pathways.

According to another aspect of the present invention there are provided methods for manufacture of medicaments comprising compounds of formula (I), which are useful for the treatment of conditions or disorders mediated by TNF-α activity.

According to another aspect of the present invention there is provided a method for treatment of a condition or disorder caused by deregulation of signaling pathways selected from one or more of PI3K, mTOR and HIF-1α pathways; comprising administering to a mammal in need thereof a therapeutically effective amount of compounds of formula (I).

According to another aspect of the present invention there is provided a method for treatment of conditions or disorders mediated by TNF-α activity; comprising administering to a mammal in need thereof a therapeutically effective amount of compounds of formula (I).

These and other objectives and advantages of the present invention will be apparent to those skilled in the art from the following description.

DETAILED DESCRIPTION OF INVENTION

The present invention discloses compounds of formula (I), in all their stereoisomeric and tautomeric forms and mixtures thereof in all ratios, their pharmaceutically acceptable salts, pharmaceutically acceptable solvates, pharmaceutically acceptable polymorphs and prodrugs;

wherein:
A and B are independently selected from carbon and nitrogen; provided that at least one of A and B is nitrogen;
$R_1$ is selected from hydrogen, alkyl, alkenyl, alkynyl, acyl, hydroxy, alkoxy, aryl, and aryloxy, or is absent;
$R_2$ is selected from hydrogen, alkyl, alkenyl, alkynyl, acyl, hydroxy, alkoxy, aryl, and aryloxy;
$R_3$ is selected from hydrogen, alkyl, alkenyl, alkynyl, acyl, hydroxy, alkoxy, aryl, aryloxy, and —O—$R_6$; or
$R_2$ and $R_3$ together with the N atom to which they are attached form a 5-membered heterocycle having at least one additional heteroatom selected from O, N and S; wherein the heterocycle may be unsubstituted or substituted; or
$R_2$ and $R_3$ together with the N atom to which they are attached form a 6- or 7-membered heterocycle, optionally having one or more additional heteroatoms selected from O, N and S; wherein the heterocycle may be unsubstituted or substituted;
$R_4$ and $R_5$ are independently selected from hydrogen, alkyl, haloalkyl, aralkyl, alkenyl, alkynyl, aryl, heterocyclyl, cycloalkyl, —O—$R_6$, and —C(O)-T-Q;
$R_6$ is selected from alkenyl and alkynyl; wherein the alkenyl and alkynyl may be unsubstituted or substituted;
T is selected from —$(CR_7R_8)_n$— and —$C(R_7R_8)C(O)$—, where n is an integer from 0 to 5;
$R_7$ and $R_8$ are independently selected from hydrogen, alkyl, haloalkyl, cycloalkyl, alkenyl, halogen, hydroxy, alkoxy, cyano, nitro, aryl, and heterocyclyl; and Q is selected from hydrogen, hydroxy, halogen, cyano, nitro, alkyl, haloalkyl, alkoxy, cycloalkyl, heterocyclyl, and aryl;
where, in $R_1$, $R_2$, $R_3$, $R_4$, $R_5$, T, $R_7$, $R_8$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$;
with a proviso that:
when $R_1$ is selected from hydrogen, alkyl, alkenyl, alkynyl, acyl, hydroxy, alkoxy, aryl, and aryloxy, then at least one of $R_4$ and $R_5$ is —C(O)-T-Q;
with a further proviso that:
when Q is selected from cycloalkyl, heterocyclyl, and aryl, then $R_2$ and $R_3$ together with the N atom to which they are attached form a 5-membered heterocycle having at least one additional heteroatom selected from O, N and S; wherein the heterocycle may be unsubstituted or substituted; or $R_2$ and $R_3$ together with the N atom to which they are attached form a 6- or 7-membered heterocycle, optionally having one or more additional heteroatoms selected from O, N and S; wherein the heterocycle may be unsubstituted or substituted.

Definitions

Listed below are definitions, which apply to the terms as they are used throughout the specification and the appended claims (unless they are otherwise limited in specific instances), either individually or as part of a larger group.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

As used herein, the term "alkyl" refers to a saturated aliphatic group, including straight or branched-chain alkyl group containing 1-20 carbon atoms. Furthermore, unless stated otherwise, the term "alkyl" includes unsubstituted alkyl groups, as well as alkyl groups which are substituted by one or more different substituents. Examples of alkyl groups containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl and the like. The "alkyl" may optionally be substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl.

The term "alkenyl" refers to an unsaturated, branched, straight chain or cyclic alkyl group having from 2 to 6 carbon atoms and at least one carbon-carbon double bond (two adjacent $sp^2$ carbon atoms). Examples of alkenyl include vinyl, allyl, 2-propenyl, crotyl, 2-isopentenyl, 2-(butadienyl), 2,4-pentadienyl, 1,4-pentadienyl, cis-2-butenyl, trans-2-butenyl, 2-methyl-2-propenyl, and the like. The "alkenyl" may optionally be substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl. Depending on the placement of double bond and substituents if any, the geometry of the double bond may be entgegen (E), or zusammen (Z), cis or trans.

The term "alkynyl" refers to an unsaturated, branched, straight chain or cyclic alkyl group having from 2 to 6 carbon atoms and at least one carbon-carbon triple bond (two adjacent sp carbon atoms). Examples of alkynyl include ethynyl, 1-propynyl, 3-propynyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl and the like. The "alkynyl" may optionally be substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl.

The term "alkoxy" unless otherwise stated, denotes alkyl group as defined above attached via oxygen linkage to the rest of the molecule. Representative examples of alkoxy groups are methoxy, ethoxy, and the like.

The term "aryl" refers to a monocyclic or polycyclic hydrocarbon group having up to 14 ring carbon atoms, preferably up to 10 ring carbon atoms, in which at least one carbocyclic ring is present that has a conjugated π electron system. Suitable examples of aryl include phenyl, naphthyl, biphenyl, fluorenyl, anthracenyl, and the like. The "aryl" may optionally be substituted by one or more substituents selected from halogen, nitro, alkyl, haloalkyl, alkoxy, acyl, acyloxy, amino, heteroarylalkyl, heterocyclyl, aryl, and aralkyl.

The term "aryloxy" refers to the unsubstituted group aryl-O— or substituted aryl-O— that includes, by way of example, optionally substituted phenoxy, optionally substituted naphthoxy, and the like.

The term "halo" or "halogen" unless otherwise stated refers to fluorine, chlorine, bromine, or iodine atom.

The term "aralkyl" refers to an alkyl group substituted with an aryl, wherein the terms alkyl and aryl are as defined herein above. Exemplary aralkyl groups include optionally substituted benzyl and the like.

The term "heterocyclyl" or "heterocycle" refers to a saturated, partially unsaturated or aromatic monocyclic or polycyclic ring system containing 3, 4, 5, 6, 7, 8, 9 or 10 ring atoms of which 1, 2, 3 or 4 are identical or different heteroatoms selected from nitrogen, oxygen and sulfur. The "heterocyclyl" or "heterocycle" may, for example, have 1 or 2 oxygen atoms and/or 1 or 2 sulfur atoms and/or 1 to 4 nitrogen atoms in the ring. The, "heterocyclyl" or "heterocycle" preferably is a 5- or 6-membered ring. The ring heteroatoms can be present in any position with respect to each other provided that the resulting "heterocyclyl" or "heterocycle" is stable. Suitable examples of "heterocyclyl" or "heterocycle" include morpholinyl, piperazinyl, imidazolyl, thiophenyl, furanyl, pyranyl, piperidinyl and the like. The "heterocyclyl" or "heterocycle" may be optionally substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—R$_6$, and —O—R$_6$, wherein R$_6$ is as described herein above.

The term "cycloalkyl" refers to a saturated or partially unsaturated cyclic hydrocarbon groups including 1, 2 or 3 rings and including a total of 3 to 20 carbons forming the rings. Suitable examples of cycloalkyl include cyclopropyl, cyclobutyl, cyclopentyl, cyclohexyl, cyclooctyl, and the like. The "cycloalkyl" may be optionally substituted with at least one group selected from halogen, hydroxy, alkoxy, oxo, alkyl, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, heterocyclyl, —COOH, —C(O)—O—R$_6$, and —O—R$_6$, wherein R$_6$ is as described herein above.

The term "amino" refers to the group —NH$_2$ which may be optionally substituted with alkyl, alkenyl, alkynyl, aryl, heterocyclyl, or cycloalkyl, wherein the terms alkyl, alkenyl, alkynyl, aryl, heterocyclyl and cycloalkyl are as defined herein above.

As used herein, the terms "treat" and "therapy" and the like refer to alleviate, slow the progression, prophylaxis, attenuation or cure of existing disease (e.g., cancer or inflammation). The term "prevent" or "prevention", as used herein, refers to delaying, slowing, inhibiting, reducing or ameliorating the onset of a disease e.g. cancer or inflammation.

In one embodiment, the present invention provides compounds of formula (Ia),

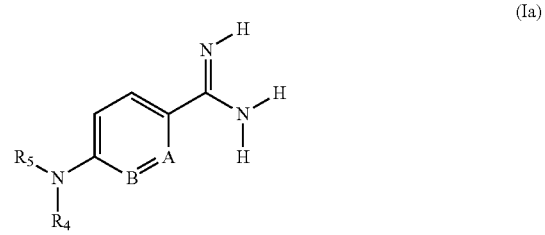

(Ia)

in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A and B are independently selected from carbon and nitrogen; provided that at least one of A and B is nitrogen;
R$_4$ is selected from hydrogen, alkyl, haloalkyl, aralkyl, alkenyl, alkynyl, aryl, heterocyclyl, cycloalkyl, —O—R$_6$, and —C(O)-T-Q;
R$_5$ is —C(O)-T-Q;
R$_6$ is selected from alkenyl and alkynyl; wherein the alkenyl and alkynyl may be unsubstituted or substituted;
T is selected from —(CR$_7$R$_8$)$_n$— and —C(R$_7$R$_8$)C(O)—, where n is an integer from 0 to 5;
R$_7$ and R$_8$ are independently selected from hydrogen, alkyl, haloalkyl, cycloalkyl, alkenyl, halogen, hydroxy, alkoxy, cyano, nitro, aryl, and heterocyclyl; and
Q is halogen;
where, in R$_4$, R$_5$, T, R$_7$ and R$_8$:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$.

In a further embodiment, the present invention provides compounds of formula (Ia), in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,

A is nitrogen;

B is carbon;

$R_4$ is selected from hydrogen, alkyl, haloalkyl, aralkyl, alkenyl, alkynyl, aryl, heterocyclyl, cycloalkyl, —O—$R_6$, and —C(O)-T-Q;

$R_5$ is —C(O)-T-Q;

$R_6$ is selected from alkenyl and alkynyl; wherein the alkenyl and alkynyl may be unsubstituted or substituted;

T is —$CR_7R_8$—;

$R_7$ and $R_8$ are independently selected from hydrogen, alkyl, haloalkyl, cycloalkyl, alkenyl, halogen, hydroxy, alkoxy, cyano, nitro, aryl, and heterocyclyl; and Q is halogen;

where, in $R_4$, $R_5$, $R_7$ and $R_8$:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$.

In a still further embodiment, the present invention provides compounds of formula (Ia), in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,

A is nitrogen;

B is carbon;

$R_4$ is hydrogen;

$R_5$ is —C(O)-T-Q;

T is —$CH_2$—; and

Q is halogen.

In another embodiment, the present invention provides compounds of formula (Ib),

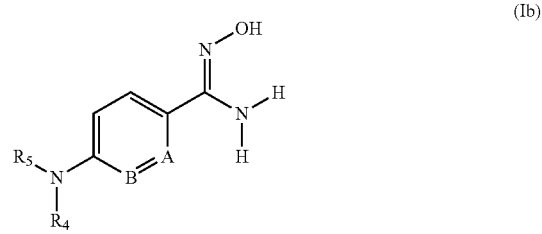

(Ib)

in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,

A and B are independently selected from carbon and nitrogen; provided that at least one of A and B is nitrogen;

$R_4$ is selected from hydrogen, alkyl, haloalkyl, aralkyl, alkenyl, alkynyl, aryl, heterocyclyl, cycloalkyl, —O—$R_6$, and —C(O)-T-Q;

$R_5$ is —C(O)-T-Q;

$R_6$ is selected from alkenyl and alkynyl; wherein the alkenyl and alkynyl may be unsubstituted or substituted;

T is selected from —$(CR_7R_8)_n$— and —$C(R_7R_8)C(O)$—, where n is an integer from 0 to 5;

$R_7$ and $R_8$ are independently selected from hydrogen, alkyl, haloalkyl, cycloalkyl, alkenyl, halogen, hydroxy, alkoxy, cyano, nitro, aryl and heterocyclyl; and Q is halogen;

where, in $R_4$, $R_5$, T, $R_7$ and $R_8$:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$;

In a further embodiment, the present invention provides compounds of formula (Ib), in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,

A is nitrogen;

B is carbon;

$R_4$ is selected from hydrogen, alkyl, haloalkyl, aralkyl, alkenyl, alkynyl, aryl, heterocyclyl, cycloalkyl, —O—$R_6$, and —C(O)-T-Q;

$R_5$ is —C(O)-T-Q;

$R_6$ is selected from alkenyl and alkynyl; wherein the alkenyl and alkynyl may be unsubstituted or substituted;

T is —(CR$_7$R$_8$)$_n$—,
n is an integer from 0 to 2;
R$_7$ and R$_8$ are independently selected from hydrogen, alkyl, haloalkyl, cycloalkyl, alkenyl, halogen, hydroxy, alkoxy, cyano, nitro, aryl, and heterocyclyl; and
Q is halogen;
where, in R$_4$, R$_5$, T, R$_7$ and R$_8$:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—R$_6$, and —O—R$_6$.

In a still further embodiment, the present invention provides compounds of formula (Ib), in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A is nitrogen;
B is carbon;
R$_4$ is hydrogen;
R$_5$ is —C(O)-T-Q;
T is —(CR$_7$R$_8$)$_n$—,
n is an integer from 0 to 2;
R$_7$ and R$_8$ are independently selected from hydrogen, halogen, and alkyl; and
Q is halogen;
where, in R$_7$ and R$_8$:
alkyl is unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

In a further embodiment, the present invention provides compounds of formula (Ib), in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A is carbon;
B is nitrogen;
R$_4$ is selected from hydrogen, alkyl, haloalkyl, aralkyl, alkenyl, alkynyl, aryl, heterocyclyl, cycloalkyl, —O—R$_6$, and —C(O)-T-Q;
R$_5$ is —C(O)-T-Q;
R$_6$ is selected from alkenyl and alkynyl; wherein the alkenyl and alkynyl may be unsubstituted or substituted;
T is —CR$_7$R$_8$—;
R$_7$ and R$_8$ are independently selected from hydrogen, alkyl, haloalkyl, cycloalkyl, alkenyl, halogen, hydroxy, alkoxy, cyano, nitro, aryl, and heterocyclyl; and
Q is halogen;

where, in R$_4$, R$_5$, R$_7$ and R$_8$:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—R$_6$, and —O—R$_6$.

In a still further embodiment, the present invention provides compounds of formula (Ib), in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A is carbon;
B is nitrogen;
R$_4$ is hydrogen;
R$_5$ is —C(O)-T-Q;
T is —CR$_7$R$_8$—;
R$_7$ and R$_8$ are independently selected from hydrogen and alkyl; and
Q is halogen;
where, in R$_7$ and R$_8$:
alkyl is unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl.

In another embodiment, the present invention provides compounds of formula (Ic),

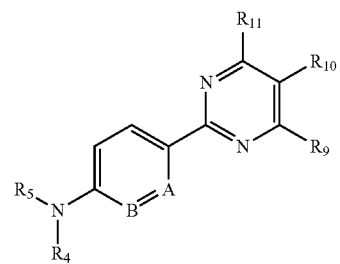

(Ic)

in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A and B are independently selected from carbon and nitrogen; provided that at least one of A and B is nitrogen;
R$_4$ and R$_5$ are independently selected from hydrogen, alkyl, haloalkyl, aralkyl, alkenyl, alkynyl, aryl, heterocyclyl, cycloalkyl, —O—R$_6$, and —C(O)-T-Q;
R$_6$ is selected from alkenyl and alkynyl; wherein the alkenyl and alkynyl may be unsubstituted or substituted;

T is selected from —(CR$_7$R$_8$)$_n$— and —C(R$_7$R$_8$)C(O)—, where n is an integer from 0 to 5;
R$_7$ and R$_8$ are independently selected from hydrogen, alkyl, haloalkyl, cycloalkyl, alkenyl, halogen, hydroxy, alkoxy, cyano, nitro, aryl, and heterocyclyl;
Q is selected from hydrogen, hydroxy, halogen, cyano, nitro, alkyl, haloalkyl, alkoxy, cycloalkyl, heterocyclyl, and aryl;
R$_9$, R$_{10}$ and R$_{11}$ are independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclyl, heterocyclylalkyl, heteroarylalkyl, aralkyl, alkylaminoalkyl, formyl, alkylcarbonyl, arylcarbonyl, aryl, aryloxy, alkylamino, alkylheteroarylamino, alkoxycarbonyl, aryloxycarbonyl, —COOH, —C(O)—O—R$_6$, and —O—R$_6$;
where, in R$_4$, R$_5$, R$_7$, R$_8$, R$_9$, R$_{10}$, R$_{11}$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—R$_6$, and —O—R$_6$.

In a further embodiment, the present invention provides compounds of formula (Ic), in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A is nitrogen;
B is carbon;
R$_4$ and R$_5$ are independently selected from hydrogen, alkyl, haloalkyl, aralkyl, alkenyl, alkynyl, aryl, heterocyclyl, cycloalkyl, —O—R$_6$, and —C(O)-T-Q;
R$_6$ is selected from alkenyl and alkynyl; wherein the alkenyl and alkynyl may be unsubstituted or substituted;
T is —CR$_7$R$_8$—;
R$_7$ and R$_8$ are independently selected from hydrogen, alkyl, haloalkyl, cycloalkyl, alkenyl, halogen, hydroxy, alkoxy, cyano, nitro, aryl, and heterocyclyl;
Q is selected from hydrogen, hydroxy, halogen, cyano, nitro, alkyl, haloalkyl, alkoxy, cycloalkyl, heterocyclyl, and aryl;
R$_9$, R$_{10}$ and R$_{11}$ are independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclyl, heterocyclylalkyl, heteroarylalkyl, aralkyl, alkylaminoalkyl, formyl, alkylcarbonyl, arylcarbonyl, aryl, aryloxy, alkylamino, alkylheteroarylamino, alkoxycarbonyl, aryloxycarbonyl, —COOH, —C(O)—O—R$_6$, and —O—R$_6$;
where, in R$_4$, R$_5$, R$_7$, R$_8$, R$_9$, R$_{10}$, R$_{11}$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—R$_6$, and —O—R$_6$.

In a still further embodiment, the present invention provides compounds of formula (Ic), in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A is nitrogen;
B is carbon;
R$_4$ is hydrogen;
R$_5$ is selected from hydrogen and —C(O)-T-Q;
R$_6$ is selected from alkenyl;
T is —CR$_7$R$_8$—;
R$_7$ and R$_8$ are independently selected from hydrogen, halogen, alkyl and aryl;
Q is selected from hydrogen and halogen;
R$_9$, R$_{10}$ and R$_{11}$ are independently selected from hydrogen, halogen, hydroxy, alkoxy, haloalkyl, alkoxycarbonyl and —O—R$_6$;
where, in R$_7$ and R$_8$:
alkyl is unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl; and
aryl is unsubstituted or substituted with at least one group selected from halogen, nitro, alkyl, haloalkyl, alkoxy, amino, heteroarylalkyl, heterocyclyl, aryl, and aralkyl.

In another embodiment, the present invention provides compounds of formula (Id),

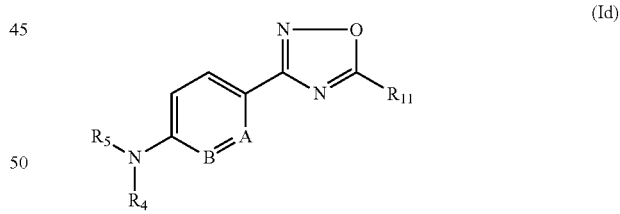

(Id)

in all their stereoisomeric and tautomeric forms and mixtures thereof in all ratios, and their pharmaceutically acceptable salts, pharmaceutically acceptable solvates, pharmaceutically acceptable polymorphs and prodrugs;
wherein,
A and B are independently selected from carbon and nitrogen; provided that at least one of A and B is nitrogen;
R$_4$ and R$_5$ are independently selected from hydrogen, alkyl, haloalkyl, aralkyl, alkenyl, alkynyl, aryl, heterocyclyl, cycloalkyl, —O—R$_6$, and —C(O)-T-Q;
R$_6$ is selected from alkenyl and alkynyl; wherein the alkenyl and alkynyl may be unsubstituted or substituted;
T is selected from —(CR$_7$R$_8$)$_n$— and —C(R$_7$R$_5$)C(O)—, where n is an integer from 0 to 5;

$R_7$ and $R_8$ are independently selected from hydrogen, alkyl, haloalkyl, cycloalkyl, alkenyl, halogen, hydroxy, alkoxy, cyano, nitro, aryl, and heterocyclyl;

Q is independently selected from hydrogen, hydroxy, halogen, cyano, nitro, alkyl, haloalkyl, alkoxy, cycloalkyl, heterocyclyl, and aryl;

$R_{11}$ is independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclyl, heterocyclylalkyl, heteroarylalkyl, aralkyl, alkylaminoalkyl, formyl, alkylcarbonyl, arylcarbonyl, aryl, aryloxy, alkylamino, alkylheteroarylamino, alkoxycarbonyl, aryloxycarbonyl, —COOH, —C(O)—O—$R_6$, and —O—$R_6$;

where, in $R_4$, $R_5$, $R_7$, $R_8$, $R_{11}$ and Q:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$.

In a further embodiment, the present invention provides compounds of formula (Id), in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,
A is nitrogen;
B is carbon;
$R_4$ and $R_5$ are independently selected from hydrogen, alkyl, haloalkyl, aralkyl, alkenyl, alkynyl, aryl, heterocyclyl, cycloalkyl, —O—$R_6$, and —C(O)-T-Q;
$R_6$ is selected from alkenyl and alkynyl; wherein the alkenyl and alkynyl may be unsubstituted or substituted;
T is —$CR_7R_8$—;
$R_7$ and $R_8$ are independently selected from hydrogen, alkyl, haloalkyl, cycloalkyl, alkenyl, halogen, hydroxy, alkoxy, cyano, nitro, aryl, and heterocyclyl;
Q is selected from hydrogen, hydroxy, halogen, cyano, nitro, alkyl, haloalkyl, alkoxy, cycloalkyl, heterocyclyl, and aryl;
$R_{11}$ is independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclyl, heterocyclylalkyl, heteroarylalkyl, aralkyl, alkylaminoalkyl, formyl, alkylcarbonyl, arylcarbonyl, aryl, aryloxy, alkylamino, alkylheteroarylamino, alkoxycarbonyl, aryloxycarbonyl, —COOH, —C(O)—O—$R_6$, and —O—$R_6$;

where, in $R_4$, $R_5$, $R_7$, $R_8$, $R_{11}$ and Q:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, heterocyclyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, aryl, alkylamino, alkylheteroarylamino, alkoxycarbonyl, aryloxycarbonyl, —COOH, —C(O)—O—$R_6$, and —O—$R_6$.

In a still further embodiment, the present invention provides compounds of formula (Id), in all their stereoisomeric and tautomeric forms and mixtures thereof in all ratios, and their pharmaceutically acceptable salts, pharmaceutically acceptable solvates, pharmaceutically acceptable polymorphs and prodrugs;

wherein,
A is nitrogen;
B is carbon;
$R_4$ is hydrogen;
$R_5$ is —C(O)-T-Q;
T is —$CR_7R_8$—;
$R_7$ and $R_8$ are independently selected from hydrogen and halogen;
Q is halogen; and
$R_{11}$ is selected from haloalkyl, unsubstituted alkyl and carboxy substituted alkyl.

Exemplary compounds of the present invention are selected from but not limited to:

Methyl 2-(5-aminopyridin-2-yl)-5,6-dihydroxypyrimidine-4-carboxylate,
2-Chloro-N-(6-(N'-hydroxycarbamimidoyl)pyridin-3-yl)acetamide,
Methyl 2-(5-(2-chloroacetamide)pyridin-2-yl)-5,6-dihydroxypyrimidine-4-carboxylate,
2-Chloro-N-[6-(N-hydroxycarbamimidoyl)pyridine-3-yl] propionamide,
2,2-Dichloro-N-[6-(N-hydroxycarbamimidoyl)pyridin-3-yl] acetamide,
2-(-5-Aminopyridin-2-yl)-6-methylpyrimidin-4-ol,
2-Chloro-N-(6-(4-hydroxy-6-methylpyrimidin-2-yl)pyridin-3-yl)acetamide,
2-(5-Aminopyridin-2-yl)-6-(trifluoromethyl)pyrimidin-4-ol,
2-(5-Aminopyridin-2-yl)-5-chloro-6-methylpyrimidin-4-ol,
2-Chloro-N-[5-(N-hydroxycarbamimidoyl)pyridin-2-yl]acetamide,
3-Chloro-N-[6-(N-hydroxycarbamimidoyl)pyridin-3-yl] propionamide,
2-Chloro-N-[5-(N-hydroxycarbamimidoyl)pyridine-2-yl] propionamide,
2-Chloro-N-[6-(5-(trifluoromethyl)-1,2,4-oxadiazol-3-yl) pyridin-3-yl]acetamide,
2-Chloro-N-[6-(5-methyl-1,2,4-oxadiazol-3-yl)pyridin-3-yl]acetamide,
3-(3-(5-(2-Chloroacetamido)pyridin-2-yl)-1,2,4-oxadiazol-5-yl)propanoic acid,
2-Chloro-N-[6-(N'-hydroxycarbamimidoyl)pyridine-3-yl]-2-phenylacetamide,
2-Chloro-2,2-difluoro-N-[6-(N'-hydroxycarbamimidoyl)pyridin-3-yl]acetamide,
2-Chloro-2,2-difluoro-N-(6-(5-(trifluoromethyl)-[1,2,4] oxadiazol-3-yl)pyridin-3-yl)acetamide,
2-Chloro-2-fluoro-N-[6-(N'-hydroxycarbamimidoyl)pyridine-3-yl]acetamide, 2-Chloro-2-fluoro-N-(6-(5-(trifluoromethyl)-1,2,4-oxadia-zol-3-yl)pyridin-3-yl)acetamide,
2-Chloro-N-[6-(5-(chloromethyl)-1,2,4-oxadiazol-3-yl)py-ridin-3-yl]acetamide,
2-Chloro-N-[6-(5-(chlorodifluoromethyl)-1,2,4-oxadiazol-3-yl)pyridin-3-yl]acetamide,
2-Chloro-N-[6-(5-(chlorodifluoromethyl)-1,2,4-oxadiazol-3-yl)pyridin-3-yl]-2,2-difluoroacetamide,
Ethyl 2-(5-(2-chloroacetamido)pyridin-2-yl)-5,6-dihydroxy-pyrimidine-4-carboxylate,
N-(6-carbamimidoylpyridin-3-yl)-2-chloroacetamide,
N-(6-carbamimidoylpyridin-3-yl)acetamide acetate,
N-(6-(5-chloro-4-hydroxy-6-methylpyrimidin-2-yl)pyridin-3-yl)acetamide,
N-(6-(4-hydroxy-5,6-dimethylpyrimidin-2-yl)pyridin-3-yl)acetamide,
2-Chloro-N-(6-(5-chloro-4-hydroxy-6-methylpyrimidin-2-yl)pyridin-3-yl)acetamide,
2-(5-aminopyridin-2-yl)-5,6-dimethylpyrimidin-4-ol,
2-(5-aminopyridin-2-yl)-6-(chloromethyl)pyrimidin-4-ol,
2-Chloro-N-(6-(4-hydroxy-5,6-dimethylpyrimidin-2-yl)py-ridin-3-yl)acetamide,
2-Chloro-N-(6-(4-(chloromethyl)-6-hydroxypyrimidin-2-yl)pyridin-3-yl)acetamide,
2-(5-aminopyridin-2-yl)-5-ethyl-6-methylpyrimidin-4-ol,
2-Chloro-N-(6-(4-hydroxy-6-(trifluoromethyl)pyrimidin-2-yl)pyridin-3-yl)acetamide,
2-(5-aminopyridin-2-yl)-5-benzyl-6-methylpyrimidin-4-ol,
6-(4-(allyloxy)-5-chloro-6-methylpyrimidin-2-yl)pyridin-3-amine,
N-(6-(4-(allyloxy)-5-chloro-6-methylpyrimidin-2-yl)pyri-din-3yl)-2-chloroacetamide,
6-(4-(allyloxy)-6-(trifluoromethyl)pyrimidin-2-yl)pyridin-3-amine,
6-(4-ethoxy-6-(trifluoromethyl)pyrimidin-2-yl)pyridin-3-amine,
6-(4-methoxy-6-(trifluoromethyl)pyrimidin-2-yl)pyridin-3-amine,
N-(6-(4-(allyloxy)-6-(triflouromethyl)pyrimidin-2-yl)pyri-din-3yl-)-2-chloroacetamide,
2-Chloro-N-(6-(4-methoxy-6-(trifluoromethyl)pyrimidin-2-yl)pyridin-3yl)acetamide,
2-Chloro-N-(6-(4-ethoxy-6-(trifluoromethyl)pyrimidin-2-yl)pyridin-3yl)acetamide,
6-(4-(allyloxy)-5-ethyl-6-methylpyrimidin-2-yl)pyridin-3-amine,
N-(6-(4-(allyloxy)-5-ethyl-6-methylpyrimidin-2-yl)pyridin-3yl)-2-chloroacetamide,
2-Chloro-N-(6-(5-ethyl-4-hydroxy-6-methylpyrimidin-2-yl)pyridin-3-yl)acetamide,
2-Chloro-N-(6-(5-chloro-4-hydroxy-6-methylpyrimidin-2-yl)pyridin-3-yl)-2-phenylacetamide,
2-Chloro-N-(6-(4-hydroxy-6-(trifluoromethyl)pyrimidin-2-yl)pyridin-3-yl)-2-phenylacetamide,
2-Chloro-N-(6-(4-hydroxy-6-(trifluoromethyl)pyrimidin-2-yl)pyridin-3-yl)propanamide,
2-Chloro-2,2-difluoro-N-(6-(4-hydroxy-6-(trifluoromethyl)pyrimidin-2-yl)pyridin-3-yl)acetamide,
N-(6-(5-Benzyl-4-hydroxy-6-methylpyrimidin-2-yl)pyri-din-3-yl)-2-chloroacetamide,
2-Chloro-N-(6-(4-chloro-6-(trifluoromethyl)pyrimidin-2-yl)pyridin-3-yl)acetamide, and
a pharmaceutically acceptable salt or a solvate thereof.

According to a further feature of the present invention there are provided processes for the preparation of the compounds of formula (I) as illustrated in the following schemes.

SCHEME 1

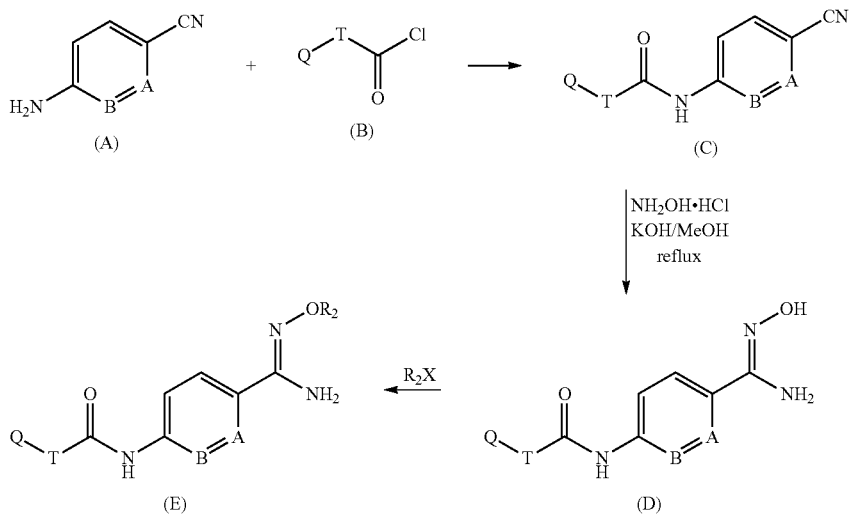

wherein,
A and B are independently selected from carbon and nitrogen; provided that at least one of A and B is nitrogen;
T is selected from —$(CR_7R_8)_n$— and —$C(R_7R_8)C(O)$—, where n is an integer from 0 to 5;
$R_7$ and $R_8$ are independently selected from alkyl, haloalkyl, cycloalkyl, alkenyl, halogen, hydroxy, alkoxy, cyano, nitro, aryl, and heterocyclyl;
Q is selected from halogen, cyano, alkoxy, heterocyclyl and cycloalkyl;
X is halogen; and
$R_2$ is selected from alkyl, alkenyl and alkynyl.

Step 1

Compound of general formula (A) is reacted with a compound of general formula (B) to obtain an acetamide of general formula (C) (Tetrahedron, 2002, 58, 5075-5080). This conversion is achieved by using a base in presence of inert solvent. The base is selected from triethylamine, potassium carbonate, sodium carbonate, cesium carbonate, and sodium bicarbonate. The inert solvent is selected from chloroform, acetone, dioxane, and tetrahydrofuran. The compound of general formula (B) is selected from chloroacetyl chloride and bromoacetyl chloride.

Step 2

The acetamide of general formula (C) obtained in step 1 is further reacted with hydroxylamine hydrochloride in presence of an inorganic base to obtain a compound of general formula (D) (J. Med. Chem., 2004, 47(22), 5336-5339). The inorganic base is selected from potassium hydroxide, sodium hydroxide, potassium carbonate, and sodium carbonate. The reaction is carried out in presence of solvents selected from methanol, ethanol, and propanol.

Step 3

The compounds of general formula (D) are further reacted with halides of formula $R_2X$ to obtain the compounds of general formula (E).

Q is selected from halogen, cyano, alkoxy, heterocyclyl and cycloalkyl;
$R_9$ is alkyl;
$R_{10}$ is selected from acyl, alkyl and aryl;
Y is selected from O, NH and N-alkyl.

Step 1

The compound of general formula (D) is reacted with a compound of general formula (F) in presence of one or more solvents selected from methanol, ethanol, and propanol to obtain a compound of general formula (G) (J. Med. Chem., 2004, 47(22), 5336-5339). The reaction mixture is further refluxed in presence of a solvent selected from xylene and toluene. The compound of general formula (F) is selected from dimethylacetylene dicarboxylate and diethylacetylene dicarboxylate.

Step 2

The compound of general formula (G) obtained in step 1 is reacted with a chloride of formula $R_{10}Cl$, followed by reaction with a chlorinating agent to obtain a compound of formula (H). The chlorinating agent is selected from thionyl chloride, phosphorus oxychloride, and phosphorus pentachloride.

Step 3

The compound of general formula (H) obtained in step 2 is reacted with a heterocyclyl amine to obtain a compound of general formula (J). The heterocyclyl amine is selected from morpholine, piperazine, N-alkyl piperazine, and the like.

SCHEME 2

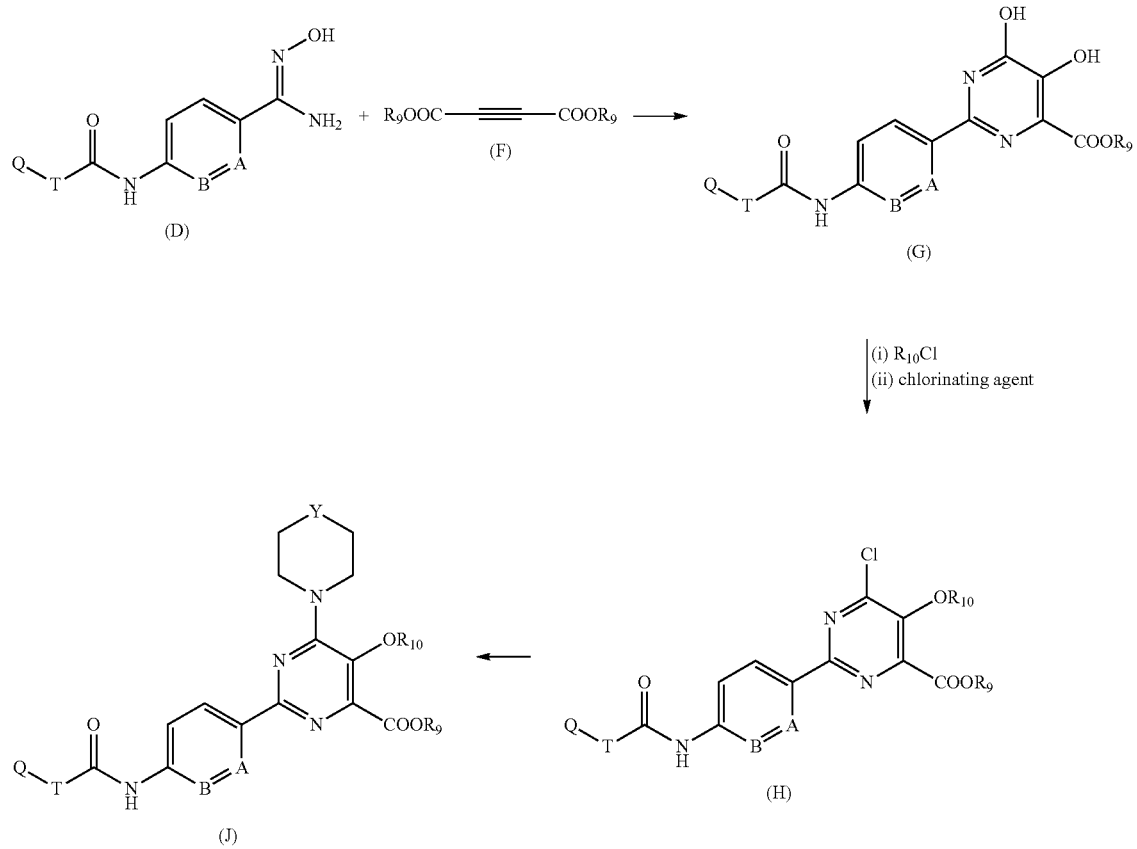

wherein,
A and B are independently selected from carbon and nitrogen; provided that at least one of A and B is nitrogen;
T is selected from $-(CR_7R_8)_n-$ and $-C(R_7R_8)C(O)-$, where n is an integer from 0 to 5;
$R_7$ and $R_8$ are independently selected from hydrogen, alkyl, haloalkyl, cycloalkyl, alkenyl, halogen, hydroxy, alkoxy, cyano, nitro, aryl, and heterocyclyl;

SCHEME 3

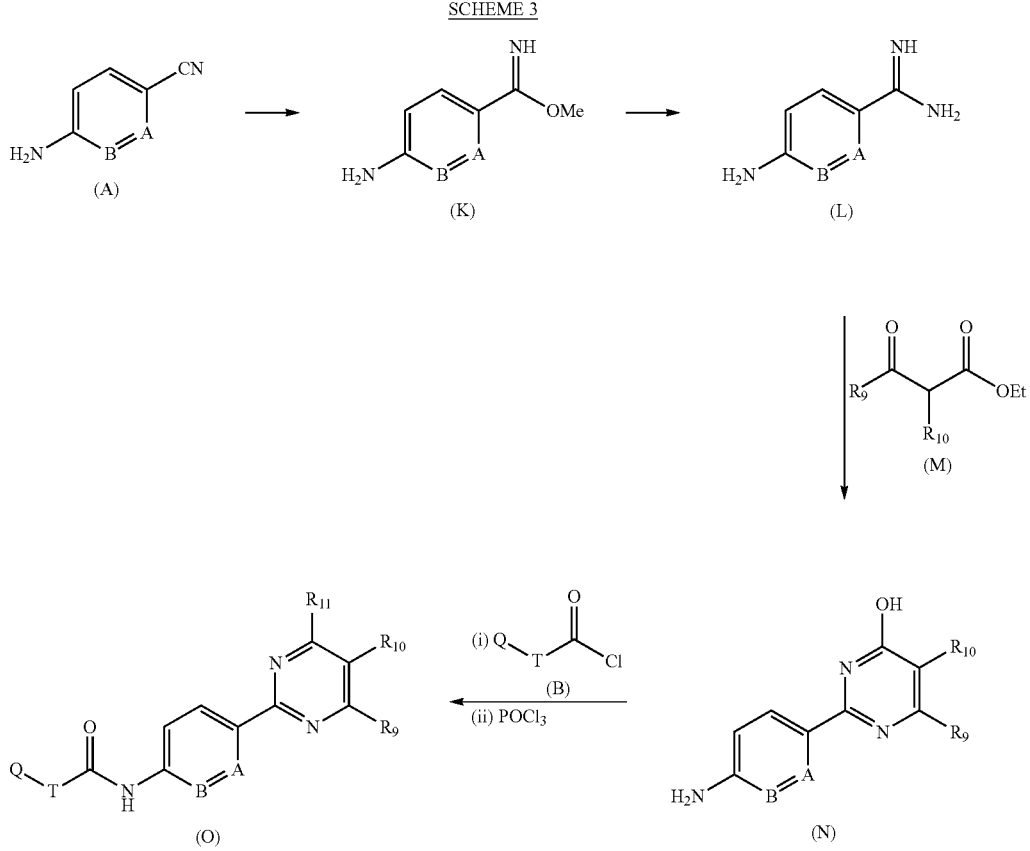

wherein,

A and B are independently selected from carbon and nitrogen; provided that at least one of A and B is nitrogen;

T is selected from $-(CR_7R_8)_n-$ and $-C(R_7R_8)C(O)-$, where n is an integer from 0 to 5;

$R_7$ and $R_8$ are independently selected from hydrogen, alkyl, haloalkyl, cycloalkyl, alkenyl, halogen, hydroxy, alkoxy, cyano, nitro, aryl, and heterocyclyl;

Q is selected from halogen, cyano, alkoxy, heterocyclyl and cycloalkyl;

$R_9$ is selected from alkyl, haloalkyl and aryl;

$R_{10}$ is selected from H, halogen, alkyl and aryl;

$R_{11}$ is selected from hydroxy and halogen.

Step 1

The compound of general formula (A) is reacted with hydrogen chloride in methanol to obtain a compound of general formula (K), which is further reacted with ammonia in methanol to obtain a compound of general formula (L) (J. Org. Chem., 1968, 33(4), 1679).

Step 2

The compound of general formula (L) obtained in step 1 is reacted with a dicarbonyl ester of general formula (M) to obtain a compound of general formula (N) (J. Het. Chem., 1972, 9, 931; Name Reactions in Heterocyclic Chemistry, Jie-Jack Li, Wiley Interscience, page. 539). This reaction is carried out in presence of a base and a solvent. The base is selected from sodium carbonate, potassium carbonate, and cesium carbonate. The solvent is selected from methanol, ethanol, and the like.

Step 3

The compound of general formula (N) is reacted with a compound of general formula (B) to obtain a compound of general formula (O) (Tetrahedron, 2002, 58, 5075-5080), wherein $R_{11}$ is hydroxy. This conversion is achieved by using a base in presence of inert solvent. The base is selected from triethylamine, potassium carbonate, sodium carbonate, cesium carbonate, and sodium bicarbonate. The inert solvent is selected from chloroform, acetone, dioxane, and tetrahydrofuran. The compound of general formula (B) is selected from chloroacetyl chloride and bromoacetyl chloride.

Step 4

The compound of general formula (O), wherein $R_{11}$ is hydroxy is reacted with a halogenating agent such as phosphoryl chloride ($POCl_3$), thionyl chloride and phosphorus pentachloride to obtain a compound of general formula (O) wherein $R_{11}$ is halogen. This conversion is achieved by using a base in presence of a solvent.

The base is selected from dimethylaniline, dimethyl aminopyridine and triethylamine. The solvent is selected from acetonitrile, tetrahydrofuran and dioxane.

SCHEME 4

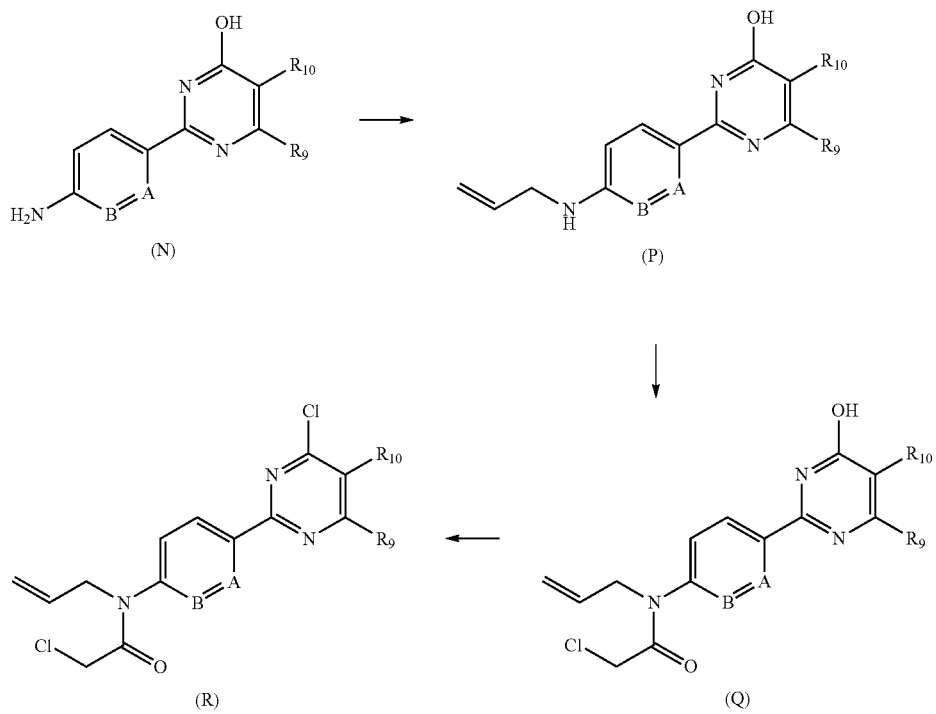

wherein,

A and B are independently selected from carbon and nitrogen; provided that at least one of A and B is nitrogen;

$R_9$ is selected from alkyl, haloalkyl and aryl;

$R_{10}$ is selected from H, halogen, alkyl and aryl.

Step 1

A compound of general formula (N) is reacted with allyl bromide in presence of a base in an inert solvent to yield compound of general formula (P) (J. Chem. Soc. Perkin. Trans. 2 Eng., 2001, 9, 1824-1834). The base is selected from sodium hydride, sodium-tert-butoxide, sodamide, cesium carbonate, and potassium-tert-butoxide.

The inert solvent is selected from tetrahydrofuran and dioxane.

Step 2

The compound of general formula (P) obtained in step 1 is treated with halo acetyl chloride to obtain a compound of general formula (Q) (Tetrahedron, 2002, 58, 5075-5080). This conversion is achieved by using a base in presence of inert solvent. The base is selected from triethylamine, potassium carbonate, sodium carbonate, cesium carbonate, and sodium bicarbonate. The inert solvent is selected from chloroform, acetone, dioxane, and tetrahydrofuran. The haloacetyl chloride is selected from chloroacetyl chloride and bromoacetyl chloride.

Step 3

The compound of general formula (Q) is reacted with reagents selected from thionyl chloride, phosphorus oxychloride, and phosphorus pentachloride to give compound of general formula (R) (Ind. J. Chem., 2003, 42(8), 1937-1942).

SCHEME 5

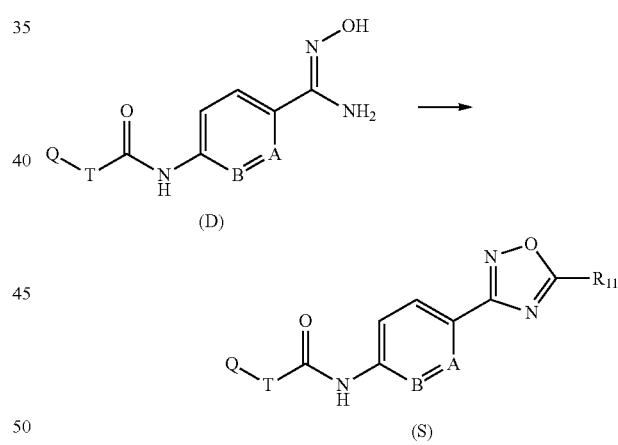

wherein,

A and B are independently selected from carbon and nitrogen; provided that at least one of A and B is nitrogen;

T is selected from —$(CR_7R_8)_n$— and —$C(R_7R_8)C(O)$—, where n is an integer from 0 to 5;

$R_6$ is selected from alkenyl and alkynyl; wherein the alkenyl and alkynyl may be unsubstituted or substituted;

$R_7$ and $R_8$ are independently selected from hydrogen, alkyl, haloalkyl, cycloalkyl, alkenyl, halogen, hydroxy, alkoxy, cyano, nitro, aryl, and heterocyclyl;

Q is independently selected from hydrogen, hydroxy, halogen, cyano, nitro, alkyl, haloalkyl, alkoxy, cycloalkyl, heterocyclyl, and aryl;

$R_{11}$ is independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclyl, heterocyclylalkyl, heteroarylalkyl, aralkyl, alkylaminoalkyl, formyl, alkylcarbonyl, arylcarbonyl, aryl, aryloxy, alkylamino, alkylheteroarylamino, alkoxycarbonyl, aryloxycarbonyl, —COOH, —C(O)—O—$R_6$, and —O—$R_6$.

Compound of general formula (S) is prepared by reacting compound of general formula (D) with substituted or unsubstituted acetic anhydride or acetyl chloride (J. Med. Chem., 1986, 29, 2174-2183).

With respect to the compounds of formula (I), the present invention also includes all stereoisomeric forms and mixtures thereof in all ratios and their pharmaceutically acceptable salts.

It will be appreciated by those skilled in the art that the compounds of the present invention may also be utilized in the form of their pharmaceutically acceptable salts or solvates thereof. The pharmaceutically acceptable salts of the compounds of the present invention are in particular salts which are non-toxic, or which can be used physiologically.

Thus, when the compounds of the present invention represented by the general formula (I) contain one or more basic groups, i.e. groups which can be protonated, they can form an addition salt with an inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

Thus, when the compounds of the present invention represented by the general formula (I) contain an acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, arginine, guanidine, diethanolamine, choline, tromethamine [tris(hydroxymethyl)aminomethane].

The pharmaceutically acceptable salts of the present invention can be synthesized from the subject compound, which contains a basic or an acidic moiety, by conventional chemical methods. Generally the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, tetrahydrofuran (THF), dioxane or mixtures of these solvents.

The present invention furthermore includes all solvates of the compounds of the formula (I), for example hydrates, and the solvates formed with other solvents of crystallization, such as alcohols, ethers, ethyl acetate, dioxane, dimethylformamide (DMF), or a lower alkyl ketone, such as acetone, or mixtures thereof.

Various polymorphs of compounds of general formula (I), forming part of this invention may be prepared by crystallization of compounds of formula (I) under different conditions. The different conditions are, for example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by infrared spectroscopy, solid probe nuclear magnetic resonance (NMR) spectroscopy, differential scanning calorimetry, powder x-ray diffraction or such other techniques.

The present invention also includes prodrugs and other physiologically acceptable derivatives of compounds of formula (I). The expression "prodrug" refers to compounds that are drug precursors, which following administration, release the drug in vivo via a chemical or physiological process e.g., a prodrug on being brought to the physiological pH or through an enzyme action is converted to the desired drug form.

The compounds within the scope of the present invention find use in the treatment of conditions or disorders caused due to deregulation of signaling pathways selected from one or more of PI3K pathway, mTOR pathway and HIF-1α pathway. Embodiments of compounds of the present invention can be used to reduce, inhibit, or diminish the proliferation of tumor cells, and thereby assist in reducing the size of a tumor. Representative conditions or disorders that may be treated by compounds of formula (I) include, but are not limited to bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, renal cancer among others.

Activation of PI3K-AKT pathway has been reported in inflammatory disorders. TNF-α mediates its proinflammatory effects via the activation of PI3K-AKT cascade. Activation of HIF-1α has been documented in inflammatory disorders.

Embodiments of compounds of the present invention, which are inhibitors of PI3K pathway and/or HIF-1α pathway may have therapeutic potential as anti-inflammatory agents.

Embodiments of compounds of the present inventions are inhibitors of PI3K pathway and/or TNF-α and find use in therapies for disorders mediated by PI3K and/or TNF-α activity, such as: inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegener's granulomatosis, meningitis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, ankylosing spondylitis, skin delayed-type hypersensitivity disorders, Alzheimer's disease, systemic lupus erythematosus and allergic conditions, among others.

Pharmaceutical Compositions and Methods

According to another aspect of the present invention there are provided pharmaceutical compositions comprising the compounds of formula (I) as active ingredients, useful in the treatment of conditions or disorders caused due to deregulation of signaling pathways selected from one or more of PI3K pathway, mTOR pathway and HIF-1α pathway. The pharmaceutical compositions comprising the compounds of formula (I) as active ingredients are also useful for the treatment of disorders (e.g. inflammatory disorders) mediated by PI3K and/or TNF-α activity.

The pharmaceutical preparations according to the invention are prepared in a manner known per se and familiar to one skilled in the art. Pharmaceutically acceptable inert inorganic and/or organic carriers and/or additives can be used in addition to the compounds of formula (I), and/or their physiologically tolerable salts. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

According to another aspect of the present invention there are provided methods for manufacture of medicaments comprising compounds of formula (I), which are useful for the treatment of conditions or disorders caused due to deregulation of signaling pathways selected from one or more of PI3K pathway, mTOR pathway and HIF-1α pathway. There are also provided methods for manufacture of medicaments comprising compounds of formula (I), which are useful for the treatment of disorders (e.g. inflammatory disorders) mediated by PI3K and/or TNF-α activity.

The pharmaceutical preparations normally contain about 1 to 99%, for example, about 5 to 70%, or from about 10 to about 30% by weight of the compound of the formula (I) and/or its physiologically tolerable salt. The amount of the active ingredient of the formula (I) and/or its physiologically tolerable salt in the pharmaceutical preparations normally is from about 5 to 500 mg.

According to another aspect of the present invention there is provided a method for treatment of conditions or disorders caused due to deregulation of signaling pathways selected from one or more of PI3K pathway, mTOR pathway and HIF-1α pathway, comprising administering to a person in need thereof a therapeutically effective amount of compounds of formula (I).

According to another aspect of the present invention there is provided a method for treatment of of disorders mediated by TNF-α activity, comprising administering to a person in need thereof a therapeutically effective amount of compounds of formula (I).

The dose of the compounds of this invention which is to be administered will depend upon a variety of factors including the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

The dose to be administered daily is to be selected to produce the desired effect. A suitable dose is about 1 to 100 mg/kg/day of the compound of formula (I) and/or their physiologically tolerable salt, for example, about 1 to 50 mg/kg/day of a compound of formula (I) or a pharmaceutically acceptable salt of the compound. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic to the patient.

The pharmaceuticals can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

In addition to the active ingredient of the general formula (I) and/or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of the general formula (I) and/or their physiologically tolerable salts. Furthermore, in addition to at least one compound of the general formula (I) and/or its physiologically tolerable salt, the pharmaceutical preparations can also contain one or more other therapeutically or prophylactically active ingredients.

By "pharmaceutically acceptable" it is meant the carrier, diluent, excipients, and/or salt must be compatible with the other ingredients of the formulation, and not deleterious to the recipient thereof.

It is understood that modifications that do not substantially affect the activity of the various embodiments of this invention are included within the invention disclosed herein. Accordingly, the following examples are intended to illustrate but not to limit the present invention.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Unless otherwise stated all temperatures are in degree Celsius. Also, in these examples and elsewhere, abbreviations have the following meanings:
List of Abbreviations
g: grams
mmol: millimole
mL: milliliter
DMSO-$d_6$: Dimethyl sulfoxide deuterated
MHz: Mega hertz
NaOH: Sodium hydroxide
HCl: Hydrochloric acid
THF: Tetrahydrofuran
$CD_3OD$: Methyl alcohol deuterated
DMF: Dimethyl formamide
Room temperature: 25° C.±3° C.
NaH: Sodium hydride
$K_2CO_3$: Potassium carbonate
$POCl_3$: Phosphoryl chloride
$MgCl_2$: Magnesium chloride Example 1

5-Amino-N-hydroxypyridin-2-carboxamidine

To a solution of potassium hydroxide (0.28 g, 4.2 mmol) in dry methanol (20 mL) was added hydroxylamine hydrochloride (0.29 g, 4.2 mmol) and the mixture was stirred for 30 minutes. White precipitate of potassium chloride obtained was filtered and to the filtrate was added 5-amino-2-cyanopyridine (0.50 g, 4.2 mmol) and the reaction mixture was stirred at reflux temperature for 6 hours. The reaction mixture was then concentrated and the crude product obtained was triturated with diethyl ether to obtain the title compound.

Yield: 0.61 g (95%); $^1$H NMR (DMSO-$d_6$, 300 MHz): δ 5.54 (s, 2H), 5.58 (s, 2H), 6.87-6.91 (m, 1H), 7.48-7.50 (d, 1H), 7.84 (s, 1H), 9.40 (s, 1H); MS m/e: 153 (M+1).

Example 2

Methyl 2-(5-aminopyridin-2-yl)-5,6-dihydroxypyrimidine-4-carboxylate

To a stirred solution of compound of example 1 (0.30 g, 1.97 mmol) in methanol (10 mL) was added dimethyl acetylenedicarboxylate (0.34 g, 2.36 mmol) and the reaction mixture was heated at 60° C. for 4 hours. Methanol was removed under reduced pressure and xylene (20 mL) was added to the reaction mixture and heated at 140° C. for 12 hours. The reaction mixture was then concentrated, and residue obtained was dissolved in 5% aqueous NaOH (20 mL) and was washed with ethyl acetate (2×50 mL) to remove unreacted organic impurities. Aqueous layer was then acidified with dilute 10% acetic acid, extracted with ethyl acetate (3×50 mL), dried over anhydrous sodium sulfate and concentrated to obtain the title compound.

Yield: 0.025 g (5%); $^1$H NMR (DMSO-$d_6$, 300 MHz): δ 3.83 (s, 3H), 5.96 (s, 2H), 6.99-7.01 (m, 1H), 7.84-7.87 (d, 1H), 7.94 (s, 1H), 11.95 (s, 2H); MS m/e: 261 (M−1).

Example 3

2-Chloro-N-(6-cyanopyridin-3-yl)acetamide

Triethylamine (0.50 g, 4.9 mmol) and chloroacetyl chloride (0.56 g, 4.9 mmol) were added dropwise at 0° C. to a stirred suspension of 5-Amino-2-cyanopyridine (0.27 g, 2.25 mmol) in chloroform (10 mL). The mixture was stirred at room temperature for 12 hours. The reaction mixture was diluted with chloroform (50 mL) and washed with water (2×50 mL). The organic layer was dried over anhydrous sodium sulfate, concentrated and the crude product obtained was crystallized from chloroform:petroleum ether (1:2) to obtain the title compound.

Yield: 0.42 g (95%); $^1$H NMR (DMSO-d6, 300 MHz): δ 4.35 (s, 2H), 7.99-8.01 (d, 1H), 8.24-8.26 (m, 1H), 8.40 (s, 1H), 10.98 (s, 1H); MS m/e: 195.96 (M+1).

Example 4

2-Chloro-N-(6-(N'-hydroxycarbamimidoyl)pyridin-3-yl)acetamide

Hydroxylamine hydrochloride (0.16 g, 2.3 mmol) was added to a solution of potassium hydroxide (0.152 g, 2.3 mmol) in methanol and the mixture was stirred for 30 minutes and filtered. To the filtrate, compound of example 3 (0.3 g, 1.53 mmol) was added and reaction mixture was refluxed for 4 hours. After completion of reaction the mixture was cooled, concentrated and triturated with diethyl ether to obtain the title compound.

Yield: 0.325 g (92.50%); $^1$H NMR (DMSO-$d_6$, 300 MHz): δ 4.35 (s, 2H), 5.79 (s, 2H), 7.83-7.84 (d, 1H), 8.05-8.07 (m, 1H), 8.78 (s, 1H), 9.84 (s, 1H), 10.85 (s, 1H); MS m/e: 229.04 (M+1).

Example 5

Methyl 2-(5-(2-chloroacetamide)pyridin-2-yl)-5,6-dihydroxypyrimidine-4-carboxylate To a suspension of compound of example 4 (0.528 g, 2.3 mmol) in methanol (20 mL), was added dimethyl acetylenedicarboxylate (0.394 g, 2.77 mmol) and the reaction mixture was stirred at 60-65° C. for 3 hours. Methanol was removed under reduced pressure and xylene (50 mL) was added to the solid residue and heated at 140-145° C. for 12 hours. The reaction mixture was cooled and filtered to obtain the title compound.

Yield: 0.270 g (35%); $^1$H NMR (DMSO-$d_6$, 300 MHz): δ 3.84 (s, 3H), 4.34 (s, 2H), 8.19-8.21 (m, 2H), 8.90 (s, 1H), 10.90 (s, 1H), 12.57 (bs, 2H); MS m/e: 338.94 (M+1).

Example 6

N-[6-(N-Hydroxycarbamimidoyl)pyridin-3-yl]-2-morpholin-4-ylacetamide

Compound of example 4 (0.10 g, 0.44 mmol) was stirred in morpholine (1 mL) at 25 ° C. for 2 hours. The reaction mixture was then diluted with water and extracted with chloroform (2×50 mL), followed by extraction with ethyl acetate (2×50 mL). Both organic layers were dried over anhydrous sodium sulfate and concentrated. The crude product obtained was purified using column chromatography (silica gel, 1% methanol in chloroform as an eluent) to obtain the title compound.

Yield: 0.068 g (56%); $^1$H NMR (DMSO-$d_6$, 300 MHz): δ 2.63-2.65 (m, 4H), 3.15 (s, 2H), 3.62-3.63 (m, 4H), 5.76 (s, 2H), 7.77-7.79 (d, 1H), 8.04-8.08 (dd, 1H), 8.78 (s, 1H), 9.79 (s, 1H), 10.06 (bs, 1H); MS m/e: 280.10 (M+1).

Example 7

Benzofuran-2-carboxylic acid (6-cyanopyridin-3-yl)amide

To a suspension of sodium hydride (0.184 g, 7.6 mmol) in dry dimethyl formamide (20 mL), a solution of salicylaldehyde (0.947 g, 7.6 mmol) in dry dimethylformamide (20 mL) was added dropwise under stirring. Stirring was continued for 30 minutes, and compound of example 3 (1.5 g, 7.6 mmol) was added to the reaction mixture and heated at 80° C. for 2 hours. To this reaction mixture was added a solution of sodium methoxide (0.044 g) and stirred for 1 hour at 80° C. The reaction mixture was cooled, diluted with water and extracted with chloroform (3×100 mL). Chloroform layer was dried over sodium sulfate and concentrated. The crude product was purified using repetitive column chromatography (silica gel, ethyl acetate/petroleum ether followed by chloroform as an eluent) to obtain the title compound.

Yield: 0.035 g (2%); $^1$H NMR (DMSO-$d_6$, 300 MHz): δ 7.19-7.24 (m, 1H), 7.50-7.52 (d, 1H), 7.59-7.69 (m, 2H), 7.84-7.87 (d, 2H), 8.55 (s, 1H), 9.82 (s, 1H), 10.05 (s, 1H); MS m/e: 262.02 (M−1).

Example 8

2-Chloro-N-(6-cyanopyridin-3-yl)propionamide

Triethylamine (0.635 g, 6.3 mmol) was added to a suspension of 5-amino-2-cyano-pyridine (0.500 g, 4.2 mmol) in dry dichloromethane (10 mL) under stirring at 0° C. To this, 2-chloropropionyl chloride (0.800 g, 6.3 mmol) was added dropwise and the reaction mixture was stirred at 0° C. for 1 hour and then at room temperature for 3 hours. Reaction mixture was diluted with dichloromethane (50 mL) and was washed with saturated sodium bicarbonate solution (50 mL) and water (50 mL). The organic layer was dried over anhydrous sodium sulfate and concentrated. The crude product obtained was purified using column chromatography (silica gel, 30% ethyl acetate in petroleum ether as an eluent), and further crystallized from ethyl acetate and petroleum ether to obtain the title compound.

Yield: 0.27 g (30%); $^1$H NMR (DMSO-$d_6$, 300 MHz): δ 1.60-1.62 (d, 3H), 4.67-4.73 (m, 1H), 7.99-8.01 (d, 1H), 8.25-8.29 (m, 1H), 8.86 (s, 1H), 10.99 (s, 1H); MS m/e: 210.04 (M+1).

Example 9

2-Chloro-N-[6-(N-hydroxycarbamimidoyl)pyridine-3-yl]propionamide

To a solution of potassium hydroxide (0.048 g, 0.64 mmol) in dry methanol (20 mL) was added hydroxylamine hydrochloride (0.049 g, 0.64 mmol) and the mixture was stirred for 30 minutes. White precipitate of potassium chloride obtained was filtered and to the filtrate was added compound of example 8 (0.1 g, 0.48 mmol) and the reaction mixture was stirred at reflux temperature for 3.5 hours. The reaction mixture was then cooled, concentrated and the crude product obtained was triturated with diethyl ether to obtain the title compound.

Yield: 0.105 g (91%); $^1$H NMR (DMSO-$d_6$, 300 MHz): δ 1.59-1.62 (d, 3H), 4.72-4.79 (m, 1H), 5.77 (s, 2H) 7.79-7.82 (d, 1H), 8.03-8.07 (m, 1H), 8.79 (s, 1H), 9.83 (s, 1H), 10.88 (s, 1H); MS m/e: 241.05 (M−1).

Example 10

2,2-Dichloro-N-(6-cyanopyridin-3-yl)acetamide

5-Amino-2-cyanopyridine (0.500 g, 4.2 mmol) was suspended in dry dichloromethane (10 mL) and triethylamine (0.635 g, 6.3 mmol) was added to it under stirring at 0° C. To the reaction mixture 2,2-dichloroacetyl chloride (0.800 g, 6.3 mmol) was added dropwise under stirring at 0° C. and stirring was further continued for about 10 minutes at about 0° C. and then at room temperature for 4 hours. The reaction mixture was diluted with dichloromethane (50 mL) and washed with saturated sodium bicarbonate solution (50 mL) and water (50 mL). The organic layer was dried over anhydrous sodium sulfate and concentrated. The crude product was purified using column chromatography (silica gel, 30% ethyl acetate in petroleum ether as an eluent) and further crystallized from ethyl acetate and petroleum ether to obtain the title compound.

Yield: 0.170 g (18%); $^1$H NMR (DMSO-$d_6$, 300 MHz): δ 6.67 (s, 1H), 8.02-8.05 (d, 1H), 8.25-8.29 (m, 1H), 8.87 (s, 1H), 11.33 (s, 1H); MS m/e: 227.97 (M−1).

Example 11

2,2-Dichloro-N-[6-(N-hydroxycarbamimidoyl)-pyridin-3-yl]-acetamide

To a solution of potassium hydroxide (0.048 g, 0.64 mmol) in dry methanol (20 mL) was added hydroxylamine hydrochloride (0.049 g, 0.64 mmol) and the mixture was stirred for 30 minutes. White precipitate of potassium chloride obtained was filtered and to the filtrate was added compound of example 10 (0.10 g, 0.44 mmol) and the reaction mixture was stirred at reflux temperature for 3.5 hours. The reaction mixture was cooled, concentrated and the crude product obtained was triturated with diethyl ether to obtain the title compound.

Yield: 0.108 g (94%); $^1$H NMR (DMSO-$d_6$, 300 MHz): δ 5.79 (s, 2H), 6.69 (s, 1H), 7.82-7.85 (d, 1H), 8.05-8.09 (m, 1H), 8.82 (s, 1H), 9.88 (s, 1H), 11.63 (bs, 1H);

MS m/e: 260.99. (M−1).

Example 12

5-Aminopyridine-2-carboxamidine

Dry HCl gas (generated by adding concentrated HCl dropwise in concentrated sulphuric acid), was passed through a solution of 5-amino-2-cyanopyridine (2.5 g, 20.9 mmol) in ethanol (50 mL) till pH of the reaction mixture was 2. The reaction mixture was stirred for 30 minutes, followed by addition of ethanolic ammonia solution till the pH was alkaline and was stirred for 24 hours at room temperature. The reaction mixture was filtered and the residue was washed with ethanol (3×100 mL). The filtrate was combined and ethanol was removed under reduced pressure. The crude product obtained was purified by column chromatography (silica gel, 13% methanol in chloroform as an eluent) to obtain the title compound.

Yield: 2.17 g (95%); $^1$H NMR (DMSO-$d_6$, 500 MHz): δ 6.62 (s, 2H), 7.02 (dd, 1H), 8.074 (m, 2H), 8.88 (s, 2H), 9.06 (s, 1H); MS m/e: 137.083 (M+1).

Example 13

2-(5-Aminopyridin-2-yl)-6-methylpyrimidine-4-ol

To a solution of compound of example 12 (0.4 g, 2.9 mmol) in water (10 mL) and ethanol (5 mL) was added ethylacetoacetate (0.611 g, 4.7 mmol) and sodium carbonate (0.561 g, 5.29 mmol) and mixture was stirred at room temperature for about 25 hours. Ethanol was removed under reduced pressure, and the reaction mixture was diluted with water and extracted with ethyl acetate (3×30 mL). Ethyl acetate layer was dried over anhydrous sodium sulfate and was concentrated to obtain a crude product, which was purified by column chromatography (silica gel, 6% methanol in chloroform as an eluent) to obtain the title compound.

Yield: 0.25 g (42%); $^1$H NMR (DMSO-$d_6$, 500 MHz): δ 2.23 (s, 3H), 6.09 (s, 1H), 6.245 (s, 2H), 7.043 (d, 1H), 8.016 (d, 2H), 11.217 (s, 1H); MS m/e: 203.09 (M+1).

Example 14

2-Chloro-N-(6-(4-hydroxy-6-methylpyrimidin-2-yl) pyridin-3-yl)acetamide

To a solution of compound of example 13 (0.10 g, 0.49 mmol) in THF (5 mL) was added triethylamine (0.075 g, 0.742 mmol) and chloroacetylchloride (0.0559 g, 0.495 mmol), and the reaction mixture was stirred at room temperature for 2 hours. THF was removed under reduced pressure, and the reaction mixture was quenched with water and extracted with ethyl acetate (3×10 mL). The organic layer was dried over anhydrous sodium sulfate and concentrated to obtain the crude product, which was purified by crystallization from ethyl acetate and petroleum ether to obtain the title compound.

Yield: 0.0627 g (45%); $^1$H NMR (CD$_3$OD, 300 MHz): δ 2.392 (s, 3H), 4.26 (S, 2H), 6.29 (s, 1H), 8.31 (dd, 1H), 8.433 (d, 1H), 8.967 (d, 1H); MS m/e: 277.1 (M−1).

Example 15

2-(5-Aminopyridin-2-yl)-6-(trifluoromethyl)pyrimidin-4-ol

To a solution of compound of example 12 (0.1 g, 0.73 mmol) in water (5 mL) and ethanol (2.5 mL) was added ethyl-4,4,4-trifluoroacetoacetate (0.216 g, 1.17 mmol) and sodium carbonate (0.140 g, 1.32 mmol) at room temperature, and the reaction mixture was stirred for about 24 hours. Ethanol was removed under reduced pressure, and the reaction mixture was diluted with water and extracted with ethyl acetate (3×10 mL). The organic layer was dried over anhydrous sodium sulfate and concentrated to obtain the crude product, which was purified by column chromatography (silica gel, 1% methanol in chloroform as an eluent) to obtain the title compound.

Yield: 0.047 g (25%); $^1$H NMR (CD$_3$OD, 300 MHz): δ 6.650 (s, 1H), 7.088 (dd, 1H), 8.151 (m, 2H); MS m/e: 255.04 (M−1).

Example 16

2-(5-Aminopyridin-2-yl)-5-chloro-6-methylpyrimidin-4-ol

To a solution of compound of example 12 (0.05 g, 0.36 mmol) in water (2 mL) and ethanol (1 mL) was added ethyl-2-chloroacetoacetate (0.096 g, 0.58 mmol) and sodium carbonate (0.070 g, 0.66 mmol) and the reaction mixture was stirred at room temperature for 26 hours. Ethanol was removed under reduced pressure, and the reaction mixture was diluted with water and extracted with ethyl acetate. The organic layer was dried over anhydrous sodium sulfate and concentrated to obtain the crude product, which was purified by column chromatography (silica gel, 1% methanol in chloroform as an eluent) to obtain the title compound.

Yield: 0.017 g (19%); $^1$H NMR (DMSO-$d_6$, 500 MHz): δ 2.401 (s, 3H), 6.266 (s, 2H), 7.042 (d, 1H), 7.959-8.026 (m, 2H), 11.97 (s, 1H); MS m/e: 235.04 (M−1).

Example 17

2-Chloro-N-(5-cyanopyridin-3-yl)acetamide

To a suspension of 2-amino-5-cyanopyridine (2.0 g, 16.8 mmol) in dry chloroform (40 mL) was added triethylamine (2.54 g, 25.21 mmol) with stirring at 0° C. To the reaction mixture chloroacetyl chloride (2.08 g, 18.48 mmol) was added dropwise, and stirred at 0° C. for 1 hour and then at room temperature for 12 hours. The reaction mixture was diluted with chloroform (100 mL) and washed with water (150 mL). The organic layer was separated, dried over anhydrous sodium sulfate and concentrated under reduced pressure. The product was recrystallized from chloroform and petroleum ether to obtain the title compound.

Yield: 2.15 g (65%); $^1$H NMR (DMSO-$d_6$, 300 MHz): δ 4.39 (s, 2H), 8.17-8.18 (d, 1H), 8.27-8.29 (m, 1H), 8.8 (s, 1H), 11.32 (s, 1H); MS m/e: 195.96 (M+1).

Example 18

2-Chloro-N-[5-(N-hydroxycarbamimidoyl)pyridin-2-yl]acetamide

To a solution of potassium hydroxide (0.336 g, 5.1 mmol) in dry methanol (20 mL) was added hydroxylamine hydrochloride (0.355 g, 5.1 mmol) and the mixture was stirred for 30 minutes. White precipitate of potassium chloride obtained was filtered and to the filtrate was added compound of example 17 (1.0 g, 5.1 mmol) and the reaction mixture was stirred at reflux temperature for 6 hours. The reaction mixture was then concentrated and the crude product obtained was triturated with diethyl ether to obtain the title compound.

Yield: 0.410 g (35%); $^1$H NMR (DMSO-$d_6$, 300 MHz): δ 4.34 (s, 2H), 5.92 (s, 2H), 8.03 (s, 2H), 8.59 (s, 1H), 9.72 (s, 1H), 10.91(s, 1H); MS m/e: 229.04 (M+1).

Example 19

N-(5-cyanopyridin-2-yl)-2-morpholinoacetamide

Compound of example 17 (0.100 g, 0.44 mmol) was stirred in morpholine (1 mL) at room temperature for about 4 hours. The reaction mixture was concentrated and the crude product was purified using column chromatography (silica gel, 1% methanol in chloroform as an eluent) to obtain the title compound.

Yield: 0.071 g (56%); $^1$H NMR (DMSO-D$_6$, 500 MHZ): δ 2.52 (bt, 4H), 3.24 (s, 2H), 3.60 (bt, 4H), 8.20-8.22 (m, 1H), 8.25-8.27 (m, 1H), 8.78 (s, 1H), 10.50 (bs, 1H); MS m/e: 245.1 (M−1).

Example 20

2-(Benzyloxyamino)-N-(5-cyanopyridyl-2-yl)acetamide

To a solution of potassium hydroxide (0.066 g, 1.0 mmol) in dry methanol (20 mL) was added o-benzylhydroxylamine hydrochloride (0.159 g, 1.0 mmol) and the mixture was stirred for 30 minutes. White precipitate of potassium chloride obtained was filtered and to the filtrate was added compound of example 17 (0.195 g, 1.0 mmol) and the reaction mixture was stirred at reflux temperature for 6 hours. The reaction mixture was cooled, concentrated and purified over silica gel column using methanol/chloroform as an eluent to obtain the title compound.

Yield: 0.048 g (17%); $^1$H NMR (DMSO-$d_6$, 300 MHz): δ 3.62-3.64 (d, 2H), 4.65 (s, 2H), 7.04-7.08 (m, 1H), 7.24-7.29 (m, 4H), 7.96-7.97 (d, 1H), 8.27-8.30 (d, 1H), 8.86 (s, 1H), 10.56 (s, 1H); MS m/e: 281.1 (M−1).

Example 21

3-Chloro-N-[6-(N-hydroxycarbamimidoyl)pyridin-3-yl]propionamide

To a suspension of 5-amino-2-cyanopyridine (1.00 g, 8.4 mmol) in dry dichloromethane (10 mL) was added triethylamine (1.27 g, 12.6 mmol) and the reaction mixture was stirred at 0° C. To the reaction mixture 3-chloropropionyl chloride (1.42 g, 12.6 mmol) was added drop wise over a period of 15 minutes, and the reaction mixture was stirred at 0° C. for 1 hour and then at room temperature for 4 hours. The reaction mixture was diluted with dichloromethane (50 mL) and washed with saturated sodium bicarbonate solution (50 mL) and water (50 mL). The organic layer was dried over anhydrous sodium sulfate and concentrated to obtain the crude product, which was purified over silica gel using methanol/chloroform as eluent. The pure fraction was concentrated to obtain 3-chloro-N-(6-cyanopyridin-3-yl)propionamide. To a solution of potassium hydroxide (0.1 g, 1.5 mmol) in dry methanol (20 mL) was added hydroxylamine hydrochloride (0.105 g, 1.5 mmol) and the mixture was stirred for 30 minutes. White precipitate of potassium chloride obtained was filtered and to the filtrate was added 3-chloro-N-(6-cyanopyridin-3-yl)propionamide (0.209 g, 1.0 mmol) as obtained herein above, and the reaction mixture was stirred at reflux temperature for 4 hours. The reaction mixture was then concentrated and the crude product obtained was triturated with diethyl ether to obtain a solid which was crystallized from ethyl acetate/petroleum ether to obtain the title compound.

Yield: 0.090 g (37%); $^1$H NMR (DMSO-$d_6$, 300 MHz): δ 2.83-2.87 (t, 2H), 3.85-3.89 (t, 2H), 5.77 (s, 2H) 7.78-7.80 (d, 1H), 8.00-8.04 (m, 1H), 8.74 (s, 1H), 9.80 (s, 1H), 10.42 (s, 1H); MS m/e: 243.05 (M+1).

Example 22

2-Chloro-N-(5-cyanopyridin-2-yl)propionamide

To a suspension of 2-amino-5-cyanopyridine (0.500 g, 4.2 mmol) in dry dichloromethane (20 mL) was added triethylamine (0.830 g, 6.3 mmol) and the mixture was stirred at 0° C. To the reaction mixture, 2-chloropropionyl chloride (0.800 g, 6.3 mmol) was added dropwise, and the reaction mixture was stirred at 0° C. for an hour and then at room temperature for 48 hours. The reaction mixture was diluted with dichloromethane (100 mL) and was washed with water (150 mL). The reaction mixture was dried over anhydrous sodium sulfate and concentrated to obtain the crude product, which was purified by column chromatography (silica gel, 15-20% ethyl acetate in petroleum ether as an eluent) to obtain the title compound.

Yield: 0.305 g (35%); $^1$H NMR (DMSO-$d_6$, 300 MHz): δ 1.57-1.59 (d, 3H), 4.80-4.86 (m, 1H), 8.18-8.20 (d, 1H), 8.26-8.30 (m, 1H), 8.8 (s, 1H), 11.37 (s, 1H).

Example 23

2-Chloro-N-[5-(N-hydroxycarbamimidoyl)pyridin-2-yl]propionamide

To a solution of potassium hydroxide (0.10 g, 1.5 mmol) in dry methanol (20 mL) was added hydroxylamine hydrochloride (0.104 g, 1.5 mmol) and the mixture was stirred for 30 minutes. White precipitate of potassium chloride obtained was filtered and to the filtrate was added compound of example 22 (0.209 g, 1.0 mmol) and the reaction mixture was stirred at reflux temperature for 3 hours. The reaction mixture was then concentrated and the crude product obtained was triturated with diethyl ether to obtain the title compound.

Yield: 0.085 g (35%); $^1$H NMR (DMSO-$d_6$, 300 MHz): S 1.59-1.62 (d, 3H), 4.85-4.88 (m, 1H), 5.94 (s, 2H), 8.06 (s, 2H), 8.63 (s, 1H), 9.75 (s, 1H), 11.00 (s, 1H); MS m/e: 243.05 (M+1).

Example 24

2,2-Dichloro-N-(5-cyanopyridin-2-yl)acetamide

To a suspension of 2-amino-5-cyanopyridine (0.500 g, 4.2 mmol) in dry dichloromethane (20 mL) was added triethylamine (0.830 g, 6.3 mmol) and the mixture stirred at 0° C. To the reaction mixture 2,2-dichloroacetyl chloride (0.923 g, 6.3 mmol) was added dropwise and the mixture was stirred at 0° C. for about 1 hour and then at room temperature for 48 hours. The reaction mixture was diluted with dichloromethane (100 mL) and washed with water (150 mL). The organic layer was dried over anhydrous sodium sulfate and concentrated to obtain the crude product, which was purified by column chromatography (silica gel, 25-30% ethyl acetate in petroleum ether as an eluent) to obtain the title compound.

Yield: 0.305 g (35%); $^1$H NMR (DMSO-$d_6$, 300 MHz): δ 6.7 (s, 1H), 8.18-8.20 (d, 1H), 8.35-8.37(d, 1H), 8.87 (s, 1H); MS m/e: 229.05 (M−1).

Example 25

N-(6-cyanopyridin-3-yl)thiophene-2-carboxamide (compound 25a) and N-(6-cyanopyridin-3-yl)-N-(thiophene-2-carbonyl)thiophene-2-carboxamide (compound 25b)

To a suspension of 5-amino-2-cyanopyridine (2.00 g, 16.8 mmol) in dry dichloromethane (50 mL) was added triethylamine (2.54 g, 25.21 mmol) and the mixture was stirred at 0° C. To the reaction mixture 2-thiophene carbonyl chloride (3.70 g, 25.21 mmol) was added drop wise over a period of 15 minutes, and the reaction mixture was stirred at 0° C. for about 1 hour and then at room temperature overnight. The reaction mixture was diluted with dichloromethane (50 mL) and washed with saturated sodium bicarbonate solution (50 mL) and water (50 mL). The organic layer was dried over anhydrous sodium sulfate and concentrated to obtain the crude product, which was purified by column chromatography (silica gel, 20-50% ethyl acetate in petroleum ether as an eluent) to obtain N-(6-cyanopyridin-3-yl)thiophene-2-carboxamide (compound 25a) Yield: 0.430 g (7.74%) and N-(6-cyanopyridin-3-yl)-N-(thiophene-2-carbonyl)thiophene-2-carboxamide (compound 25b). Yield: 1.3 g (33.75%).

Compound 25a $^1$H NMR (DMSO-$d_6$, 300 MHz): δ 7.25-7.28 (m, 1H), 7.94-7.95 (d, 1H), 8.00-8.06 (m, 2H), 8.36-8.40 (dd, 1H), 9.03 (s, 1H), 10.80 (s, 1H); MS m/e: 230 (M+1).

Compound 25b $^1$H NMR (DMSO-d$_6$, 300 MHz): δ 7.13-7.16 (t, 2H) 7.60-7.62 (dd, 2H), 8.01-8.03 (dd, 2H), 8.11-8.12 (d, 2H), 8.8 (s, 1H); MS m/e: 340 (M+1);

Example 26

N-(6-(N'-hydroxycarbamimidoyl)pyridin-3-yl) thiophene-2-carboxamide

To a solution of potassium hydroxide (0.10 g, 1.5 mmol) in dry methanol (20 mL) was added hydroxylamine hydrochloride (0.104 g, 1.5 mmol) and the mixture was stirred for 30 minutes. White precipitate of potassium chloride obtained was filtered and to the filtrate was added N-(6-cyanopyridin-3-yl)-N-(thiophene-2-carbonyl)thiophene-2-carboxamide (0.229 g, 1.0 mmol) and the reaction mixture was stirred at reflux temperature for 6 hours. The reaction mixture was then concentrated and the crude product obtained was triturated with diethyl ether to obtain the title compound.

Yield: 0.085 g (35%); $^1$H NMR (DMSO-d$_6$, 500 MHz): δ 5.81 (s, 2H), 7.25-7.27 (m, 1H), 7.84-7.92 (dd, 2H) 8.08-8.10 (d, 1H), 8.16-8.18 (d, 1H), 8.93 (s, 1H), 9.84 (s, 1H), 10.6 (s, 1H); MS m/e: 263.05 (M+1).

Example 27

N-(6-cyanopyridin-3-yl)-2-phenylacetamide

To a suspension of 5-amino-2-cyanopyridine (0.500 g, 4.2 mmol) in dry dichloromethane (20 mL) was added triethylamine (0.637 g, 6.3 mmol) and the mixture was stirred at 0° C. To the reaction mixture phenylacetyl chloride (0.973 g, 6.3 mmol) was added dropwise and stirred at 0° C. for 1 hour and then at room temperature for 24 hours. The reaction mixture was diluted with chloroform (100 mL) and washed with water (150 mL). The organic layer was dried over anhydrous sodium sulfate and concentrated to obtain the crude product, which was purified using column chromatography (silica gel, 20% ethyl acetate in petroleum ether as an eluent) to obtain the title compound.

Yield: 0.358 g (36%); $^1$H NMR (DMSO-d$_6$, 500 MHz): δ 3.74 (s, 2H), 7.25-7.28 (m, 1H), 7.33-7.34 (m, 4H), 7.97-7.99 (d, 1H), 8.26-8.28 (dd, 1H), 8.87 (s, 1H), 10.86 (s, 1H); MS m/e: 236 (M−1).

Example 28

N-[6-(N'-hydroxycarbamimidoyl)pyridin-3-yl]-2-phenylacetamide

To a solution of potassium hydroxide (0.10 g, 1.5 mmol) in dry methanol (20 mL) was added hydroxylamine hydrochloride (0.105 g, 1.5 mmol) and the mixture was stirred for 30 minutes. White precipitate of potassium chloride obtained was filtered and to the filtrate was added compound of example 27 (0.237 g, 1.0 mmol) and the reaction mixture was stirred at reflux temperature for 3 hours. The reaction mixture was then cooled to obtain the title compound.

Yield: 0.170 g (63%); $^1$H NMR (DMSO-D$_6$, 500 MHZ): δ 3.70 (s, 2H), 5.77 (s, 2H), 7.25 (m, 1H), 7.33-7.34 (m, 4H), 7.79-7.81 (d, 1H), 8.03-8.04 (m, 1H), 8.77 (s, 1H), 9.80 (s, 1H), 10.51 (s, 1H); MS m/e: 271 (M+1).

Example 29

2-Chloro-N-[6-(5-(trifluoromethyl)-1,2,4-oxadiazol-3-yl)pyridin-3-yl]acetamide

Compound of example 4'(1.2 g, 5.25 mmol) was refluxed in trifluoroacetic anhydride at a temperature in the range of 45-50° C. for 2 hours. The reaction mixture was cooled, diluted with water, basified with ammonia solution, and extracted with ethyl acetate (3×100 mL). The organic layer was washed with brine, dried over sodium sulfate and concentrated. The crude product obtained was purified over silica gel using ethyl acetate/petroleum ether (25% -50%) as an eluent. Pure fractions were concentrated and crystallized using chloroform/petroleum ether, to obtain the title compound.

Yield: 1.3 g (80%); $^1$H NMR (DMSO-d$_6$, 300 MHz): δ 4.35 (s, 2H), 8.14-8.17 (d, 1H), 8.32-8.36 (dd, 1H), 8.90 (s, 1H), 10.91 (s, 1H); MS m/e: 305 (M−1).

Example 30

2-Chloro-N-[6-(5-methyl-1,2,4-oxadiazol-3-yl)pyridin-3-yl]acetamide

Compound of example 4 (5.5 g, 24 mmol) was refluxed in acetic anhydride (10 mL) at a temperature in the range of 115-120° C. for 2 hours. The black colored reaction mixture was cooled, diluted with water, basified with ammonia solution, and extracted with ethyl acetate (3×100 mL). The organic layer was washed with brine, dried over sodium sulfate and concentrated. The crude product obtained was purified over silica gel using ethyl acetate/petroleum ether (25%-50%) as eluent and the semipurified fractions were further purified using methanol/chloroform (0.5% -1%) as eluent. Pure fractions were concentrated and crystallized using chloroform/petroleum ether, to obtain the title compound.

Yield: 2.16 g (35%); $^1$H NMR (DMSO-d$_6$, 300 MHz): δ 2.65 (s, 3H), 4.33(s, 2H), 8.02-8.05 (d, 1H), 8.24-8.28 (dd, 1H), 8.84 (s, 1H), 10.81 (s, 1H); MS m/e: 253 (M+1).

Example 31

3-(3-(5-(2-Chloroacetamido)pyridin-2-yl)-1,2,4-oxadiazol-5-yl)propanoic acid

A mixture of compound of example 4 (0.228 g, 1 mmol) and succinic anhydride was stirred in dimethyl formamide (5 mL), at a temperature in the range of 115-120° C. for a period of 16 hours. The reaction mixture was cooled, diluted with water, and extracted with ethyl acetate (3×50 mL). The organic layer was washed with brine, dried over sodium sulfate and concentrated. The crude product obtained was purified over silica gel using ethyl acetate as eluent. The pure fractions were concentrated and crystallized using ethyl acetate/petroleum ether, to obtain the title compound.

Yield: 0.109 g (35%); $^1$H NMR (DMSO-d$_6$, 300 MHz): δ 2.80-2.85 (t, 2H), 3.15-3.20 (t, 2H), 4.33(s, 2H), 8.02-8.05 (d, 1H), 8.25-8.29 (dd, 1H), 8.84 (s, 1H), 10.82 (s, 1H), 12.45 (s,1H); MS m/e: 309 (M−1).

Example 32

2-Chloro-N-(6-cyanopyridin-3-yl)-2-phenylacetamide

To a suspension of 5-amino-2-cyanopyridine (0.500 g, 4.2 mmol) in dry dichloromethane (20 mL) was added triethylamine (0.637 g, 6.3 mmol) and the mixture was stirred at 0° C. α-Chloro phenylacetyl chloride (0.952 g, 5.04 mmol) was added dropwise to the mixture, and the reaction mixture was stirred at room temperature for 24 hours. The reaction mixture was diluted with chloroform (100 mL) and washed with water (150 mL). The organic layer was dried over anhydrous sodium sulfate and concentrated to obtain the crude product, which was purified by column chromatography (silica gel and ethyl acetate (20%) in petroleum ether as an eluent) to obtain the title compound.

Yield: 0.210 g (18%); $^1$H NMR (DMSO-$d_6$, 500 MHz): δ 5.80 (s, 1H), 7.39-7.42 (m, 3H), 7.55-7.58 (m, 2H), 7.98-8.00 (d, 1H), 8.24-8.28 (dd, 1H), 8.85 (s, 1H), 11.14 (s, 1H); MS m/e: 271 (M+1).

Example 33

2-Chloro-N-[6-(N'-hydroxycarbamimidoyl)pyridine-3-yl]-2-phenylacetamide

To a solution of potassium hydroxide (0.036 g, 0.552 mmol) in dry methanol (20 mL) was added hydroxylamine hydrochloride (0.038 g, 0.552 mmol) and the mixture was stirred for 30 minutes. The white precipitate of potassium chloride obtained was filtered and to the filtrate was added compound of example 32 (0.100 g, 0.368 mmol). The mixture was stirred at reflux temperature for 4 hours. The reaction mixture was cooled to obtain white shiny title compound.

Yield: 0.105 g (93%); $^1$H NMR (DMSO-$d_6$, 500 MHz): δ 5.77 (s, 2H), 5.81 (s, 1H), 7.35-7.44 (m, 3H), 7.57-7.60 (m, 2H), 7.79-7.82 (d, 1H), 8.01-8.04 (dd, 1H), 8.75 (s, 1H), 9.83 (s, 1H), 10.92 (s, 1H); MS m/e; 305 (M+1).

Example 34

2-Chloro-N-(6-cyanopyridin-3-yl)-2,2-difluoroacetamide

To a suspension of 5-amino-2-cyanopyridine (1.0 g, 8.4 mmol) in dry DMF (20 mL) was added sodium hydride (0.336 g, 8.4 mmol) slowly in small lots over a period of 15 minutes, followed by dropwise addition of 2-chloro-2,2-difluoroacetic anhydride (2.04 g, 8.4 mmol). The reaction mixture was stirred at room temperature for 24 hours. The reaction mixture was diluted with water (150 mL) and extracted with ethyl acetate (3×100 ml). The organic layer was washed with brine, dried over anhydrous sodium sulfate and was concentrated to obtain the title compound.

Yield: 1.6 g (82%); $^1$H NMR (DMSO-$d_6$, 300 MHz): δ 8.07-8.09 (d, 1H), 8.30-8.34 (dd, 1H), 8.98 (s, 1H), 11.77 (s, 1H); MS m/e: 232 (M+1).

Example 35

2-Chloro-2,2-difluoro-N-[6-(N'-hydroxycarbamimidoyl)pyridine-3-yl]acetamide

To a solution of potassium hydroxide (0.428 g, 6.48 mmol) in dry methanol (40 mL) was added hydroxylamine hydrochloride (0.450 g, 6.48 mmol) and the mixture was stirred for 30 minutes. The white precipitate of potassium chloride obtained was filtered and to the filtrate was added compound of example 34 (1.00 g, 4.32 mmol), and the mixture was stirred at reflux temperature for 4 hours. The reaction mixture was cooled to obtain white fluffy solid as the title compound.

Yield: 0.540 g (93%); $^1$H NMR (DMSO-$d_6$, 500 MHz): δ 5.86 (s, 2H), 7.86-7.89 (d, 1H), 8.02-8.12 (dd, 1H), 8.82-8.83 (d, 1H), 9.94 (s, 1H), 11.47 (s, 1H);
MS m/e: 265 (M+1), 263(M−1).

Example 36

2-Chloro-2,2-difluoro-N-(6-(5-(trifluoromethyl)-1,2,4-oxadiazol-3-yl)pyridin-3-yl)acetamide To a solution of compound of example 35 (0.125 g, 0.47 mmol) in dry THF (10 mL) was added trifluoroacetic anhydride (0.297 g, 1.417 mmol) and the mixture was heated at 50° C. for 2 hours. The reaction mixture was concentrated, diluted with water, basified with ammonia solution, and extracted with ethyl acetate (3×50 mL). The organic layer was washed with brine, dried over sodium sulfate and concentrated. The crude product obtained was purified over silica gel using ethyl acetate/petroleum ether (20%) as eluent, and the pure fractions were concentrated and crystallized using chloroform/petroleum ether to obtain the title compound.

Yield: 0.085 g (52%); $^1$H NMR (DMSO-$d_6$, 300 MHz): δ 8.20-8.23 (d, 1H), 8.38-8.41 (dd, 1H), 9.04 (s, 1H), 11.73 (s, 1H); MS m/e: 343(M+1), 365 (M+23).

Example 37

2-Chloro-N-(6-cyanopyridin-3-yl)-2-fluoroacetamide

To a suspension of 5-amino-2-cyano-pyridine (0.478 g, 4.0 mmol) in dry DMF (20 mL) was added sodium hydride (0.160 g, 4.0 mmol) slowly in small lots over a period of 15 minutes, followed by dropwise addition of ethyl-2-chloro-2-fluoro acetate (0.562 g, 4.0 mmol). The reaction mixture was stirred at room temperature for a period of 4 hours and further at 60° C. for 8 hours. The reaction mixture was diluted with water (100 mL) and extracted with ethyl acetate (3×100 mL). The organic layer was washed with brine, dried over anhydrous sodium sulfate and concentrated to obtain the crude product which was purified over silica gel column using ethyl acetate/petroleum ether (15%-30%) as an eluent to obtain the title compound.

Yield: 0.408 g (47%); $^1$H NMR (DMSO-$d_6$, 500 MHz): δ 6.87-7.04 (d, 1H), 8.03-8.05 (d, 1H), 8.28-8.32 (dd, 1H), 8.92-8.93 (d, 1H), 11.31 (s, 1H); MS m/e: 212 (M−1).

Example 38

2-Chloro-2-fluoro-N-[6-(N'-hydroxycarbamimidoyl)pyridin-3-yl]acetamide

To a solution of potassium hydroxide (0.112 g, 1.69 mmol) in dry methanol (20 mL) was added hydroxylamine hydrochloride (0.117 g, 6.48 mmol) and the mixture was stirred for 30 minutes. The white precipitate of potassium chloride obtained was filtered and to the filtrate was added compound of example 37 (0.240 g, 1.12 mmol). The mixture was stirred at reflux temperature for 2 hours. The reaction mixture was cooled, concentrated and triturated with diethyl ether to obtain the title compound.

Yield: 0.260 g (93%); $^1$H NMR (DMSO-$d_6$, 500 MHz): δ 5.79 (s, 2H), 6.88-7.04 (d, 1H), 7.83-7.86 (d, 1H), 8.06-8.10 (dd, 1H), 8.80-8.81(d, 1H), 9.87 (s, 1H), 11.17 (s, 1H); MS m/e: 247 (M+1), 245 (M−1).

Example 39

2-Chloro-2-fluoro-N-(6-(5-(trifluoromethyl)-1,2,4-oxadiazol-3-yl)pyridin-3-yl)acetamide To a solution of compound of example 38 (0.100 g, 0.40 mmol) in dry THF (10 mL) was added trifluoroacetic anhydride (0.255 g, 1.20 mmol) and the reaction mixture was heated at 50° C. for 2 hours. The reaction mixture was concentrated, diluted with water, basified with ammonia solution, and extracted with ethyl acetate (3×50 mL). The organic layer was washed with brine, dried over sodium sulfate and concentrated. The crude product obtained was purified over silica gel using ethyl acetate/petroleum ether (20%) as eluent. The pure fractions were concentrated and crystallized using chloroform/petroleum ether, to obtain the title compound.

Yield: 0.080 g (61%); $^1$H NMR (DMSO-$d_6$, 300 MHz): δ 6.88-7.04 (d, 1H), 8.17-8.20 (d, 1H), 8.37-8.40 (dd, 1H), 8.98-8.99 (d, 1H), 11.25 (s, 1H); MS m/e: 325 (M+1), 347 (M+23).

Example 40

2-Chloro-N-[6-(5-(chloromethyl)-1,2,4-oxadiazol-3-yl)pyridin-3-yl]acetamide

Compound of example 4 (0.500 g, 2.18 mmol) was heated in chloroacetyl chloride (2 mL) at a temperature in the range of 100-110° C. for 4 hours. The reaction mixture was cooled, poured over ice water, basified With ammonia solution, and extracted with ethyl acetate (3×60 mL). The organic layer was washed with brine, dried over sodium sulfate and concentrated. The crude product obtained was purified over silica gel using ethyl acetate/petroleum ether (35%-50%) as eluent, and the pure fractions were concentrated and crystallized using chloroform/ petroleum ether, to obtain the title compound.

Yield: 0.040 g (7%); $^1$H NMR (DMSO-$d_6$, 500 MHz): δ 4.34 (s, 2H), 5.18 (s, 2H), 8.06-8.09 (d, 1H), 8.28-8.31 (m, 1H), 8.87 (s, 1H), 10.85 (s, 1H); MS m/e: 287.0 (M+1), 309 (M+23).

Example 41

2-Chloro-N-[6-(5-(chlorodifluoromethyl)-1,2,4-oxadiazol-3-yl)pyridin-3-yl]acetamide (compound 41a) and 2-Chloro-N-[6-(5-(chlorodifluoromethyl)-1,2,4-oxadiazol-3-yl)pyridin-3-yl]-2,2-difluoroacetamide (compound 41b)

Compound of example 4 (0.457 g, 2.00 mmol) was suspended in chlorodifluoroacetic anhydride (3 mL) at a temperature in the range of 100-110° C. for a period of 2 hours. The reaction mixture was cooled, poured over crushed ice, basified with ammonia solution, and extracted with ethyl acetate (3×70 mL). The organic layer was washed with brine, dried over sodium sulfate and concentrated. The crude product obtained was purified over silica gel using ethyl acetate/ petroleum ether (25%-50%) as eluent. The pure fractions were concentrated and crystallized using chloroform/petroleum ether, to obtain 2-chloro-N-[6-(5-(chlorodifluoromethyl)-1,2,4-oxadiazol-3-yl)pyridin-3-yl]acetamide (compound 41a) Yield: 0.150 g (23%) and 2-Chloro-N-[6-(5-(chlorodifluoromethyl)-1,2,4-oxadiazol-3-yl)pyridin-3-yl]-2,2-difluoroacetamide (compound 41b) Yield: 0.170 g (24%).

Compound 41a
$^1$H NMR (DMSO-$d_6$, 300 MHz): δ 4.35 (s, 2H), 8.13-8.16 (d, 1H), 8.32-8.36 (dd, 1H), 8.90 (s, 1H), 10.90 (s, 1H); MS m/e: 321 (M−1), 323 (M+1).

Compound 41b
$^1$H NMR (DMSO-$d_6$, 300 MHz): δ 8.19-8.22 (m, 1H), 8.37-8.8.41 (m, 1H), 9.04- (bs, 1H), 11.72 (s, 1H); MS m/e: 359 (M+1), 357 (M−1).

Example 42

Ethyl 2-(5-(2-chloroacetamido)pyridin-2yl)-5,6-dihydroxypyrimidine-4-carboxylate A mixture of compound of example 4 (2.0 g, 8.75 mmol) and diethylacetylene dicarboxylate (0.34 g, 2.36 mmol) was stirred in methanol (20 mL) at a temperature in the range of 60-65° C. for 4 hours. Methanol was removed under reduced pressure and xylene (20 mL) was added and the reaction mixture was heated at a temperature in the range of 140-145° C. for 18 hours. A brownish colored solid obtained was removed by filtration, and the reaction mixture was again stirred at the same temperature for 8 hours to obtain the title compound.

Yield: 1.40 (45%); $^1$H NMR (DMSO-$d_6$, 300 MHz): δ 1.28-1.33 (t, 3H), 4.28-4.38 (m, 4H), 8.18-8.23 (m, 2H), 8.89 (s, 1H), 10.61 (s, 1H), 10.85 (s, 1H), 12.52 (s, 1H); MS m/e: 351 (M−1).

Example 43

N-(6-carbamimidoylpyridin-3-yl)-2-chloroacetamide

To a solution of compound of example 18 (0.2 g, 0.87 mmol) in acetic acid was added acetic anhydride (0.133 g, 0.73 mmol) and stirred at 25° C. for 5 minutes. To the reaction mixture was added 10% Pd/C (0.028 g) and shaken with hydrogen on Parr hydrogenation apparatus at a pressure of about 15 psi for 4 hours. The reaction mixture was filtered through celite and the filter pad was washed with glacial acetic acid (15 mL). The filtrate was combined, acid removed under reduce pressure, and traces of acid were removed using petroleum ether. The solid obtained was purified by column chromatography using silica gel and 10% methanol/chloroform as an eluent to obtain the title compound.

Yield 0.11 g (59%); $^1$H NMR (DMSO-$d_6$, 500 MHz) δ 4.418 (s, 2H), 8.285-8.302 (d, 1H), 8.342-8.346 (d, 1H), 9.00 (s, 1H), 9.15 (s, 2H), 9.44 (s, 1H), 11.29 (s, 1H); MS m/e: 213.05 (M+1).

Example 44

N-(6-carbamimidoylpyridin-3-yl)acetamide acetate

To a solution of compound of example 1 (0.2 g, 1.32 mmol) in acetic acid was added acetic anhydride (0.202 g, 1.98 mmol) and the reaction mixture was stirred at a temperature of 25° C. for 5 minutes. To the reaction mixture, 10% Pd/C (0.028 g) was added and shaken with hydrogen on Parr hydrogenation apparatus at a pressure of about 15 psi for a period of 4 hours. The reaction mixture was filtered through celite and the filter pad was washed with glacial acetic acid (15 mL). The filtrate was combined and acid removed under reduced pressure. The traces of acid were removed by using petroleum ether and the solid obtained was purified by column chromatography using silica gel and 10% methanol/chloroform as eluent to obtain the title compound.

Yield 0.188 g (80%); $^1$H NMR (D$_2$O, 300 MHz) δ 1.768 (s, 3H), 2.093 (s, 3H), 7.920-7.891 (d, 1H), 8.105-8.076 (dd, 1H), 8.665 (s, 1H); MS m/e: 179 (M+1).

Example 45

N-(6-(5-chloro-4-hydroxy-6-methylpyrimidin-2-yl) pyridin-3-yl)acetamide

To a solution of compound of example 44 (0.01 g, 0.56 mmol) in water (2 mL) and ethanol (1 mL) was added ethyl-2-chloroacetoacetate (0.015 g, 0.89 mmol) and sodium carbonate (0.0107 g, 1.011 mmol). The reaction mixture was stirred at room temperature for a period of 26 hours. Ethanol was removed under reduced pressure, and the reaction mixture was diluted with water and extracted with ethyl acetate. The organic layer was dried over anhydrous sodium sulfate and concentrated to obtain the crude product, which was purified by column chromatography using silica gel and 1% methanol in chloroform as an eluent to obtain the title compound.

Yield: 0.044 g (28%); $^1$H NMR (DMSO-d$_6$, 500 MHz): δ 2.132 (s, 3H), 2.343 (s, 3H), 8.273 (s, 2H), 8.886 (s, 1H), 10.531 (s, 1H), 12.540 (s, 1H); MS m/e (ES−): 278.7 (M+1).

Example 46

N-(6-(4-hydroxy-5,6-dimethylpyrimidin-2-yl)pyridin-3-yl)acetamide

To a solution of compound of example 44 (0.01 g, 0.56 mmol) in water (2 mL) and ethanol (1 mL) was added ethyl 2-methyl-3-oxobutanoate (0.013 g, 0.89 mmol) and sodium carbonate (0.0107 g, 1.011 mmol) and the reaction mixture was stirred at room temperature for 26 hours. Ethanol was removed under reduced pressure, and the reaction mixture was diluted with water and extracted with ethyl acetate. The organic layer was dried over anhydrous sodium sulfate and concentrated to obtain the crude product, which was purified by column chromatography using silica gel and 1% methanol in chloroform as an eluent to obtain the title compound.

Yield: 0.053 g (37%); $^1$H NMR (DMSO-d$_6$, 300 MHz): δ 1.978 (s, 3H), 2.088 (s, 3H), 2.124 (s, 3H) 8.227 (s, 2H), 8.85 (d, 1H), 10.484 (s, 1H), 11.731 (s, 1H); MS m/e: 257.14 (M−1).

Example 47

2-Chloro-N-(6-(5-chloro-4-hydroxy-6-methylpyrimidin-2-yl)pyridin-3-yl)acetamide

To a solution of compound of example 16 (0.10 g, 0.42 mmol) in THF (5 mL), at 0° C. was added triethylamine (0.064 g, 0.63 mmol) and chloroacetylchloride (0.0715 g, 0.63 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography using silica gel and 1% methanol in chloroform as an eluent to obtain the title compound.

Yield: 0.010 g (81%); $^1$H NMR (CD$_3$OD, 300 MHz): δ 2.503 (s, 3H), 4.36 (s, 2H), 8.499 (m, 2H), 8.91 (s, 1H), 10.885 (s, 1H), 12.618 (d, 1H); MS m/e: 312 (M−1).

Example 48

2-(5-aminopyridin-2-yl)-5,6-dimethylpyrimidin-4-ol

To a solution of compound of example 12 (0.2 g, 1.47 mmol) in water (5 mL) and ethanol (2.5 mL) was added ethyl 2-methyl-3-oxobutanoate (0.339 g, 2.35 mmol) and sodium carbonate (0.280 g, 2.64 mmol) at room temperature and the reaction mixture was stirred for 24 hours. Ethanol was removed under reduced pressure, and the reaction mixture was diluted with water and extracted with ethyl acetate (3×20 mL). The organic layer was dried over anhydrous sodium sulfate and concentrated to obtain the crude product, which was purified by column chromatography using silica gel and 1% methanol in chloroform as an eluent to obtain the title compound.

Yield: 0.0130 g (41%); $^1$H NMR (CD$_3$OD, 300 MHz): δ 1.948 (s, 3H), 2.262 (s, 3H), 6.12 (s, 2H), 7.047-7.01 (d, 1H), 7.990-7.961 (d, 2H); MS m/e: 215.08 (M−1).

Example 49

2-(5-Aminopyridin-2-yl)-6-(chloromethyl)pyrimidin-4-ol

To a solution of compound of example 12 (0.2 g, 1.47 mmol) in water (5 mL) and ethanol (2.5 mL) was added ethyl 4-chloroacetoacetate (0.387 g, 2.35 mmol) and sodium carbonate (0.280 g, 2.64 mmol) at room temperature, and the reaction mixture was stirred for about 24 hours. Ethanol was removed under reduced pressure, and the reaction mixture was diluted with water and extracted with ethyl acetate (3×20 mL). The organic layer was dried over anhydrous sodium sulfate and concentrated to obtain the crude product, which was purified by column chromatography using silica gel and 1% methanol in chloroform to obtain the title compound.

Yield: 0.080 g (22%); $^1$H NMR (DMSO-d$_6$, 300 MHz): δ 4.550 (s, 2H),), 6.363-6.279 (m, 3H,), 7.061-7.024 (dd, 1H), 8.029-8.00 (d, 2H), 11.571 (s, 1H); MS m/e: 235.03 (M−1).

Example 50

2-Chloro-N-(6-(4-hydroxy-5,6-dimethylpyrimidin-2-yl)pyridin-3-yl)acetamide

To a solution of compound of example 48 (0.04 g, 0.185 mmol) in THF (4 mL), at 0° C. was added triethylamine (0.028 g, 0.277 mmol) and chloroacetylchloride (0.0313 g, 0.277 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography using silica gel and 1% methanol in chloroform as an eluent to obtain the title compound.

Yield: 0.045 g (83%); $^1$H NMR (DMSO-d$_6$, 300 MHz): δ 1.981 (s, 3H), 2.313 (s, 3H), 4.358 (s, 2H), 8.252-8.216 (dd, 1H), 8.317-8.265 (m, 1H), 8.894-8.890 (d, 1H), 10.848 (s, 1H); MS m/e: 291.05 (M−1).

Example 51

2-Chloro-N-(6-(4-(chloromethyl)-6-hydroxypyrimidin-2-yl)pyridin-3-yl)acetamide

To a solution of compound of example 49 (0.40 g, 0.16 mmol) in THF (4 mL) at 0° C. was added triethylamine (0.025 g, 0.25 mmol) and chloroacetylchloride (0.0285 g, 0.25 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography using silica gel and 1% methanol in chloroform as an eluent to obtain the title compound.

Yield: 0.050 g (94%); $^1$H NMR (DMSO-$d_6$, 500 MHz): δ 4.368 (s, 2H), 4.61 (s, 2H), 6.527 (s, 1H), 8.324-8.266 (m, 2H), 8.936 (s, 1H), 10.901 (s, 1H), 12.201 (s, 1H);

MS m/e: 311 (M−1).

Example 52

2-(5-aminopyridin-2-yl)-5-ethyl-6-methylpyrimidin-4-ol

To a solution of compound of example 12 (0.2 g, 1.47 mmol) in water (5 mL) and ethanol (2.5 mL) was added ethyl-2-ethylacetoacetate (0.379 g, 2.35 mmol) and sodium carbonate (0.280 g, 2.64 mmol) at room temperature and the reaction mixture was stirred for 24 hours. Ethanol was removed under reduced pressure, and the reaction mixture was diluted with water and extracted with ethyl acetate (3×20 mL). The organic layer was dried over anhydrous sodium sulfate and concentrated to obtain the crude product, which was purified by column chromatography using silica gel and 1% methanol in chloroform as an eluent to obtain the title compound.

Yield: 0.039 g (11%); $^1$H NMR (DMSO-$d_6$, 300 MHz): δ 1.034 (t, 3H), 2.281 (s, 3H), 2.472 (q, 2H). 6.149 (s, 2H), 7.046 (m, 1H), 8.500 (m, 2H), 11.234 (s, 1H);

MS m/e: 253.10 (M+Na).

Example 53

2-Chloro-N-(6-(4-hydroxy-6-(trifluoromethyl)pyrimidin-2-yl)pyridin-3-yl)acetamide To a solution of compound of example 15 (0.10 g, 0.39 mmol) in THF (6 mL), at 0° C. was added triethylamine (0.059 g, 0.58 mmol) and chloroacetylchloride (0.066 g, 0.58 mmol), and the reaction mixture was stirred at room temperature for 30 minutes. THF was removed under reduced pressure, and reaction mixture was quenched with water and extracted with ethyl acetate (3×15 mL). The organic layer was dried over anhydrous sodium sulfate and concentrated to obtain the crude product, which was purified by column chromatography using silica gel and 1% methanol in chloroform as an eluent to obtain the title compound.

Yield: 0.112 g (86%); $^1$H NMR (DMSO-$d_6$, 300 MHz): δ 4.374 (s, 2H), 6.907 (s, 1H), 8.347-8.257 (m, 2H), 8.975 (s, 1H), 10.930 (s, 1H), 12.808 (s, 1H); MS m/e: 331.02 (M−1).

Example 54

2-(5-Aminopyridin-2-yl)-5-benzyl-6-methylpyrimidin-4-ol

To a solution of compound of example 12 (0.2 g, 1.47 mmol) in water (5 mL) and ethanol (2.5 mL) was added ethyl 2-benzyl-3-oxobutanoate(0.379 g, 2.35 mmol) and sodium carbonate (0.280 g, 2.64 mmol) at room temperature, and the reaction mixture was stirred for about 24 hours. Ethanol was removed under reduced pressure, and the reaction mixture was diluted with water and extracted with ethyl acetate (3×20 mL). The organic layer was dried over anhydrous sodium sulfate and concentrated to obtain the crude product, which was purified by column chromatography using silica gel and 1% methanol in chloroform as an eluent to obtain the title compound.

Yield: 0.061 g (14%); $^1$H NMR (DMSO-$d_6$, 300 MHz): δ 2.218 (s, 3H), 3.769 (s, 2H), 6.125 (s, 2H), 7.002-6.965 (dd, 1H), 7.237-7.089 (m, 5H), 7.970-7.928 (m, 2H), 11.337 (s, 1H); MS m/e: 293.19 (M +1).

Example 55

6-(4-(allyloxy)-5-chloro-6-methylpyrimidin-2-yl)pyridin-3-amine

To a solution of compound of example 16 (0.275 g, 1.1620 mmol) in DMF (3 mL) at 0° C., was added NaH (0.046 g, 1.1620 mmol) and allyl bromide (0.14 g, 1016 mmol) slowly and the reaction mixture was stirred at 25° C. for 4 hours. DMF was removed under vacuum, and the reaction mass quenched by water, extracted with ethyl acetate (3×20 mL), dried over sodium sulfate and concentrated to obtain the crude product, which was purified by column chromatography using silica gel and 8% methanol in chloroform as an eluent to obtain the title compound.

Yield: 0.110 g (34%); $^1$H NMR (DMSO-$d_6$, 300 MHz): δ 2.363 (s, 3H), 4.841-4.779 (m, 1H), 5.004-4.972 (m, 3H), 5.808-5.717 (m, 1H,), 6.010 (s, 2H), 7.004-6.966 (dd, 1H), 7.553-7.524 (d, 1H), 7.938-7.930 (d, 1H); MS m/e: 275.0 (M+1).

Example 56

N-(6-(4-(allyloxy)-5-chloro-6-methylpyrimidin-2-yl)pyridin-3yl)-2-chloroacetamide To a solution of compound of example 55 (0.064 g, 0.231 mmol) in THF (4 mL), at 0° C. was added triethylamine (0.035 g, 0.346 mmol) and chloroacetylchloride (0.039 g, 0.346 mmol), and the reaction mixture was stirred at room temperature for 30 minutes. THF was removed under reduced pressure, and the reaction mixture was quenched with water and extracted with ethyl acetate (3×10 mL). The organic layer was dried over anhydrous sodium sulfate and concentrated to obtain the crude product, which was purified by column chromatography using silica gel and 1% methanol in chloroform as an eluent to obtain the title compound.

Yield: 0.67 g (82%); $^1$H NMR (DMSO-$d_6$, 300 MHz): δ 2.393 (s, 3H), 4.336 (s, 2H), 4.838 (d, 3H), 5.009 (d, 1H), 5.792-5.682 (m, 1H), 7.800-7.771 (d, 1H), 8.228-8.191 (m, 1H), 8.823-8.816 (d, 1H); MS m/e: 375 (M+Na).

Example 57

6-(4-(allyloxy)-6-(trifluoromethyl)pyrimidin-2-yl)pyridin-3-amine

To a solution of compound of example 15 (0.200 g, 0.78 mmol) in DMF (3 mL), was added $K_2CO_3$ (0.162 g, 1.170 mmol) and the mixture was stirred at 25° C. for 10 minutes, followed by slow addition of allyl bromide (0.14 g, 1.17 mmol). The reaction mixture was stirred at 25° C. for 45 minutes. DMF was removed under vacuum, and the reaction mass quenched by water, extracted with ethyl acetate (3×20 mL), dried over sodium sulfate and concentrated to obtain the crude product, which was purified by column chromatography using silica gel and 5% methanol in chloroform as an eluent to obtain the title compound.

Yield: 0.124 g (53%); $^1$H NMR (DMSO-d$_6$, 300 MHz): δ 5.036-4.846 (m, 4H), 5.847-5.755 (m, 1H), 6.132 (s, 2H), 6.889 (s, 1H), 7.031-6.994 (dd, 1H), 7.619-7.590 (d, 1H), 7.968-7.959 (d, 1H); MS m/e: 296.7 (M+1).

Example 58

6-(4-ethoxy-6-(trifluoromethyl)pyrimidin-2-yl)pyridin-3-amine

To a solution of compound of example 15 (0.100 g, 0.390 mmol) in DMF (3 mL), was added K$_2$CO$_3$ (0.080 g, 0.58 mmol) and stirred at 25° C. for 10 minutes. To the reaction mixture, ethyl iodide (0.0913 g, 0.58 mmol) was added slowly and stirred at 25° C. for 1 hour. DMF was removed under vacuum, and the reaction mass was quenched by water, extracted with ethyl acetate (3×10 mL), dried over sodium sulfate and concentrated to obtain the crude product, which was purified by column chromatography using silica gel and 8% methanol in chloroform as an eluent to obtain the title compound.

Yield: 0.050 g (45%); $^1$H NMR (DMSO-d$_6$, 300 MHz): δ 1.243-1.197 (t, 3H), 4.228-4.159 (q, 2H), 6.114 (s, 2H), 6.854 (s, 1H), 7.055-7.017 (dd, 1H), 7.628-7.599 (d, 1H), 7.986-7.977 (d, 1H); MS m/e: 284.7 (M +1).

Example 59

6-(4-methoxy-6-(trifluoromethyl)pyrimidin-2-yl) pyridin-3-amine

To a solution of compound of example 15 (0.100 g, 0.390 mmol) in DMF (3 mL), was added K$_2$CO$_3$ (0.080 g, 0.58 mmol) and stirred at 25° C. for 10 minutes. To the reaction mixture methyl iodide (0.083 g, 0.58 mmol) was added slowly and stirred at 25° C. for 1 hour. DMF was removed under vacuum and reaction mass quenched with water, extracted with ethyl acetate (3×10 mL), dried over sodium sulfate and concentrated to obtain the crude product, which was purified by column chromatography using silica gel and 8% methanol in chloroform as an eluent to obtain the title compound.

Yield: 0.089 g (84%); $^1$H NMR (DMSO-d$_6$, 300 MHz): δ 3.555 (s, 3H), 6.150 (s, 2H), 6.853 (s, 1H), 7.053-7.008 (m, 1H), 7.66-7.638 (d, 1H), 7.992 (s, 1H);
MS m/e: 270.6 (M +1).

Example 60

N-(6-(4-(allyloxy)-6-(trifluoromethyl)pyrimidin-2-yl)pyridin-3yl-)-2-chloroacetamide To a solution of compound of example 57 (0.100 g, 0.337 mmol) in THF (5 mL), at 0° C. was added triethylamine (0.051 g, 0.506 mmol) and chloroacetylchloride (0.057 g, 0.506 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 50% ethyl acetate in petroleum ether as an eluent) to obtain the title compound.

Yield: 0.110 g (88%); $^1$H NMR (DMSO-d$_6$, 300 MHz): 5 4.345 (s, 2H), 4.896 (m, 3H), 5.040-5.002 (dd, 1H), 5.838-5.710 (m, 1H), 7.063 (s, 1H), 7.845-7.817 (d, 1H), 8.249-8.212 (dd, 1H), 8.865-8.857 (d, 1H), 10.851 (s, 1H); MS m/e: 372.8 (M+1).

Example 61

2-Chloro-N-(6-(4-methoxy-6-(trifluoromethyl)pyrimidin-2-yl)pyridin-3yl)acetamide To a cool (0° C.) solution of compound of example 59 (0.08 g, 0.296 mmol) in THF (5 mL) was added triethylamine (0.044 g, 0.44 mmol) and chloroacetylchloride (0.050 g, 0.44 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 50% ethyl acetate in petroleum ether as an eluent) to obtain the title compound.

Yield: 0.088 g (86%); $^1$H NMR (DMSO-d$_6$, 300 MHz): 5 3.463 (s, 3H), 4.351 (s, 2H), 7.020 (s, 1H), 7.898-7.869 (d, 1H), 8.300-8.247 (dd, 1H), 8.902-8.867 (d, 1H), 10.866 (s, 1H); MS m/e: 344.8 (M−1).

Example 62

2-Chloro-N-(6-(4-ethoxy-6-(trifluoromethyl)pyrimidin-2-yl)pyridin-3yl)acetamide

To a cool (0° C.) solution of compound of example 58 (0.04 g, 0.14 mmol) in THF (3 mL) was added triethylamine (0.021 g, 0.21 mmol) and chloroacetylchloride (0.023 g, 0.21 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 50% ethyl acetate in petroleum ether as an eluent) to obtain the title compound.

Yield: 0.046 g (90%); $^1$H NMR (DMSO-d$_6$, 300 MHz): δ 1.225 (s, 3H), 4.043-3.973 (q, 2H), 4.349 (s, 2H), 7.021 (s, 1H), 7.872-7.844 (d, 1H), 8.269-8.231 (dd, 1H), 8.887-8.880 (d, 1H), 10.858 (s, 1H); MS m/e: 358.9 (M−1).

Example 63

6-(4-(allyloxy)-5-ethyl-6-methylpyrimidin-2-yl)pyridin-3-amine

To a solution of compound of example 52 (0.200 g, 0.86 mmol) in DMF (3 mL), was added K$_2$CO$_3$ (0.18 g, 1.302 mmol) and stirred at 25° C. for 10 minutes, followed by slow addition of allyl bromide (0.15 g, 1.302 mmol). The reaction mixture was stirred at 25° C. for 1 hour. DMF was removed under vacuum, and the reaction mass was quenched by water, extracted with ethyl acetate (3×20 mL), dried over sodium sulfate and concentrated to obtain the crude product, which was taken for synthesis of compound of example 64 without purification and characterization.

Example 64

N-(6-(4-(allyloxy)-5-ethyl-6-methylpyrimidin-2-yl) pyridin-3yl)-2-chloroacetamide To a cold (0° C.) solution of compound of example 63 (0.200 g, 0.739 mmol) in THF (10 mL), was added triethylamine (0.112 g, 1.109 mmol) and chloroacetylchloride (0.125 g, 1.109 mmol), and the reaction mixture was stirred at room temperature for 30 minutes. THF was removed under reduced pressure, and reaction mixture was quenched with water and extracted with ethyl acetate (3×15 mL). The organic layer was dried over anhydrous sodium sulfate and concentrated to obtain the crude product, which was purified by column chromatography (silica gel) using 50% ethyl acetate in petroleum ether as an eluent to obtain the title compound.

Yield: 0.120 g (46%); $^1$H NMR (DMSO-d$_6$, 300 MHz): δ 1.049 (t, 3H), 2.52-2.32 (m, 2H), 2.265 (s, 3H), 4.332 (s, 2H), 4.808-4.791 (d, 1H), 4.922-4.918 (d, 2H), 4.957-4.953 (d, 1H), 5.765-5.638 (m, 1H), 7.740-7.712 (d, 1H), 8.196-8.159 (dd, 1H), 8.798-8.790 (d, 1H), 10.777 (s, 1H); MS m/e: 345 (M−1).

Example 65

2-Chloro-N-(6-(5-ethyl-4-hydroxy-6-methylpyrimidin-2-yl)pyridin-3yl)acetamide

To a cold (0° C.) solution of compound of example 52 (0.100 g, 0.434 mmol) in THF (5 mL), was added triethylamine (0.065 g, 0.65 mmol) and chloroacetylchloride (0.073 g, 0.65 mmol), and the reaction mixture was stirred at room temperature for a period of 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5% methanol in chloroform as an eluent) to obtain the title compound.

Yield: 0.114 g (85%); $^1$H NMR (DMSO-d$_6$, 300 MHz): δ 1.199 (t, 3H), 1.265 (s, 3H), 2.295 (q, 2H), 4.325 (s, 2H), 8.287-8.183 (m, 2H), 8.862 (s, 1H), 10.817 (s, 1H), 11.796 (s, 1H); MS m/e: 305.2 (M−1).

Example 66

2-Chloro-N-(6-(5-chloro-4-hydroxy-6-methylpyrimidin-2-yl)pyridin-3yl)-2-phenylacetamide To a cold (0° C.) solution of compound of example 16 (0.10 g, 0.42 mmol) in THF (10 mL), was added triethylamine (0.064 g, 0.63 mmol) and 2-chloro-2-phenyl acetyl chloride (0.119 g, 0.63 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5 methanol in chloroform as an eluent) to obtain the title compound.

Yield: 0.039 g (23%); $^1$H NMR (DMSO-d$_6$, 300 MHz): δ 2.414 (s, 3H), 5.808 (s, 1H), 7.607-7.371 (m, 6H), 8.295-8.218 (m, 2H), 11.062 (s, 1H), 12.621 (s, 1H);
MS m/e: 387(M−1).

Example 67

2-Chloro-N-(6-(4-hydroxy-6-(trifluoromethyl)pyrimidin-2-yl)pyridin-3yl)-2-phenylacetamide To a cold (0° C.) solution of compound of example 15 (0.10 g, 0.39 mmol) in THF (10 mL), was added triethylamine (0.059 g, 0.58 mmol) and 2-chloro-2-phenylacetyl chloride (0.110 g, 0.58 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5 methanol in chloroform as an eluent) to obtain the title compound.

Yield: 0.124 g (77%); $^1$H NMR (DMSO-d$_6$, 300 MHz): δ 5.811 (s, 1H), 6.887 (s, 1H), 7.461-7.369 (m, 3H), 7.609-7.578 (dd, 2H), 8.321-8.238 (m, 2H), 8.968-8.961 (d, 1H), 11.11 (s, 1H), 12.841 (s, 1H); MS m/e: 409.06 (M+1).

Example 68

2-Chloro-N-(6-(4-hydroxy-6-(trifluoromethyl)pyrimidin-2-yl)pyridin-3yl)propanamide To a cold (0° C.) solution of compound of example 15 (0.10 g, 0.39 mmol) in THF (10 mL), was added triethylamine (0.059 g, 0.58 mmol) and 2-chloropropanoyl chloride (0.074 g, 0.58 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5% methanol in chloroform as an eluent) to obtain the title compound.

Yield: 0.128 g (94%); $^1$H NMR (DMSO-d$_6$, 300 MHz): δ 1.645 (d, 3H), 4.752-4.685 (q, 1H), 6.887 (s, 1H), 8.332-8.257 (m, 2H), 8.979 (s, 1H), 10.941 (s, 1H), 12.808 (s, 1H); MS m/e: 345 (M−1).

Example 69

2-Chloro-2,2-difluoro-N-(6-(4-hydroxy-6-(trifluoromethyl)pyrimidin-2-yl)pyridin-3yl)acetamide To a solution of compound of example 15 (0.10 g, 0.39 mmol) in DMF (10 mL) was added NaH (0.039 g, 0.97 mmol) and the reaction mixture was stirred at 25° C. for 15 minutes. To the reaction mixture 2-chloro-2,2-difluoroacetic anhydride (0.237 g, 0.97 mmol) was added, and the reaction mixture was stirred at room temperature for 30 minutes. DMF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5% methanol in chloroform an eluent) to obtain the title compound.

Yield: 0.128 g (94%); $^1$H NMR (DMSO-d$_6$, 300 MHz): 6.922 (s, 1H), 8.364 (s, 2H), 9.041 (s, 1H), 11.813 (s, 1H), 12.955 (s, 1H); MS m/e: 391 (M+Na).

Example 70

N-(6-(5-benzyl-4-hydroxy-6-methylpyrimidin-2-yl)pyridin-3-yl)-2-chloroacetamide

To a cold (0° C.) solution of compound of example 54 (0.050 g, 0.17 mmol) in THF (3 mL), was added triethylamine (0.025 g, 0.25 mmol) and chloroacetylchloride (0.029 g, 0.25 mmol), and the reaction mixture was stirred at room temperature for 30 minutes. THF was removed under reduced pressure, and reaction mixture was quenched with water and extracted with ethyl acetate (3×10 mL). The organic layer was dried over anhydrous sodium sulfate and concentrated to obtain the crude product, which was purified by column chromatography (silica gel, 5% methanol in chloroform as an eluent) to obtain the title compound.

Yield: 0.040 g (63%); $^1$H NMR (DMSO-$d_6$, 300 MHz): δ 2.254 (s, 3H), 3.832 (s, 2H), 4.342 (s, 2H), 7.156 (s, 1H), 7.246 (s, 3H), 7.273 (s, 1H), 8.286-8.204 (m, 2H), 8.887 (s, 1H), 10.843 (s, 1H), 11.979 (s, 1H); MS m/e: 367 (M−1).

Example 71

2-Chloro-N-(6-(4-chloro-6-(trifluoromethyl)pyrimidin-2-yl)pyridin-3-yl)acetamide To a solution of compound of example 53 (0.100 g, 0.301 mmol) in acetonitrile (5 mL), was added benzyl triethyl ammonium chloride (0.274 g, 1.204 mmol), dimethylaniline (0.143 g, 1.183 mmol) and POCl$_3$ (2.3 g, 15.05 mmol). The reaction mixture was refluxed for 3 hours. Acetonitrile was removed under vacuum, reaction mass neutralized by sodium bicarbonate solution and extracted with ethyl acetate (3×20 mL). The organic layer was dried over anhydrous sodium sulfate and concentrated to obtain the crude product, which was purified by column chromatography (silica gel, 5 % methanol in chloroform as an eluent) to obtain the title compound.

Yield: 0.069 g (66%); $^1$H NMR (DMSO-$d_6$, 300 MHz): δ 4.369 (s, 2H), 8.323 (s, 1H), 8.369 (s, 1H), 8.460-8.431 (d, 1H), 8.941-8.933 (d, 1H), 10.910 (s, 1H);

MS m/e: 373 (M+Na)

Pharmacological Data

The efficacy of the present compounds can be determined by a number of pharmacological assays well known in the art, such as described below. The exemplified pharmacological assays, which follow herein below, have been carried out with the compounds of the present invention.

ABBREVIATIONS

NCI: National Cancer Institute
ATCC: American Type Culture Collection
DMU: De Montford University
FBS: Fetal Bovine serum
PC-3: Prostate cancer cells
MTS: 3-(4,5-dimethylthiazol-2-yl)-5-(3-carboxymethoxyphenyl)-2-(4-sulfonyl)-2H-tetrazolium
PMS: Phenazine methosulfate
RPMI: Roswell Park Memorial Institute
Du-145: Human Prostate cancer cell line
HCT-116: Human Colon cancer cell line
MCF-7: Breast cancer cell line
HUVEC: Human Umbilical Vein Endothelial Cells
Panc-1: Pancreatic cancer cell line
WI-38: Human normal lung fibroblast
WI-38-Tag: Human normal lung fibroblast transformed
MRC-5: Human normal lung fibroblast
MRC-5-Tag: Human normal lung fibroblast transformed
Ovcar-3: Ovarian cancer cell line
F12K Ham's: Ham's F12 with Kaighn's modification
MEM: Minimum Essential Medium
NEAA: Non Essential Amino Acids
TC: Tissue Culture
PBS: Phosphate Buffered Saline
EDTA: Ethylenediamine tetracetic acid Source and culture conditions of various cell lines used in the studies are given in Table-1.

TABLE 1

Source and culture conditions

| Sr No | Cell line | Source | Medium of propagation (FBS %) |
|---|---|---|---|
| 1 | U251 HRE | NCI | RPMI-1640 (10%) |
| 2 | U251 pGL3 | NCI | RPMI-1640 (10%) |
| 3 | Du-145 | ATCC | RPMI-1640 (10%) |
| 4 | PC-3 | ATCC | F12K Ham's (10%) |
| 5 | HCT-116 | ATCC | Mc-Coys (10%) |
| 6 | MCF-7 | ATCC | RPMI-1640 (10%) |
| 7 | HUVEC | ATCC | Endothelial growth medium |
| 8 | Panc-1 | ATCC | MEM + NEAA (10%) |
| 9 | WI-38/WI-38-Tag | DMU | RPMI-1640 (10%) |
| 10 | MRC-5/MRC-5-Tag | DMU | RPMI-1640 (10%) |
| 11 | Ovcar-3 | ATCC | RPMI-1640 (10%) |

Example 72

HIF-1α Assay

The assay was designed as given in Cancer Research, 2002, 62, 4316-4324, Developmental Therapeutic programme, Tumor Hypoxia Laboratory, National Cancer Institute, Frederick, USA, with modifications as described below.

Cell lines:

U251-HRE: Genetically engineered U251 human glioma cells stably expressing a recombinant vector (pGL2-TK-HRE) in which the Luciferase reporter gene was under the control of hypoxia-responsive element and G418 vector.

U251-pGL3: To exclude compounds that can inhibit luciferase expression in non-specific and/or HIF-1 independent fashion a control cell line genetically engineered U251 human glioma cells stably expressing a recombinant vector (pGL3), U251-pGL3 was used.

Both the cell lines were maintained in RPMI 1640 and supplemented with 5% heat-inactivated fetal calf serum, penicillin (50 IU/mL), streptomycin (50 μg/mL) and 2 mm glutamine. Cells were maintained at 37° C. in a humidified incubator containing 5% carbon dioxide ($CO_2$).

Assay type: Cell based (Lucif erase Reporter Gene based assay)

Cells used: U251 HRE cells (Human glioma), stably transfected with human hypoxia responsive element and U251 pGL3 cells (control cell line)

Assay format: 96 well TC plate (Black)

Cell culture medium: RPMI-1640 supplemented with 5% FBS and 100 μg/mL G418

Seeding density: $1.5 \times 10^4$ cells per well (180 μL/well)

U251 HRE and U251 pGL3 cells were grown and maintained in RPMI1640 medium supplemented with 5% FBS. Cells were seeded in 96 well plate at a density of $1.5 \times 10^4$ cells in 180 μL per well and incubated at 37° C., 5% $CO_2$ overnight. Compounds of the present invention were diluted in RPMI1640 medium such that a final concentration of 50 μM, 10 μM, 3 μM and 1 μM was achieved in the well. The plates were incubated under two sets of conditions which were as follows.

Condition 1: Hypoxia
(<1% oxygen ($O_2$), 5% $CO_2$ and 94% Nitrogen, incubation temp 37° C.)

Condition 2: Normoxia
(21% $O_2$, 5% $CO_2$ and 74% Nitrogen, incubation temp 37° C.)

Topotecan (Calbiochem) was used as standard in each plate. Plates were incubated for 24 hours, thereafter cell were lysed with Lysis Buffer followed by addition of substrate. Plates were read for luminescence on POLARSTAR™ (or TOPCOUNT™). The 50% inhibitory concentration ($IC_{50}$) values were calculated under hypoxia and normoxia conditions.

Representative compounds within the scope of the present invention show $IC_{50}$ (μM) under hypoxia condition in the range of 0.8±0.1 to 2.0±0.3, and $IC_{50}$ (μM) under normoxia condition in the range of >5 to >30.

To identify the specificity of the compounds of present invention to inhibit HIF-1α under hypoxia conditions, Specificity Index (SI) was calculated as follows:

$$SI = \frac{IC_{50} \; \mu M \text{ under Normoxia condition}}{IC_{50} \; \mu M \text{ under Hypoxia condition}}$$

An observed SI of greater than 4 indicates specificity towards HIF-1α inhibition under hypoxia conditions. The results are given in following Table-2.

TABLE 2

| Sr. No | Example No. | Specificity Index |
|---|---|---|
| 01 | 4 | >20 |
| 02 | 29 | >9 |
| 03 | 30 | >11 |
| 04 | 41a | >10 |
| 05 | 53 | >7 |
| 06 | 60 | >15 |
| 07 | 61 | >15 |
| 08 | 64 | >15 |
| 09 | 71 | >6 |
| 10 | Topotecan | 50 |

Example 73

Western Blot Analyses

To confirm the compound mediated inhibition of HIF-1α, western blot analyses were carried out. Studies were performed to ascertain the inhibition of endogenous and over expressed levels of HIF-1α protein in the treated cell samples.

U251-HRE cells were cultured as described herein above. Prostate cancer cells (PC-3 cells; ATCC; Manassas, Va., USA) were cultured in F12K Ham's medium (Gibco BRL) supplemented with 10% heat inactivated FBS (Invitrogen), 100 U/ml penicillin and 100 μg/ml streptomycin. Confluent U251 HRE or PC-3 cells were seeded in tissue culture grade Petri plates at a density of 1-2×10⁶ cells per plate. The cells were incubated in a humidified incubator for a period of 18-24 hours. Subsequently, cells were treated with appropriate concentrations of the compounds of present invention or standard HIF Inhibitor (topotecan). Desferoxamine (100 μM; DFX; Sigma) was added to each of the plates except the control (no DFX) plate—(Cells were also treated under hypoxia). Cells were then incubated for 2, 4, 6, 8, 12 and 24 hours. Following the incubation, cells were harvested by trypsinization, rapidly washed with ice-cold PBS and lysed with cold Cell Lytic buffer (Sigma Aldrich) supplemented with complete protease inhibitor cocktail (Roche, Germany). The protein extracts (supernatants) were obtained after centrifugation at 14,000 g at 4° C. (30 minutes). Aliquots of the resulting extracts were analyzed for their protein content using Bradford Reagent (Sigma) as per manufacturer's instructions. In all experiments, equivalent amounts of protein (60 μg) were loaded on 7.5%-10% Trisglycine gels and resolved at 0.100 V for 2 hours in a buffered solution (24.9 mM Tris base, 250 mM glycine, 0.1% SDS (sodium dodecylsulfate)). After electrophoresis, the proteins were transferred from the gel to a polyvinylidene difluoride membrane (Sigma-Aldrich) at 25 V for 45 minutes in transfer buffer (47.9 mM Tris base, 38.6 mM glycine, 0.037% SDS, 20% methanol; pH 9.2-9.4). Blots were blocked in Tris-buffered saline (TBS) (20 mM Tris base, 0.9% NaCl; pH 7.4) containing 5% nonfat dry milk (Santa Cruz Biotechnology) for 2 hours at room temperature, and incubated with the primary antibody which was prepared in TBS at 4° C. overnight with gentle rocking. Primary antibodies included antibodies against monoclonal HIF-1α (BD Biosciences, CA, USA) and β-actin (Cell Signaling; USA). Following the incubation, membranes were washed and then probed with horse-radish peroxidase (HRP)-conjugated secondary antibodies. Bands were visualized using chemi-luminescent peroxidase substrate (Pierce, Ill., USA) and a Kodak Imaging station. Blots were stripped with stripping buffer (50 mM Tris-HCl pH 6.8, 1% SDS and 100 mM β-mercaptoethanol) for 20 minutes at 50° C., washed and re-probed with a primary antibody to the housekeeping protein β-actin as a loading control.

The blot results indicate that certain representative compounds within the scope of the present invention inhibit HIF-1α protein under hypoxia and DFX.

Example 74

Cytotoxicity and Anti-proliferative Assay

Cytotoxic potential of compounds of the present invention was tested using various HIF over expressing cell lines (source and culture conditions as described in Table-1 herein above). Cells were seeded at a density of 3000-5000 cells per well in 180 μL volume in transparent 96 well tissue culture plate (NUNC, USA) and incubated for 12-18 hours at 37° C., 5% $CO_2$. Subsequently, 20 μL of compounds of present invention (diluted in medium at concentrations ranging from 30 μM, 10 μM, 3 μM, 1 μM, 0.3 μM or 0.1 μM) were added to each well. Cells were then incubated for 48 hours at 37° C., 5% $CO_2$. Following the incubation, 20 μL of MTS solution with PMS (Promega) was added in each well. After 4 hours incubation, the absorbance of the fluid in each well was determined at 490 nm using a microwell plate spectrophotometer reader (Molecular Devices, Sunnyvale, Calif., USA). In every experiment, each condition was run in triplicate wells. The 50% inhibitory concentration ($IC_{50}$) values were calculated by a nonlinear regression method using GraphPad software (Prism 3.03).

The anti-proliferative potential of compounds of present invention across a panel of cancer cell lines as described herein above was determined using $^3$H-Thymidine incorporation. All the cell lines were procured from ATCC and maintained under optimum conditions of growth as suggested by the supplier. Cells were seeded at a density of 3000-5000 cells per well in 180 μL volume in transparent 96 well tissue culture plate (NUNC, USA) and incubated for 12-18 hours at 37° C., 5% $CO_2$. Subsequently, 20 μL of compounds of present invention (diluted in medium at concentrations ranging from 30 μM, 10 μM, 3 μM, 1 μM, 0.3 μM or 0.1 μM) were added to each well. Cells were then incubated for 48 hours at 37° C., 5% $CO_2$ After the incubation, all the medium from the plates was aspirated and $^3$H-Thymidine was added to all wells at a concentration of 0.25 μCi/well in 200 μL it complete medium (RPMI with 10% FBS). Plates were incubated at 37° C., 5% $CO_2$ for further 6-14 hours. Following this incubation period, cells from 96 well plates were harvested with the help of cell harvester (Packard, USA) on a 96 well glass-filter plate (Unifilter-96, GF/B, Packard, USA). The filter plates were dried completely at 60° C. for 1 hour or overnight at room temperature. After drying, the bottom of the plates was sealed with bottom seals and 0.05 mL/well of scintillate fluid was added per well (Microscint-O, Packard). The plates were sealed from the top, read on Scintillation counter (TopCount, Packard) and percent inhibition and $IC_{50}$ were calculated.

Average $IC_{50}$ (µM) values of certain representative compounds within the scope of the present invention across a panel of HIF overexpressing cell lines are as given below in Table-3.

TABLE 3

| Sr. No | Example No. | Cytotoxic Potential (MTS/PI) | Anti Proliferative Potential (3H-Thymidine) |
|---|---|---|---|
| 01 | 4 | 2.2 ± 0.3 | 2.0 ± 0.5 |
| 02 | 29 | 3.5 ± 0.5 | 1.5 ± 0.4 |
| 03 | 30 | 3.0 ± 0.5 | 1.5 ± 0.2 |
| 04 | 41a | 3.5 ± 1.0 | ND |
| 05 | 53 | 2 ± 0.5 | 2 ± 0.3 |
| 06 | 60 | 2.0 ± 0.2 | 0.8 ± 0.2 |
| 07 | 61 | 3.0 ± 0.2 | ND |
| 08 | 64 | 1.5 ± 0.2 | 1.0 ± 0.2 |
| 09 | 71 | 1.0 ± 0.2 | 0.8 ± 0.2 |

ND: Not Detected

Example 75

Wound Healing Migration Assay

To test the anti-migratory potential of HIF-1 inhibitors, wound healing assays were performed. The wound-healing assay is simple, inexpensive, and one of the earliest developed methods to study directional cell migration in vitro. This method mimics cell migration during wound healing in vivo.

All the cancer cell lines utilized in this assay (PC-3, DU-145, MCF-7 and HCT-116) were obtained from ATCC and cultured as per ATCC's recommendation. Cultured cells in their respective mediums were grown to 60-80% confluency. Subsequently, the cells were trypsinized and seeded at a density of $0.5-2.0\times10^6$ cells per well in a sterile 6 well plate. The cells were incubated overnight at 37° C., 5% $CO_2$ under ambient oxygen levels. The cells were observed to form a confluent uniform monolayer on the complete surface of the well. For wound assay, the cell monolayer was scrapped (with a sterile pipette tip) in a straight line evenly to create a "scratch". The first image of the scratches was acquired prior to compound addition. Following this, representative compounds within the scope of the present invention and standards (at appropriate concentrations) were added to the cells. The cells were then kept in the incubator for further incubation. The time frame for incubation was determined empirically for the particular cell type used. The dishes were taken out of the incubator periodically to be examined and then returned to resume incubation. After the incubation, the dish was placed under a phase contrast microscope. With the reference point matched, the photograph regions of the first image were aligned and second image was acquired. For each image, distance between one side of the scratch and the other was measured.

Certain representative compounds within the scope of the present invention were found to have potent anti-migratory potential across a panel of cell lines.

Example 76

Invivo Studies

In-vivo efficacy of the compounds of the present invention was tested in Prostrate cancer (PC-3) tumor model. Animals were housed and cared for in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of the Research Centre of Piramal Life Sciences Limited, Mumbai, India.

Compound Storage:

All the compounds including standard were stored at 4-8° C. in an amber colored bottle. The compounds in solutions were also maintained at 4-8° C. in a refrigerator. Sample for animal injection was made fresh everyday.

Dose Preparation:

Required compound was weighed and mixed with 0.5% (w/v) carboxymethyl cellulose (CMC) and triturated with Tween-20 (secundum artum) with gradual addition of water to make up the final concentration.

Efficacy Study in SCID Mice:

Severely Combined Immune-Deficient (SCID strain-CBySmn.CB17-Prkdc$^{scid}$/J, The Jackson Laboratory, Stock #001803) male mice weighing about 20 g of 6-9 weeks old were used in the study.

PC-3 cells were grown in Ham's F12K medium containing 10% fetal calf serum in 5% $CO_2$ incubator at 37° C. Cells were pelleted by centrifugation at 1000-rpm for 10 minutes. Cells were resuspended in saline to get a count of $30-50\times10^6$ cells per mL, 0.2 mL of this cell suspension was injected by subcutaneous (s.c.) route in SCID mice. Mice were observed every alternate days for palpable tumor mass. Once the tumor size reached a size of 5-7 mm in diameter, animals were randomized into respective treatment groups. Dose was administered every day. Tumor size was recorded on every 2-5 day interval.

Tumor weight (mg) was estimated according to the formula for a prolate ellipsoid:

$$\{Length\ (mm)\times[width\ (mm)^2]\times0.5\}$$

assuming specific gravity to be one and to be three.

Tumor growth in compound treated animals was calculated as

T/C (Treated/Control)×100% and Growth inhibition Percent (GI %) was [100-T/C %].

Certain representative compounds within the scope of the present invention show moderate to significant in vivo anti-tumor activity in PC-3 xenograft model.

Example 77

PI3Kα Kinase Assay

The PI3K kinase assay was designed as given in Cell, 2006, 125, 733-747.

The kinase reaction was carried out in a 25 µL reaction in a 1.5 ml microcentrifuge tube. The reaction mixture consisted of kinase buffer (10 mM Hepes, pH 7.5, 50 mM $MgCl_2$), 20 ng PI3Kα kinase, 12.5 µg phosphotidylinositol (PI), 10 µM adenosine triphosphate (ATP) and 1 µCi 32γP deoxyadenosine triphosphate (dATP). The compounds of the present invention were added at appropriate concentrations. The reactions were incubated at 30° C. for 20 minutes and were stopped by adding 1:1 mixture of methanol and chloroform. The tube contents were mixed on a vortex mixer and centrifuged at 10000 rpm for 2 minutes. 10 µL of the organic (lower) phase was spotted on to a thin layer chromatography (TLC) plate. The spots were resolved in a mobile phase consisting of a 65:35 mixture of n-propanol and 2 M glacial acetic acid. The plates were dried and exposed to an X-ray film. The bands appearing as a result of 32 g P incorporation in PI were quantitated using the QuantityOne (BioRad) densitometry program.

The 50% inhibitory concentration (IC$_{50}$) values for certain representative compounds within the scope of the present invention are given in Table-4.

Example 78

Cell Based mTOR Assay

The mTOR assay was designed as given in Biochem J., 2000, 350, 717-722 with modifications as described below.

Cells were seeded in a 96 well microtitre plate at a density of 50,000 cells/cm$^2$ in appropriate complete cell culture medium. The cells were allowed to adhere for 18-24 hours. The cells were pretreated (in triplicates) with the test compound at a concentration of 10 µM for 30 minutes followed by induction with 400 ng/ml IGF-I for 24 hours (to induce AKT and p70S6K1 phosphorylation). A typical assay would consist of a set of unstimulated well, a set of stimulated and a set each of wells treated with compound and the stimulator. The medium was discarded. The cells were fixed with 100 µl of 3.7% formaldehyde for 15 minutes. The formaldehyde was discarded by inverting the plate and tapping it on a thick tissue paper layer to remove traces. The cells were washed and permeabilized with 200 µL PBS-Triton solution (containing 0.1% triton-X 100 in 1×PBS) three times, incubating the cells each time for 5 minutes. 100 µL blocking solution (10% FCS in PBS-Triton) was added and incubated for 1 hour at room temperature. The blocking solution was discarded and cells were incubated with the primary antibody in PBS-Triton at a dilution of 1:500 for 1 hour at room temperature. [The primary antibody is Phospho-AKT (Ser 473); Cell Signaling; Cat. No. 9271; Phospho p70S6K1 (Thr 389), Cell Signaling, Cat. No. 9205]. The primary antibody solution was discarded and the cells were washed 3 times with PBS-Triton solution and incubated with the HRP-conjugated secondary antibody in PBS-Triton at a dilution of 1:500 for 1 hour at room temperature. The cells were washed 3 times with PBS-Triton followed by two washes with PBS (to remove traces of triton-X 100). The OPD (o-phenylene diamine dihydrochloride) substrate was prepared for detection of the signal by dissolving one tablet set (two tablets) of SigmaFast OPD (Sigma, Cat No. P9187) in 20 mL distilled water, and was protected from light. 100 µL OPD solution was added to the wells and the plate was incubated in the dark for 3-5 minutes (depending upon the development of the colour). The reaction was stopped by adding 50 µL 2 N sulphuric acid (H$_2$SO$_4$). The absorbance was measured at 490 nm. The values were expressed in the treated samples, in terms of percentage or fold decrease in AKT/p70 phosphorylation with respect to the induced sample.

The 50% inhibitory concentration (IC$_{50}$) values for certain representative compounds within the scope of the present invention are given in Table-4.

TABLE 4

| Example No. | Inhibition of PI3Kα (kinase): IC$_{50}$ (µM) | Inhibition of mTOR (cell-based): IC$_{50}$ (µM) |
| --- | --- | --- |
| 4 | 10 | 5 |
| 60 | 1.5 | 5 |
| 61 | 1 | 5 |
| 64 | <1 | 5 |
| 65 | 10 | 10 |

Example 79

TNF-α Assay (in vitro)

Standard in vitro assays for testing anti-inflammatory properties of compounds include analysis of the levels of TNF-α released upon stimulation of human peripheral blood mononuclear cells (hPBMCs) with lipopolysaccharides (LPS). Alternatively, release of various cytokines such as IL-6 and IL-8 from TNF-α stimulated hPBMCs can also be analysed. Briefly, 96-well tissue cultures plates were coated with the antibody of interest (e.g. anti-TNF-α, anti-IL-6, anti-IL-B) overnight at 4° C. hPBMCs were either left non treated or were pretreated with the standard inhibitors (positive control) or with the compounds of present invention for 1 hour. The cells were then stimulated with LPS/TNF-α (depending upon the readout as mentioned herein above) for 5 hours. The plates were centrifuged and the supernatant was frozen at −70° C. until further use. For performing the ELISA, the coated plates were blocked in blocking buffer (10% FBS in PBS containing 0.05% tween 20) for 1 hour. Following washes with PBS/ tween solution, the supernatant was added to the wells. In some wells, known amounts of purified cytokines were added to plot a standard linear graph, which would help in quantification. Following an hour of incubation, the wells were emptied and washed with PBS/tween solution. An appropriate secondary HRP-conjugated antibody was added and the plates were incubated for 1 hour, which was followed, by washing and detection using tetramethyl benzidine (TMB) substrate. The color reaction was stopped by adding 0.5 M sulfuric acid and measured at 490 nm. The levels of cytokines in the treated samples were compared with those of the non-treated (but LPS/TNF-α treated samples).

Certain representative compounds within the scope of the present invention were found to inhibit TNF-α activity.

Example 80

LPS-induced TNF-α Release in Balb/c Mice (in vivo)

The assay was designed as in reference, J. Med. Bio. Res., 1997, 30, 1199-1207, the disclosure of which is incorporated by reference for the teaching of the assay. Balb/c mice of either sex weighing between 18-22 g were orally administered representative compounds of the present invention at doses of 12.5, 50, 75, 100 mg/kg. All suspensions were freshly prepared in 0.5% CMC. One hour later, LPS (1 mg/kg) (*Escherchia coli*, serotype 0127:B8, Sigma Chemical Co., St. Louis, Mo.) dissolved in sterile pyrogen-free saline was administered intra-peritoneally to the control group, standard treatment group (Rolipram, 30 mg/kg, p.o.) and test groups (compounds of present invention), except the negative control group, which received normal saline.

Blood samples were collected from anesthetized mice, with heparin as an anti-coagulant (25 IU per sample) 1.5 hours post LPS challenge. These were then centrifuged at 10000 rpm for 10 minutes and plasma samples were analysed for levels of TNF-α by ELISA, as described by the manufacturer (OptiEIA ELISA sets, BD BioSciences Pharmingen).

Percent inhibition of TNF-α release was calculated by comparing the TNF-α levels of the treatment groups with those of the control group.

Certain representative compounds within the scope of the present invention were efficacious in inhibiting LPS-induced TNF-α release in Balb/c mice.

Example 81

Collagen Induced Arthritis in Mouse (in vivo)

The assay was designed as in reference, J. Exp. Med., 1985, 162, 637-646, the disclosure of which is incorporated by reference for the teaching of the assay.

Male DBA/1J mice, aged 8-10 weeks were immunized with an emulsion equivalent to 200 µg of type II collagen in Freund's Complete Adjuvant, injected intradermally at the base of the tail. A booster shot with the same emulsion was given 21 days later. A group of naive mice was maintained alongside.

From day 23, mice were examined daily once for the signs of rheumatoid arthritis, using the Articular Index and paw thickness as parameters. Articular Index scoring was performed employing the following criteria:

Forelimbs: Scale 0-3
0: No redness or swelling
1: Redness, but no swelling
2: Redness and swelling of the paw
3: Redness and severe swelling of the paw Hind limbs: Scale 0-5
0: No redness or swelling
1: Redness and mild swelling of paw
2: Redness and moderate swelling of paw and/or swelling of at least one of the digits.
3: Redness and moderate/severe swelling of paw, swelling of ankle joint and/or swelling of one or more digits.
4: Redness and severe swelling of paw, digits and ankle joint, with joint stiffness.
5: Redness and severe swelling of paw, digits and ankle joint, with joint stiffness and altered angle of digits.

Mice with a minimum hind paw score of 2 were inducted into the study.

Mice were randomized into the various study groups and were orally administered with the vehicle (0.5% CMC, 1 ml/kg), exemplary compounds within the scope of the present invention (50 mg/kg, 75 mg/kg, twice daily and 100 mg/kg once daily) and standard compound (Enbrel, 3 mg/kg, s.c., once daily). Each group had a minimum of 8 mice. The dosing of the compounds was done for 24 days.

The following parameters were observed and recorded daily,
1. Body weight
2. Articular index
3. Paw thickness in mm using a tension free caliper
4. Any significant observation regarding the condition of the animal.

On the last day ($24^{th}$ day of dosing), one hour after the compound treatment, the animals were sacrificed, blood withdrawn, and plasma collected for drug level analyses. Also, the limbs of all the animals were preserved for histopathological evaluations.

Histopathological Analysis:

Mice were humanely euthanized and the hind paws were harvested from each animal, fixed in 10% neutral buffered formalin, decalcified in 10% EDTA and embedded in paraffin. Sections (5 µm) were stained with hematoxylin-eosin and safranin O and evaluated microscopically. Histopathological changes were scored as follows: mild (score=1), moderate (score=2) or severe (score=3) for the parameters of cellular infiltration, bone erosions and cartilage damage, graded separately. Cartilage depletion was indicated visually by diminished safranin O staining of proteoglycan matrix. The mean total score was compared to that of vehicle treated group. In case of histological scoring, Kruskal-Wallis analysis was followed by Dunn's multiple comparison tests to evaluate the statistical difference between two groups. Values of p<0.05 were considered significant.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula (I):

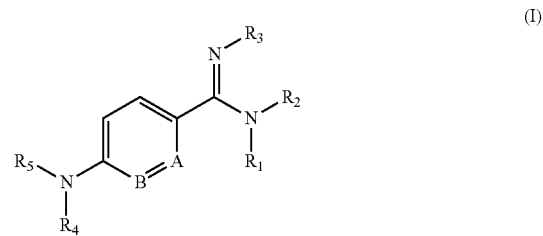

wherein,
A is nitrogen and B is carbon;
$R_1$ is selected from hydrogen, alkyl, alkenyl, alkynyl, acyl, hydroxy, alkoxy, aryl, and aryloxy, or is absent;
$R_2$ is selected from hydrogen, alkyl, alkenyl, alkynyl, acyl, hydroxy, alkoxy, aryl, and aryloxy;
$R_3$ is selected from hydrogen, alkyl, alkenyl, alkynyl, acyl, hydroxy, alkoxy, aryl, aryloxy, and —O—$R_6$; or
$R_2$ and $R_3$ together with the N atom to which they are attached form an unsubstituted or substituted heterocycle selected from 1,2,4-oxadiazole or pyrimidine;
$R_4$ and $R_5$ are independently selected from hydrogen, alkyl, haloalkyl, aralkyl, alkenyl, alkynyl, aryl, heterocyclyl, cycloalkyl, —O—$R_6$, and —C(O)-T-Q;
$R_6$ is selected from alkenyl and alkynyl; wherein the alkenyl and alkynyl may be unsubstituted or substituted;
T is selected from —$(CR_7R_8)_n$— and —$C(R_7R_8)C(O)$—, where n is an integer from 0 to 5;
$R_7$ and $R_8$ are independently selected from hydrogen, alkyl, haloalkyl, cycloalkyl, alkenyl, halogen, hydroxy, alkoxy, cyano, nitro, aryl, and heterocyclyl; and
Q is selected from hydrogen, hydroxy, halogen, cyano, nitro, alkyl, haloalkyl, alkoxy, cycloalkyl, and heterocyclyl;
where, in $R_1$, $R_2$, $R_3$, $R_4$, $R_5$, $R_7$, $R_8$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—$R_6$, and —O—$R_6$;

with a proviso that:

when $R_1$ is selected from hydrogen, alkyl, alkenyl, alkynyl, acyl, hydroxy, alkoxy, aryl, and aryloxy, then at least one of $R_4$ and $R_5$ is —C(O)-T-Q;

with a further proviso that:

when Q or any one of $R_7$ and $R_8$ is selected from cycloalkyl, heterocyclyl, and aryl; then a) $R_2$ and $R_3$ are independently selected from groups other than hydrogen and hydroxy; and b) if $R_2$ and $R_3$ together with the N atom to which they are attached forms a ring, then the ring is not a 5-membered heterocycle;

and stereoisomeric and tautomeric forms and mixtures thereof in all ratios, pharmaceutically acceptable salts, pharmaceutically acceptable solvates and pharmaceutically acceptable polymorphs thereof.

2. A compound according to claim 1, having formula (Ia);

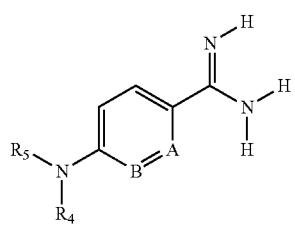

(Ia)

wherein,

A is nitrogen and B is carbon;

$R_4$ is selected from hydrogen, alkyl, haloalkyl, aralkyl, alkenyl, alkynyl, aryl, heterocyclyl, cycloalkyl, —O—$R_6$, and —C(O)-T-Q;

$R_5$ is —C(O)-T-Q;

$R_6$ is selected from alkenyl and alkynyl; wherein the alkenyl and alkynyl may be unsubstituted or substituted;

T is selected from —$(CR_7R_8)_n$— and —$C(R_7R_8)C(O)$—, where n is an integer from 0 to 5;

$R_7$ and $R_8$ are independently selected from hydrogen, alkyl, haloalkyl, cycloalkyl, alkenyl, halogen, hydroxy, alkoxy, cyano, nitro, aryl, and heterocyclyl; and Q is halogen;

where, in $R_4$, $R_7$ and $R_8$:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—$R_6$, and —O—$R_6$;

and stereoisomeric and tautomeric forms and mixtures thereof in all ratios, pharmaceutically acceptable salts, pharmaceutically acceptable solvates and pharmaceutically acceptable polymorphs thereof.

3. A compound according to claim 2, wherein

A is nitrogen;

B is carbon;

$R_4$ is selected from hydrogen, alkyl, haloalkyl, aralkyl, alkenyl, alkynyl, aryl, heterocyclyl, cycloalkyl, —O—$R_6$, and —C(O)-T-Q;

$R_5$ is —C(O)-T-Q;

$R_6$ is selected from alkenyl and alkynyl; wherein the alkenyl and alkynyl may be unsubstituted or substituted;

T is —$CR_7R_8$—;

$R_7$ and $R_8$ are independently selected from hydrogen, alkyl, haloalkyl, cycloalkyl, alkenyl, halogen, hydroxy, alkoxy, cyano, nitro, aryl, and heterocyclyl; and Q is halogen;

where, in $R_4$, $R_7$ and $R_8$:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—$R_6$, and —O—$R_6$;

and stereoisomeric and tautomeric forms and mixtures thereof in all ratios, pharmaceutically acceptable salts, pharmaceutically acceptable solvates and pharmaceutically acceptable polymorphs thereof.

4. A compound according to claim 3, wherein

A is nitrogen;

B is carbon;

$R_4$ is hydrogen;

$R_5$ is —C(O)-T-Q;

T is —$CH_2$—;

Q is halogen;

and stereoisomeric and tautomeric forms and mixtures thereof in all ratios, pharmaceutically acceptable salts, pharmaceutically acceptable solvates and pharmaceutically acceptable polymorphs thereof.

5. A compound according to claim 1, having formula (Ib);

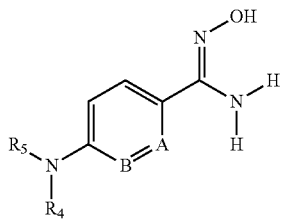

(Ib)

wherein,
A is nitrogen and B is carbon; $R_4$ is selected from hydrogen, alkyl, haloalkyl, aralkyl, alkenyl, alkynyl, aryl, heterocyclyl, cycloalkyl, —O—$R_6$, and —C(O)-T-Q;
$R_5$ is —C(O)-T-Q;
$R_6$ is selected from alkenyl and alkynyl; wherein the alkenyl and alkynyl may be unsubstituted or substituted;
T is selected from —$(CR_7R_8)_n$— and —$C(R_7R_8)C(O)$—, where n is an integer from 0 to 5;
$R_7$ and $R_8$ are independently selected from hydrogen, alkyl, haloalkyl, cycloalkyl, alkenyl, halogen, hydroxy, alkoxy, cyano, nitro, aryl, and heterocyclyl; and
Q is halogen;
where, in $R_4$, $R_7$ and $R_8$:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—$R_6$, and —O—$R_6$;
and stereoisomeric and tautomeric forms and mixtures thereof in all ratios, pharmaceutically acceptable salts, pharmaceutically acceptable solvates and pharmaceutically acceptable polymorphs thereof.

6. A compound according to claim 5, wherein
A is nitrogen;
B is carbon;
$R_4$ is selected from hydrogen, alkyl, haloalkyl, aralkyl, alkenyl, alkynyl, aryl, heterocyclyl, cycloalkyl,—O—$R_6$, and —C(O)-T-Q;
$R_5$ is —C(O)-T-Q;
$R_6$ is selected from alkenyl and alkynyl; wherein the alkenyl and alkynyl may be unsubstituted or substituted;
T is —$(CR_7R_8)_n$—,
n is an integer from 0 to 2;
$R_7$ and $R_8$ are independently selected from hydrogen, alkyl, haloalkyl, cycloalkyl, alkenyl, halogen, hydroxy, alkoxy, cyano, nitro, aryl, and heterocyclyl; and
Q is halogen;
where, in $R_4$, $R_7$ and $R_8$:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—$R_6$, and —O—$R_6$;
and stereoisomeric and tautomeric forms and mixtures thereof in all ratios, pharmaceutically acceptable salts, pharmaceutically acceptable solvates and pharmaceutically acceptable polymorphs thereof.

7. A compound according to claim 6, wherein
A is nitrogen;
B is carbon;
$R_4$ is hydrogen;
$R_5$ is —C(O)-T-Q;
T is —$(CR_7R_8)$—;
n is an integer from 0 to 2;
$R_7$ and $R_8$ are independently selected from hydrogen, halogen, and alkyl; and
Q is halogen;
where, in $R_7$ and $R_8$:
alkyl is unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
and stereoisomeric and tautomeric forms and mixtures thereof in all ratios, pharmaceutically acceptable salts, pharmaceutically acceptable solvates and pharmaceutically acceptable polymorphs thereof.

8. A compound according to claim 1, having formula (Ic);

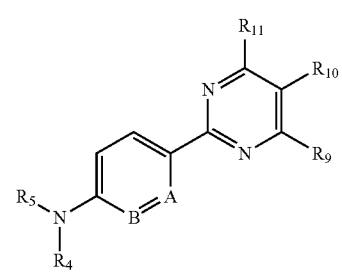

(Ic)

wherein:
A is nitrogen and B is carbon;
$R_4$ and $R_5$ are independently selected from hydrogen, alkyl, haloalkyl, aralkyl, alkenyl, alkynyl, aryl, heterocyclyl, cycloalkyl, —O—$R_6$, and —C(O)-T-Q;
$R_6$ is selected alkenyl and alkynyl; wherein the alkenyl and alkynyl may be unsubstituted or substituted;

T is selected from —(CR$_7$R$_8$)$_n$— and —C(R$_7$R$_8$)C(O)—, where n is an integer from 0 to 5;
R$_7$ and R$_8$ are independently selected from hydrogen, alkyl, haloalkyl, cycloalkyl, alkenyl, halogen, hydroxy, alkoxy, cyano, nitro, aryl, and heterocyclyl;
Q is selected from hydrogen, hydroxy, halogen, cyano, nitro, alkyl, haloalkyl, alkoxy, cycloalkyl, and heterocyclyl;
R$_9$, R$_{10}$ and R$_{11}$ are independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclylalkyl, heteroarylalkyl, aralkyl, alkylaminoalkyl, formyl, alkylcarbonyl, arylcarbonyl, aryloxy, alkylamino, alkylheteroarylamino, alkoxycarbonyl, aryloxycarbonyl, —COOH, —C(O)—O—R$_6$, and —O—R$_6$;
where, in R$_4$, R$_5$, R$_7$, R$_8$, R$_9$, R$_{10}$, R$_{11}$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—R$_6$, and —O—R$_6$;
and stereoisomeric and tautomeric forms and mixtures thereof in all ratios, pharmaceutically acceptable salts, pharmaceutically acceptable solvates and pharmaceutically acceptable polymorphs thereof.

9. A compound according to claim 8, wherein
A is nitrogen;
B is carbon;
R$_4$ and R$_5$ are independently selected from hydrogen, alkyl, haloalkyl, aralkyl, alkenyl, alkynyl, aryl, heterocyclyl, cycloalkyl, —O—R$_6$ and —C(O)-T-Q;
R$_6$ is selected from alkenyl and alkynyl; wherein the alkenyl and alkynyl may be unsubstituted or substituted;
T is —CR$_7$R$_8$—;
R$_7$ and R$_8$ are independently selected from hydrogen, alkyl, haloalkyl, cycloalkyl, alkenyl, halogen, hydroxy, alkoxy, cyano, nitro, aryl, and heterocyclyl;
Q is selected from hydrogen, hydroxy, halogen, cyano, nitro, alkyl, haloalkyl, alkoxy, cycloalkyl, and heterocyclyl;
R$_9$, R$_{10}$ and R$_{11}$ are independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclylalkyl, heteroarylalkyl, aralkyl, alkylaminoalkyl, formyl, alkylcarbonyl, arylcarbonyl, aryloxy, alkylamino, alkylheteroarylamino, alkoxycarbonyl, aryloxycarbonyl, —COOH, —C(O)—O—R$_6$, and —O—R$_6$;
where, in R$_4$, R$_5$, R$_7$, R$_8$, R$_9$, R$_{10}$, R$_{11}$ and Q:
alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoacyl, aryl, aralkyl, and heterocyclyl;
aryl is unsubstituted or substituted with at least one group selected from halogen, nitro, alkyl, haloalkyl, alkoxy, amino, heteroarylalkyl, heterocyclyl, aryl, and aralkyl; and
heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—R$_6$, and —O—R$_6$;
and stereoisomeric and tautomeric forms and mixtures thereof in all ratios, pharmaceutically acceptable salts, pharmaceutically acceptable solvates and pharmaceutically acceptable polymorphs thereof.

10. A compound according to claim 9, wherein
A is nitrogen;
B is carbon;
R$_4$ is hydrogen;
R$_5$ is selected from hydrogen and —C(O)-T-Q;
R$_6$ is alkenyl;
T is —CR$_7$R$_8$—;
R$_7$ and R$_8$ are independently selected from hydrogen, halogen, alkyl and aryl;
Q is selected from hydrogen and halogen;
R$_9$, R$_{10}$ and R$_{11}$ are independently selected from hydrogen, halogen, hydroxy, alkoxy, haloalkyl, alkoxycarbonyl and —O—R$_6$;
where, in R$_7$ and R$_8$:
alkyl is unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl; and
aryl is unsubstituted or substituted with at least one group selected from halogen, nitro, alkyl, haloalkyl, alkoxy, amino, heteroarylalkyl, heterocyclyl, aryl, and aralkyl;
and stereoisomeric and tautomeric forms and mixtures thereof in all ratios, pharmaceutically acceptable salts, pharmaceutically acceptable solvates and pharmaceutically acceptable polymorphs thereof.

11. A compound according to claim 1, having formula (Id)

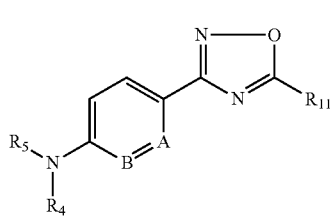

(Id)

wherein:
A is nitrogen and B is carbon;
R$_4$ and R$_5$ are independently selected from hydrogen, alkyl, haloalkyl, aralkyl, alkenyl, alkynyl, aryl, heterocyclyl, cycloalkyl, —O—R$_6$, and —C(O)-T-Q;
R$_6$ is selected from alkenyl and alkynyl; wherein the alkenyl and alkynyl may be unsubstituted or substituted;

T is selected from —(CR$_7$R$_8$)$_n$— and —C(R$_7$R$_8$)C(O)—, where n is an integer from 0 to 5;

R$_7$ and R$_8$ are independently selected from hydrogen, alkyl, haloalkyl, alkenyl, halogen, hydroxy, alkoxy, cyano and nitro;

Q is independently selected from hydrogen, hydroxy, halogen, cyano, nitro, alkyl, haloalkyl and alkoxy;

R$_{11}$ is independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclylalkyl, heteroarylalkyl, aralkyl, alkylaminoalkyl, formyl, alkylcarbonyl, arylcarbonyl, aryloxy, alkylamino, alkylheteroarylamino, alkoxycarbonyl, awloxycarbonyl, —COOH, —C(O)—O—R$_6$, and —O—R$_6$;

where, in R$_4$, R$_5$, R$_7$, R$_8$, R$_{11}$ and Q:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—R$_6$, and —O—R$_6$;

and stereoisomeric and tautomeric forms and mixtures thereof in all ratios, pharmaceutically acceptable salts, pharmaceutically acceptable solvates and pharmaceutically acceptable polymorphs thereof.

12. A compound according to claim 11, wherein A is nitrogen;

B is carbon;

R$_4$ and R$_5$ are independently selected from hydrogen, alkyl, haloalkyl, aralkyl, alkenyl, alkynyl, aryl, heterocyclyl, cycloalkyl, —O—R$_6$, and —C(O)-T-Q;

R$_6$ is selected from alkenyl and alkynyl; wherein the alkenyl and alkynyl may be unsubstituted or substituted;

T is —CR$_7$R$_8$—;

R$_7$ and R$_8$ are independently selected from hydrogen, alkyl, haloalkyl, alkenyl, halogen, hydroxy, alkoxy, cyano and nitro;

Q is selected from hydrogen, hydroxy, halogen, cyano, nitro, alkyl, haloalkyl and alkoxy;

R$_{11}$ is independently selected from hydrogen, halogen, hydroxy, alkoxy, oxo, alkyl, haloalkyl, cycloalkyl, cycloalkylalkyl, acyl, acyloxy, alkenyl, alkynyl, amino, aminoalkyl, hydroxyalkyl, heterocyclylalkyl, heteroarylalkyl, aralkyl, alkylaminoalkyl, formyl, alkylcarbonyl, arylcarbonyl, aryloxy, alkylamino, alkylheteroarylamino, alkoxycarbonyl, aryloxycarbonyl, —COOH, —C(O)—O—R$_6$, and —O—R$_6$;

where, in R$_4$, R$_5$, R$_7$, R$_8$, R$_{11}$ and Q:

alkyl and cycloalkyl are unsubstituted or substituted with at least one group selected from halogen, hydroxy, carboxy, acetoxy, amino, cycloalkyl, alkoxy, aryloxy, alkoxycarbonyl, aminocarbonyl, aminoaryl, aryl, aralkyl, and heterocyclyl;

aryl is unsubstituted or substituted with at least one group selected from halogen, nitro, alkyl, haloalkyl, alkoxy, amino, heteroarylalkyl, heterocyclyl, aryl, and aralkyl; and heterocyclyl is unsubstituted or substituted with at least one group selected from halogen, hydroxy, alkoxy, oxo, alkyl, haloalkyl, alkenyl, alkynyl, aryloxy, cycloalkyl, cycloalkylalkyl, acyl, acyloxy, amino, aminoalkyl, hydroxyalkyl, heterocyclylalkyl, heteroarylalkyl, aralkyl, alkylaminoalkyl, formyl, alkylcarbonyl, arylcarbonyl, alkylamino, alkylheteroarylamino, alkoxycarbonyl, aryloxycarbonyl, —COOH, —C(O)—O—R$_6$, and —O—R$_6$;

and stereoisomeric and tautomeric forms and mixtures thereof in all ratios, pharmaceutically acceptable salts, pharmaceutically acceptable solvates and pharmaceutically acceptable polymorphs thereof.

13. A compound according to claim 12, wherein

A is nitrogen;

B is carbon;

R$_4$ is hydrogen;

R$_5$ is —C(O)-T-Q;

T is -CR$_7$R$_8$—;

R$_7$ and R$_8$ are independently selected from hydrogen and halogen;

Q is halogen;

R$_{11}$ is selected from haloalkyl, unsubstituted alkyl and carboxy substituted alkyl;

and stereoisomeric and tautomeric forms and mixtures thereof in all ratios, pharmaceutically acceptable salts, pharmaceutically acceptable solvates and pharmaceutically acceptable polymorphs thereof.

14. A compound according to claim 1, wherein the compound is:

Methyl 2-(5-aminopyridin-2-yl)-5,6-dihydroxypyrimidine-4-carboxylate,

2-Chloro-N-(6-(N'-hydroxycarbamimidoyl)pyridin-3-yl)acetamide,

Methyl 2-(5-(2-chloroacetamide)pyridin-2-yl)-5,6-dihydroxypyrimidine-4-carboxylate, 2-Chloro-N-[6-(N-hydroxycarbamimidoyl)pyridine-3-yl]propionamide, 2,2-Dichloro-N-[6-(N-hydroxy carbamimidoyl)pyridin-3-yl]acetamide, 2-(-5-Aminopyridin-2-yl)-6-methylpyrimidin-4-ol, 2-Chloro-N-(6-(4-hydroxy-6-methylpyrimidin-2-yl)pyridin-3-yl)acetamide, 2-(5-Aminopyridin-2-yl)-6-(trifluoromethyl)pyrimidin-4-ol, 2-(5-Aminopyridin-2-yl)-5-chloro-6-methylpyrimidin-4-ol, 2-Chloro-N-[5-(N-hydroxycarbamimidoyl)pyridin-2-yl]acetamide, 3-Chloro-N-[6-(N-hydroxycarbamimidoy)pyridin-3-yl]propionamide, 2-Chloro-N-[5-(N-hydroxycarbamimidoyl)pyridine-2-yl]propionamide, 2-Chloro-N-[6-(5-(trifluoromethyl)-1,2,4-oxadiazol-3-yl)pyridin-3-yl]acetamide, 2-Chloro-N-[6-(5-methyl-1,2,4-oxadiazol-3-yl)pyridin-3-yl]acetamide, 3-(3-(5-(2-Chloroacetamido)pyridin-2-yl)-1,2,4-oxadiazol-5-yl)propanoic acid, 2-Chloro-2,2-difluoro-N-[6-(N'-hydroxycarbamimidoyl)pyridin-3-yl]acetamide, 2-Chloro-2,2-difluoro-N-(6-(5-(trifluoromethyl)-[1,2,4]oxadiazol-3-yl)pyridin-3-yl)acetamide, 2-Chloro-2-fluoro-N-[6-(N'-hydroxycarbamimidoyl)pyridine-3-yl]acetamide,
2-Chloro-2-fluoro-N-(6-(5-(trifluoromethyl)-1,2,4-oxadiazol-3-yl)pyridin-3-yl)acetamide,
2-Chloro-N-[6-(5-(chloromethyl)-1,2,4-oxadiazol-3-yl)pyridin-3-yl]acetamide,
2-Chloro-N-[6-(5-(chlorodifluoromethyl)-1,2,4-oxadiazol-3-yl)pyridin-3-yl]acetamide,
2-Chloro-N-[6-(5-(chlorodifluoromethyl)-1,2,4-oxadiazol-3-yl)pyridin-3-yl]-2,2-difluoroacetamide,
Ethyl 2-(5-(2-chloroacetamido)pyridin-2-yl)-5,6-dihydroxypyrimidine-4-carboxylate,
N-(6-carbamimidoylpyridin-3-yl)-2-chloroacetamide,
N-(6-carbamimidoylpyridin-3-yl)acetamide acetate,
N-(6-(5-chloro-4-hydroxy-6-methylpyrimidin-2-yl)pyridin-3-yl)acetamide,
N-(6-(4-hydroxy-5,6-dimethylpyrimidin-2-yl)pyridin-3-yl)acetamide,
2-Chloro-N-(6-(5-chloro-4-hydroxy-6-methylpyrimidin-2-yl)pyridin-3-yl)acetamide,
2-(5-aminopyridin-2-yl)-5,6-dimethylpyrimidin-4-ol,
2-(5-aminopyridin-2-yl)-6-(chloromethyl)pyrimidin-4-ol,
2-Chloro-N-(6-(4-hydroxy-5,6-dimethylpyrimidin-2-yl)pyridin-3-yl)acetamide,
2-Chloro-N-(6-(4-(chloromethyl)-6-hydroxypyrimidin-2-yl)pyridin-3-yl)acetamide,
2-(5-aminopyridin-2-yl)-5-ethyl-6-methylpyrimidin-4-ol,
2-Chloro-N-(6-(4-hydroxy-6-(trifluoromethyl)pyrimidin-2-yl)pyridin-3-yl)acetamide,
2-(5-aminopyridin-2-yl)-5-benzyl-6-methylpyrimidin-4-ol,
6-(4-(allyloxy)-5-chloro-6-methylpyrimidin-2-yl)pyridin-3-amine,
N-(6-(4-(allyloxy)-5-chloro-6-methylpyrimidin-2-yl)pyridin-3yl)-2-chloroacetamide,
6-(4-(allyloxy)-6-(trifluoromethyl)pyrimidin-2-yl)pyridin-3-amine,
6-(4-ethoxy-6-(trifluoromethyl)pyrimidin-2-yl)pyridin-3-amine,
6-(4-methoxy-6-(trifluoromethyl)pyrimidin-2-yl)pyridin-3-amine,
N-(6-(4-(allyloxy)-6-(triflouromethyl)pyrimidin-2-yl)pyridin-3yl-)-2-chloroacetamide,
2-Chloro-N-(6-(4-methoxy-6-(trifluoromethyl)pyrimidin-2-yl)pyridin-3yl)acetamide,
2-Chloro-N-(6-(4-ethoxy-6-(trifluoromethyl)pyrimidin-2-yl)pyridin-3yl)acetamide,
6-(4-(allyloxy)-5-ethyl-6-methylpyrimidin-2-yl)pyridin-3-amine,
N-(6-(4-(allyloxy)-5-ethyl-6-methylpyrimidin-2-yl)pyridin-3yl)-2-chloroacetamide,
2-Chloro-N-(6-(5-ethyl-4-hydroxy-6-methylpyrimidin-2-yl)pyridin-3-yl)acetamide,
2-Chloro-N-(6-(5-chloro-4-hydroxy-6-methylpyrimidin-2-yl)pyridin-3-yl)-2-phenylacetamide,
2-Chloro-N-(6-(4-hydroxy-6-(trifluoromethyl)pyrimidin-2-yl)pyridin-3-yl)-2-phenylacetamide,
2-Chloro-N-(6-(4-hydroxy-6-(trifluoromethyl)pyrimidin-2-yl)pyridin-3-yl)propanamide,
2-Chloro-2,2-difluoro-N-(6-(4-hydroxy-6-(trifluoromethyl)pyrimidin-2-yl)pyridin-3-yl)acetamide,
N-(6-(5-Benzyl-4-hydroxy-6-methylpyrimidin-2-yl)pyridin-3-yl)-2-chloroacetamide,
2-Chloro-N-(6-(4-chloro-6-(trifluoromethyl)pyrimidin-2-yl)pyridin-3-yl)acetamide,
and a pharmaceutically acceptable salt or a solvate thereof.

15. A process for the preparation compound of formula (O);

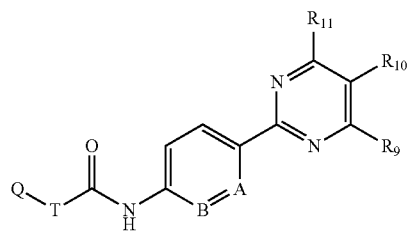

wherein,
A is nitrogen and B is carbon;
T is selected from —$(CR_7R_8)_n$— and —$C(R_7R_8)C(O)$—, where n is an integer from 0 to 5;
$R_7$ and $R_8$ are independently selected from hydrogen, alkyl, haloalkyl, cycloalkyl, alkenyl, halogen, hydroxy, alkoxy, cyano, nitro, aryl, and heterocyclyl;
Q is selected from halogen, cyano, alkoxy, heterocyclyl and cycloalkyl;
$R_9$ is selected from alkyl and haloalkyl;
$R_{10}$ is selected from hydrogen, halogen and alkyl;
$R_{11}$ is selected from hydroxy and halogen;
which comprises:
a) reacting a compound of formula (A) with hydrogen chloride in methanol to obtain a compound of formula (K), further reacting the compound of formula (K) with ammonia in methanol to obtain a compound of formula (L);

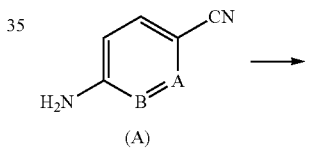

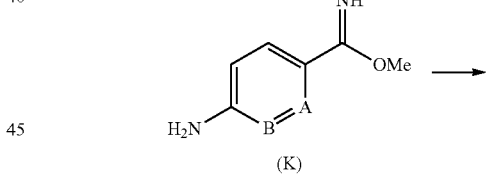

wherein,
A is nitrogen and B is carbon;
b) reacting the compound of formula (L) with a compound of formula (M)

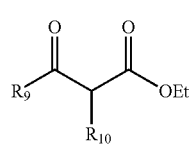

wherein,
R$_9$ is selected from alkyl and haloalkyl; R$_{10}$ is selected from H, halogen and alkyl; in presence of a base selected from sodium carbonate, potassium carbonate, and cesium carbonate; in a solvent selected from methanol, and ethanol; to obtain a compound of formula (N);

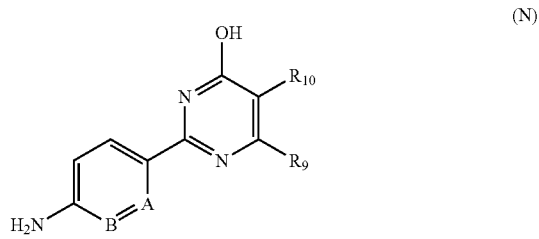

(N)

wherein,
A is nitrogen and B is carbon; R$_9$ is selected from alkyl and haloalkyl; R$_{10}$ is selected from H, halogen and;
c) reacting the compound of formula (N) with a compound of formula (B)

(B)

wherein,
T is selected from —(CR$_7$R$_8$)$_n$— and —C(R$_7$R$_8$)C(O)—, where n is an integer from 0 to 5;
R$_7$ and R$_8$ are independently selected from hydrogen, alkyl, haloalkyl, cycloalkyl, alkenyl, halogen, hydroxy, alkoxy, cyano, nitro, aryl, and heterocyclyl;
Q is selected from halogen, cyano, alkoxy, heterocyclyl and cycloalkyl; in presence of a base selected from triethylamine, potassium carbonate, sodium carbonate, cesium carbonate, and sodium bicarbonate; in an inert solvent selected from chloroform, acetone, dioxane, and tetrahydrofuran; to obtain a compound of formula (O), wherein R$_{11}$ is hydroxy;
d) reacting the compound of formula (O), wherein R$_{11}$ is hydroxy, with a halogenating agent selected from phosphoryl chloride, thionyl chloride and phosphorus pentachloride in presence of a base selected from dimethylaniline, dimethyl aminopyridine and triethylamine, in presence of a solvent selected from acetonitrile, tetrahydrofuran and dioxane, to obtain a compound of general formula (O) wherein R$_{11}$ is halogen; and
e) optionally, converting the compound of formula (O) into a pharmaceutically acceptable salt.

16. A pharmaceutical composition, comprising a therapeutically effective amount of a compound as defined in claim 1, a pharmaceutically acceptable salt or a pharmaceutically acceptable solvate thereof, and a pharmaceutically acceptable carrier or a diluent.

17. A method for the treatment of a condition or a disorder caused by deregulation of signaling pathway selected from one or more of phosphatidylinositol-3-kinase (PI3K) pathway, mammalian target of rapamycin (mTOR) pathway and hypoxia inducible factor 1 alpha (HIF-1α) pathway, which method comprises administering to a mammal in need thereof a therapeutically effective amount of a compound as defined in claim 1, a pharmaceutically acceptable salt or a pharmaceutically acceptable solvate thereof, wherein the condition or disorder is selected from the group consisting of bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer and renal cancer.

18. A method for the treatment of a condition or a disorder mediated by PI3K or TNF-α activity, which method comprises administering to a mammal in need thereof a therapeutically effective amount of a compound as defined in claim 1, a pharmaceutically acceptable salt or a pharmaceutically acceptable solvate thereof, wherein the condition or disorder is selected from the group consisting of inflammatory bowel disease, inflammation, rheumatoid arthritis, juvenile rheumatoid arthritis, psoriatic arthritis, osteo-arthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegener's granulomatosis, meningitis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, ankylosing spondylitis, skin delayed-type hypersensitivity disorders, Alzheimer's disease, systemic lupus erythematosus and allergic disorders.

* * * * *